United States Patent
Buchberger

(10) Patent No.: US 10,543,323 B2
(45) Date of Patent: *Jan. 28, 2020

(54) INHALER

(71) Applicant: BATMARK LIMITED, London (GB)

(72) Inventor: Helmut Buchberger, Ennsdorf (AT)

(73) Assignee: Batmark Limited, London (GB)

( * ) Notice: Subject to any disclaimer, the term of this patent is extended or adjusted under 35 U.S.C. 154(b) by 887 days.

This patent is subject to a terminal disclaimer.

(21) Appl. No.: 14/296,803

(22) Filed: Jun. 5, 2014

(65) Prior Publication Data

US 2014/0283825 A1 Sep. 25, 2014

Related U.S. Application Data

(63) Continuation of application No. 13/125,343, filed as application No. PCT/AT2009/000414 on Oct. 21, 2009, now Pat. No. 8,833,364.

(30) Foreign Application Priority Data

Oct. 23, 2008 (AT) .................................. A 1660/2008
Apr. 17, 2009 (AT) .................................. A 597/2009

(51) Int. Cl.
*A61M 15/06* (2006.01)
*A24F 47/00* (2006.01)
(Continued)

(52) U.S. Cl.
CPC ......... *A61M 11/042* (2014.02); *A24F 47/002* (2013.01); *A24F 47/008* (2013.01);
(Continued)

(58) Field of Classification Search
CPC ...... A24F 47/00; A24F 47/002; A24F 47/004; A24F 47/005; A24F 47/008;
(Continued)

(56) References Cited

U.S. PATENT DOCUMENTS 2,057,353 A    10/1936  Whittemore, Jr. .............. 219/38
2,809,634 A    10/1957  Murai
(Continued)

FOREIGN PATENT DOCUMENTS

AT    508244    12/2010
AT    510405    4/2012
(Continued)

OTHER PUBLICATIONS

International Search Report dated Jan. 26, 2010 in corresponding International Application No. PCT/AT2009/000414 (4 pages).
(Continued)

*Primary Examiner* — Timothy A Stanis
(74) *Attorney, Agent, or Firm* — Patterson Thuente Pedersen, PA

(57) ABSTRACT

The present disclosure relates to an inhaler component for producing a steam/air mixture or/and condensation aerosol in an intermittent and inhalation- or pull-synchronous manner, the inhaler component including: a housing; a chamber arranged in the housing; an air inlet opening for the supply of air from the surroundings to the chamber; an electrical heating element for evaporating a portion of a liquid material; and a wick having a capillary structure, which wick forms a composite structure with the heating element and automatically supplies the heating element with fresh liquid material after evaporation.

15 Claims, 29 Drawing Sheets

(51) Int. Cl.
*A61M 11/04* (2006.01)
*A61M 15/00* (2006.01)
*A61K 31/465* (2006.01)
*A61M 16/00* (2006.01)

(52) U.S. Cl.
CPC ......... *A61K 31/465* (2013.01); *A61M 11/041* (2013.01); *A61M 15/0021* (2014.02); *A61M 15/0086* (2013.01); *A61M 15/06* (2013.01); *A61M 2016/0021* (2013.01); *A61M 2205/11* (2013.01); *A61M 2205/3606* (2013.01); *A61M 2205/3653* (2013.01); *A61M 2205/7536* (2013.01); *A61M 2205/8206* (2013.01); *A61M 2205/8237* (2013.01)

(58) Field of Classification Search
CPC .............. A61M 15/0021; A61M 15/06; A61M 15/0086; A61M 11/041; A61M 11/042
See application file for complete search history.

(56) References Cited

U.S. PATENT DOCUMENTS

| | | | |
|---|---|---|---|
| 3,111,396 A | 11/1963 | Ball | 25/156 |
| 3,402,724 A | 6/1968 | Blount | |
| 3,431,393 A | 3/1969 | Katsuda | 392/395 |
| 3,433,632 A | 3/1969 | Elbert et al. | 75/222 |
| 3,521,643 A | 7/1970 | Toth | |
| 3,604,428 A | 9/1971 | Moukaddem | |
| 3,804,100 A | 4/1974 | Fariello | |
| 3,964,902 A * | 6/1976 | Fletcher | B22F 3/002 165/104.26 |
| 4,009,713 A | 3/1977 | Simmons et al. | 128/200.18 |
| 4,031,906 A | 6/1977 | Knapp | |
| 4,094,119 A | 6/1978 | Sullivan | |
| 4,145,001 A | 3/1979 | Weyenberg | |
| 4,161,283 A | 7/1979 | Hyman | |
| 4,193,513 A | 3/1980 | Bull | |
| 4,503,851 A | 3/1985 | Brauroth | |
| 4,588,976 A | 5/1986 | Jaselli | |
| 4,676,237 A | 6/1987 | Wood et al. | 128/203.17 |
| 4,677,992 A | 7/1987 | Bliznak | |
| 4,735,217 A | 4/1988 | Gerth | |
| 4,830,028 A | 5/1989 | Lawson | |
| 4,848,374 A | 7/1989 | Chard et al. | 131/330 |
| 4,885,129 A * | 12/1989 | Leonard | B22F 3/22 29/890.032 |
| 4,917,301 A | 4/1990 | Munteanu | |
| 4,922,901 A | 5/1990 | Brooks et al. | 128/203.26 |
| 4,947,874 A | 8/1990 | Brooks et al. | 131/329 |
| 4,947,875 A | 8/1990 | Brooks | |
| 4,978,814 A | 12/1990 | Honour | 174/94 R |
| 5,027,837 A | 7/1991 | Clearman | |
| 5,046,514 A | 9/1991 | Bolt | |
| 5,060,671 A | 10/1991 | Counts | |
| 5,095,647 A | 3/1992 | Zobele | |
| 5,095,921 A | 3/1992 | Bollinger et al. | |
| 5,099,861 A | 3/1992 | Clearman et al. | |
| 5,121,881 A | 6/1992 | Lembeck | |
| 5,167,242 A | 12/1992 | Turner | |
| 5,179,966 A | 1/1993 | Losee | |
| 5,247,947 A | 9/1993 | Clearman | |
| 5,322,075 A | 6/1994 | Deevi et al. | |
| 5,388,574 A | 2/1995 | Ingebrethsen | |
| 5,390,864 A | 2/1995 | Alexander | |
| 5,479,948 A * | 1/1996 | Counts | A24F 47/008 131/194 |
| 5,497,792 A | 3/1996 | Prasad | |
| 5,501,236 A | 3/1996 | Hill | |
| 5,505,214 A | 4/1996 | Collins | |
| 5,540,241 A | 7/1996 | Kim | |
| 5,553,791 A | 9/1996 | Alexander | |
| 5,636,787 A | 6/1997 | Gowhari | |
| 5,649,554 A | 7/1997 | Murphy | |
| 5,666,977 A | 9/1997 | Higgins et al. | 131/194 |
| 5,692,291 A | 12/1997 | Seetharama | |
| 5,743,251 A | 4/1998 | Howell et al. | |
| 5,865,185 A | 2/1999 | Collins et al. | 131/194 |
| 6,058,711 A | 5/2000 | Maduyt | |
| 6,095,505 A | 8/2000 | Miller | |
| 6,155,268 A | 12/2000 | Manabu | |
| 6,275,650 B1 | 8/2001 | Lambert | 392/395 |
| 6,652,804 B1 | 11/2003 | Neumann et al. | 419/2 |
| 6,681,998 B2 * | 1/2004 | Sharpe | A61M 11/042 128/203.26 |
| 6,701,921 B2 * | 3/2004 | Sprinkel, Jr. | A61M 11/041 128/203.17 |
| 6,790,496 B1 | 9/2004 | Levander et al. | |
| 7,100,618 B2 | 9/2006 | Dominiquez | |
| 7,112,712 B1 | 9/2006 | Ancell | 602/41 |
| 7,263,282 B2 | 8/2007 | Meyer | |
| 7,400,940 B2 | 7/2008 | McRae et al. | 700/266 |
| 7,540,286 B2 | 6/2009 | Cross | |
| 7,767,698 B2 | 8/2010 | Warchol | |
| 7,832,410 B2 | 11/2010 | Hon | |
| 7,992,554 B2 * | 8/2011 | Radomski | A61M 16/16 128/203.12 |
| 8,156,944 B2 | 4/2012 | Hon | |
| 8,365,742 B2 | 2/2013 | Hon | |
| 8,375,957 B2 | 2/2013 | Hon | |
| 8,393,331 B2 | 3/2013 | Hon | |
| 8,430,106 B2 | 4/2013 | Potter et al. | |
| 8,490,628 B2 | 7/2013 | Hon | |
| 8,511,318 B2 | 8/2013 | Hon | |
| 8,752,545 B2 | 6/2014 | Buchberger | |
| 8,689,805 B2 | 8/2014 | Hon | |
| 8,833,364 B2 | 9/2014 | Buchberger | |
| 8,948,578 B2 | 2/2015 | Buchberger | |
| 9,609,894 B2 | 4/2017 | Abramov | |
| 9,623,205 B2 | 4/2017 | Buchberger | |
| 10,010,695 B2 | 7/2018 | Buchberger | |
| 10,045,562 B2 | 8/2018 | Buchberger | |
| 2001/0042546 A1 | 11/2001 | Umeda et al. | |
| 2002/0005207 A1 | 1/2002 | Wrenn | |
| 2002/0016370 A1 | 2/2002 | Shytle | |
| 2002/0079309 A1 | 6/2002 | Cox | |
| 2003/0005620 A1 * | 1/2003 | Ananth | A01M 1/2077 43/125 |
| 2003/0049025 A1 | 3/2003 | Neumann | |
| 2003/0079309 A1 | 6/2003 | Cox | |
| 2003/0106552 A1 | 6/2003 | Sprinkel | |
| 2003/0108342 A1 | 6/2003 | Sherwood | |
| 2003/0200964 A1 | 10/2003 | Blakley | |
| 2003/0202169 A1 | 10/2003 | Liu | |
| 2004/0031485 A1 * | 2/2004 | Rustad | A61M 11/00 128/200.18 |
| 2004/0129793 A1 | 7/2004 | Nguyen et al. | |
| 2004/0210151 A1 | 10/2004 | Tsukashima | |
| 2004/0226568 A1 | 11/2004 | Takeuchi | |
| 2005/0145260 A1 | 7/2005 | Inagaki | |
| 2005/0194013 A1 | 9/2005 | Wright | |
| 2005/0204799 A1 | 9/2005 | Koch | |
| 2005/0268911 A1 | 12/2005 | Cross et al. | 128/204.17 |
| 2006/0078477 A1 * | 4/2006 | Althouse | A01M 1/2044 422/123 |
| 2006/0137681 A1 | 6/2006 | Von Hollen | |
| 2007/0014549 A1 | 1/2007 | Demarest et al. | |
| 2007/0045288 A1 | 3/2007 | Nelson | |
| 2007/0062548 A1 | 3/2007 | Horstmann | |
| 2007/0102013 A1 | 5/2007 | Adams | |
| 2007/0107879 A1 | 5/2007 | Radomski | 165/104.26 |
| 2007/0155255 A1 | 7/2007 | Galauner | |
| 2008/0092912 A1 | 4/2008 | Robinson | |
| 2008/0156326 A1 | 7/2008 | Belcastro | |
| 2008/0216828 A1 | 9/2008 | Wensley | |
| 2008/0241255 A1 | 10/2008 | Rose | |
| 2009/0090472 A1 | 4/2009 | Radomski | |
| 2009/0095311 A1 | 4/2009 | Han | |
| 2009/0188490 A1 | 7/2009 | Han | |
| 2009/0241947 A1 | 10/2009 | Bedini | |
| 2009/0272379 A1 | 11/2009 | Thorens | |
| 2009/0293892 A1 | 12/2009 | Williams | |
| 2010/0059070 A1 | 3/2010 | Potter et al. | |

(56) References Cited

U.S. PATENT DOCUMENTS

| | | | |
|---|---|---|---|
| 2010/0065653 A1* | 3/2010 | Wingo | B05B 17/0684 239/6 |
| 2010/0083959 A1* | 4/2010 | Siller | A24F 47/006 128/202.21 |
| 2010/0108059 A1 | 5/2010 | Axelsson et al. | |
| 2014/0182608 A1 | 7/2010 | Egoyants | |
| 2010/0236546 A1 | 9/2010 | Yamada | |
| 2010/0242974 A1 | 9/2010 | Pan | |
| 2011/0011396 A1 | 1/2011 | Fang | |
| 2011/0126848 A1 | 6/2011 | Zuber | |
| 2011/0155153 A1 | 6/2011 | Thorens | |
| 2011/0192914 A1 | 8/2011 | Ishigami | |
| 2011/0226236 A1 | 9/2011 | Buchberger | |
| 2011/0277757 A1 | 11/2011 | Terry | |
| 2011/0036363 A1 | 12/2011 | Urtsev | |
| 2011/0290267 A1 | 12/2011 | Yamada | |
| 2011/0297166 A1 | 12/2011 | Takeuchi | |
| 2011/0303231 A1 | 12/2011 | Li | |
| 2012/0145169 A1 | 6/2012 | Wu | |
| 2012/0260927 A1 | 10/2012 | Qiuming | |
| 2012/0285476 A1 | 11/2012 | Hon | |
| 2013/0074857 A1 | 3/2013 | Buchberger | |
| 2013/0081623 A1 | 4/2013 | Buchberger | |
| 2013/0087160 A1 | 4/2013 | Gherghe | |
| 2013/0142782 A1 | 6/2013 | Rahmel et al. | |
| 2013/0192615 A1 | 8/2013 | Tucker | |
| 2013/0213419 A1 | 8/2013 | Tucker | |
| 2013/0284192 A1 | 10/2013 | Peleg | |
| 2013/0333700 A1 | 12/2013 | Buchberger | |
| 2013/0340779 A1 | 12/2013 | Liu | |
| 2014/0000638 A1 | 1/2014 | Sebastian | |
| 2014/0060528 A1 | 3/2014 | Liu | |
| 2014/0060554 A1 | 3/2014 | Collett | |
| 2014/0060555 A1 | 3/2014 | Chang | |
| 2014/0202454 A1 | 7/2014 | Buchberger | |
| 2014/0202476 A1 | 7/2014 | Egoyants | |
| 2014/0209105 A1 | 7/2014 | Sears | |
| 2014/0216485 A1 | 8/2014 | Egoyants | |
| 2014/0238396 A1 | 8/2014 | Buchberger | |
| 2014/0238423 A1 | 8/2014 | Tucker | |
| 2014/0238424 A1 | 8/2014 | Tucker | |
| 2014/0261490 A1 | 9/2014 | Kane | |
| 2014/0270726 A1 | 9/2014 | Egoyants | |
| 2014/0270730 A1 | 9/2014 | DePiano | |
| 2014/0283825 A1 | 9/2014 | Buchberger | |
| 2014/0286630 A1 | 9/2014 | Buchberger | |
| 2014/0299125 A1 | 10/2014 | Buchberger | |
| 2014/0338680 A1 | 11/2014 | Abramov et al. | |
| 2015/0114411 A1 | 4/2015 | Buchberger | |
| 2015/0157055 A1 | 6/2015 | Lord | |
| 2015/0196058 A1 | 7/2015 | Lord | |
| 2015/0208728 A1 | 7/2015 | Lord | |
| 2016/0073693 A1 | 3/2016 | Reevell | |
| 2016/0106154 A1 | 4/2016 | Lord | |
| 2016/0106155 A1 | 4/2016 | Reevell | |
| 2017/0006916 A1 | 1/2017 | Liu | |
| 2017/0042245 A1 | 2/2017 | Buchberger | |
| 2017/0197043 A1 | 7/2017 | Buchberger | |
| 2017/0197044 A1 | 7/2017 | Buchberger | |
| 2017/0197046 A1 | 7/2017 | Buchberger | |

FOREIGN PATENT DOCUMENTS

| | | |
|---|---|---|
| AT | 510504 | 4/2012 |
| AU | 63931/73 | 6/1975 |
| CA | 2309376 | 5/2000 |
| CA | 2309376 | 11/2000 |
| CH | 698603 B1 | 9/2009 |
| CN | 2092880 | 1/1992 |
| CN | 2220168 | 2/1996 |
| CN | 1205849 A | 1/1999 |
| CN | 2719043 | 8/2005 |
| CN | 1694765 A | 11/2005 |
| CN | 201238609 | 5/2009 |
| CN | 201375023 | 1/2010 |
| CN | 201375023 Y | 1/2010 |
| CN | 101648041 A | 2/2010 |
| CN | 101648041 A | 2/2010 |
| CN | 101878958 | 11/2010 |
| CN | 202172846 | 3/2012 |
| CN | 102655773 A | 9/2012 |
| CN | 202722498 | 2/2013 |
| CN | 202750708 | 2/2013 |
| CN | 106102863 A | 11/2016 |
| DE | 1 950 439 | 4/1971 |
| DE | 31 48 335 | 7/1983 |
| DE | 3148335 | 7/1983 |
| DE | 32 18 760 | 12/1983 |
| DE | 3218760 | 12/1983 |
| DE | 39 36 687 | 5/1990 |
| DE | 3936687 | 5/1992 |
| DE | 29719509 | 1/1998 |
| DE | 29719509 U1 | 1/1998 |
| DE | 196 30 619 | 2/1998 |
| DE | 196 54 945 | 3/1998 |
| DE | 19654945 | 3/1998 |
| DE | 103 30 681 | 6/2004 |
| DE | 10330681 | 6/2004 |
| DE | 20 2006 013 439 | 10/2006 |
| DE | 202006013439 | 10/2006 |
| DE | 202013100606 | 2/2013 |
| EP | 280262 | 8/1988 |
| EP | 0358002 A2 | 3/1990 |
| EP | 0358114 | 3/1990 |
| EP | 0444553 | 9/1991 |
| EP | 0488488 | 6/1992 |
| EP | 0845220 | 6/1998 |
| EP | 0295122 | 12/1998 |
| EP | 0 893 071 | 1/1999 |
| EP | 0893071 | 1/1999 |
| EP | 1 166 814 | 1/2002 |
| EP | 1166814 | 1/2002 |
| EP | 1166847 | 1/2002 |
| EP | 1 736 065 | 12/2006 |
| EP | 1736065 | 12/2006 |
| EP | 1757921 A2 | 2/2007 |
| EP | 2018886 | 1/2009 |
| EP | 2 022 349 | 2/2009 |
| EP | 2 113 178 | 11/2009 |
| EP | 2113178 | 11/2009 |
| EP | 2340729 A1 | 7/2011 |
| EP | 2698070 | 2/2014 |
| EP | 2907397 | 4/2014 |
| EP | 2762019 | 8/2014 |
| EP | 2835062 | 2/2015 |
| FR | 960469 | 4/1950 |
| GB | 25575 | 3/1912 |
| GB | 1 313 525 | 10/1970 |
| HK | 1196511 | 12/2014 |
| HK | 1226611 | 10/2017 |
| JP | S57-052456 | 3/1982 |
| JP | S59-106340 | 1/1986 |
| JP | 61-096765 | 5/1986 |
| JP | S61-096763 | 5/1986 |
| JP | 2124081 | 5/1990 |
| JP | H5-103836 | 4/1993 |
| JP | H05-309136 | 11/1993 |
| JP | H6-315366 A | 11/1994 |
| JP | H8-511176 | 10/1995 |
| JP | H08-299862 | 11/1996 |
| JP | 11089551 | 4/1999 |
| JP | 2011518567 | 1/2002 |
| JP | 2002-527153 | 8/2002 |
| JP | 2004-332069 | 11/2004 |
| JP | 2005-538159 | 12/2005 |
| JP | 2005537918 A | 12/2005 |
| JP | 2009-509523 | 3/2009 |
| JP | 2009-537119 | 10/2009 |
| JP | 2012-249854 | 12/2012 |
| KR | 20130006714 | 11/2013 |
| RU | 2311859 C2 | 12/2007 |
| RU | 2336001 C2 | 10/2008 |
| RU | 89927 U1 | 12/2009 |

(56) References Cited

FOREIGN PATENT DOCUMENTS

| | | |
|---|---|---|
| RU | 94815 U1 | 6/2010 |
| RU | 103281 U1 | 4/2011 |
| RU | 115629 U1 | 5/2012 |
| RU | 122000 U1 | 11/2012 |
| RU | 124120 | 1/2013 |
| RU | 132318 | 9/2013 |
| RU | 2509516 | 3/2014 |
| WO | WO9527412 | 10/1995 |
| WO | WO9632854 | 10/1996 |
| WO | WO9748293 A1 | 12/1997 |
| WO | WO98017131 | 4/1998 |
| WO | WO 98017131 | 4/1998 |
| WO | WO200009188 | 2/2000 |
| WO | WO 00/21598 | 4/2000 |
| WO | WO200021598 | 4/2000 |
| WO | WO2000050111 | 8/2000 |
| WO | WO 2002051468 | 7/2002 |
| WO | WO2002058747 | 8/2002 |
| WO | WO2002058747 A1 | 8/2002 |
| WO | WO 03/028409 | 4/2003 |
| WO | WO2003028409 A1 | 4/2003 |
| WO | WO 03/050405 | 6/2003 |
| WO | WO2003083283 A1 | 10/2003 |
| WO | WO 03/101454 | 12/2003 |
| WO | WO2004/022128 | 3/2004 |
| WO | WO2004022242 | 3/2004 |
| WO | WO2004022243 | 3/2004 |
| WO | WO2005106350 A2 | 11/2005 |
| WO | WO 2006/082571 | 8/2006 |
| WO | WO2006082571 | 8/2006 |
| WO | WO 2007/042941 | 4/2007 |
| WO | WO 2007/131449 | 11/2007 |
| WO | WO 2007131449 A1 * 11/2007 ........... A24F 47/008 |  |
| WO | WO 2007/141668 | 12/2007 |
| WO | WO 2008038144 | 4/2008 |
| WO | WO 2009/015410 | 2/2009 |
| WO | WO2009015410 | 2/2009 |
| WO | WO2009118085 A1 | 10/2009 |
| WO | WO2009132793 A1 | 11/2009 |
| WO | WO2010045670 A1 | 4/2010 |
| WO | WO2010045671 A1 | 4/2010 |
| WO | WO 2011/050943 | 5/2011 |
| WO | WO2011109849 A1 | 9/2011 |
| WO | WO2012025496 A1 | 3/2012 |
| WO | WO2013034453 A1 | 3/2013 |
| WO | WO2013034460 A1 | 3/2013 |
| WO | WO2013057185 A1 | 4/2013 |
| WO | WO 2013/082173 | 6/2013 |
| WO | WO2013098395 A1 | 7/2013 |
| WO | WO2013116558 | 8/2013 |
| WO | WO2013116572 | 8/2013 |
| WO | WO2014130695 | 8/2013 |
| WO | WO2013152873 A1 | 10/2013 |
| WO | WO 2014/012906 | 1/2014 |
| WO | WO2014061477 A1 | 4/2014 |
| WO | WO2014140320 A1 | 9/2014 |
| WO | WO2014150131 A1 | 9/2014 |
| WO | WO 2015/114328 | 8/2015 |
| WO | WO 2015/165812 | 11/2015 |

OTHER PUBLICATIONS

Kynol, Standard Specifications of Kynol Activated Carbon Fiber Products, published by Kynol.
Japanese Notice of Reasons for Rejection dated Sep. 8, 2015 for Japanese Application No. 2014179732.
Japanese Notice of Reasons for Rejection dated Oct. 15, 2013 for Japanese Application No. 2011532464.
Application and File History for U.S. Appl. No. 13/125,343, filed Apr. 21, 2011, inventor Buchberger.
Application and File History for U.S. Appl. No. 14/306,831, filed Jun. 17, 2014, inventor Buchberger.
Dunn et al., "Heat Pipes". Fourth Edition. Pergamon. (1994) 14 pages. ISBN 0080419038.
European Search Report for European Application No. 16166656 dated Oct. 11, 2016.
Notice of Opposition Letter from EPO. Opposition against: EP2358418 dated Mar. 1, 2017.
Rudolph G, BAT Cigarettenfabriken GmbH, 1987, The Influence of $CO_2$ on the Sensory Characteristics of the Favor-System, http://legacylibrary.ucsf.edu/tid/sla51f00.
Application and File History for U.S. Appl. No. 15/470,078, filed Mar. 27, 2017, inventor Buchberger.
Application and File History for U.S. Appl. No. 15/470,089, filed Mar. 27, 2017, inventor Buchberger.
Application and File History for U.S. Appl. No. 15/470,095, filed Mar. 27, 2017, inventor Buchberger.
Japanese Notification of Reasons for Refusal for Japanese Application No. 2014179732 dated Sep. 3, 2015 and dated Sep. 8, 2015.
Japanese Notice of Reasons for Refusal, dated Oct. 7, 2013 and dated Oct. 15, 2013 for Japanese Application No. 2011532464.
International Search Report for International Application No. PCT/AT2009/000413 dated Jan. 25, 2010.
Translation of Chinese First Office Action for Chinese Application No. 200980152395.4 dated Dec. 3, 2012.
Translation of Chinese Second Office Action for Chinese Application No. 200980152395.4 dated Aug. 20, 2013.
Japanese Reasons for Rejection for Japanese Application No. 2016134648 dated May 23, 2017.
International Preliminary Report on Patentability for corresponding International Application No. PCT/GB2015/051213 dated Jul. 14, 2016.
International Search Report for corresponding International Application No. PCT/GB2015/051213 dated Jul. 16, 2015.
Written Opinion of the International Preliminary Examining Authority for International Application No. PCT/GB2015/051213 dated Mar. 29, 2016.
International Search Report and Written Opinion dated Feb. 6, 2013 for PCT/EP0212/070647 filed Oct. 18, 2012.
Chinese Office Action for Chinese Application No. 201480024978.X dated Jan. 18, 2017.
European Search Report for European Application No. 15178588 dated Apr. 14, 2016.
International Preliminary Report on Patentability, dated Apr. 22, 2014, for International Patent Application No. PCT/EP2012/070647, filed Oct. 18, 2012.
International Search Report and Written Opinion for International Application No. PCT/EP2012/003103 dated Nov. 26, 2012.
International Search Report and Written Opinion for PCT/AT/2012/000017 dated Jul. 3, 2012.
International Search Report and Written Opinion for PCT/GB2014/051333 dated Jul. 17, 2014.
International Search Report and Written Opinion, International Application No. PCT/GB2014/051332 dated Jul. 21, 2014.
International Search Report and Written Opinion, International Application No. PCT/GB2014/051334 dated Jul. 21, 2014.
IPRP dated Aug. 5, 2015 for International Application No. PCT/GB2014/051333.
IPRP, International Application No. PCT/GB2014/051332 dated Nov. 12, 2015.
IPRP, International Application No. PCT/GB2014/051334 dated Nov. 12, 2015.
Japanese Notice of Reasons for Rejection for Japanese Application No. 2015-137361 dated May 31, 2016.
Russian Search Report for Russian Application No. 2015146843/12 (072088) date completed Apr. 24, 2017.
Russian Office Action, Application No. 2014120213/12, dated Oct. 26, 2016, 7 pages.
Russian Office Action, Application No. 2014120213/12, dated Sep. 22, 2017, 11 pages.
Chinese Office Action, Application No. 201480024988.3, dated Dec. 30, 2016, 26 pages.
Chinese Office Action, Application No. 201480024988.3, dated Sep. 11, 2017, 21 pages.
European Extended Search Report, Application No. 17189951.1, dated Jan. 4, 2018, 8 pages (11 pages with translation).

(56) References Cited

OTHER PUBLICATIONS

Plasma polymerization (the company Diener electronic GmbH+Co. KG), www.plasma.de, retrieved on Oct. 17, 2017, 19 pages.
International Preliminary Report on Patentability (WIPO English Translation), dated Aug. 13, 2013 for International Patent Application No. PCT/AT2012/000017, filed Feb. 2, 2012.
Pulmonary Pharmacoloy: Delivery Devices and Medications, dated Sep. 6, 2017, 2 pages, available at www.cdeu.org/cecourses/z98207/ch4.htm.
Japanese Decision to Grant, Application No. 2016-134648, dated May 22, 2018, 3 pages (4 pages with translation).
Japanese Office Action, Application No. 2016-564977, dated Dec. 5, 2017, 3 pages (6 pages with translation).
Japanese Search Report, Application No. 2016-864977, dated Oct. 25, 2017, 9 pages (19 pages with translation).
Chinese Office Action, Application No. 201580022356.8, dated Jul. 18, 2018, 8 pages (15 pages with translation).
Chinese Office Action and Search Report, Application No. 201610371843.1, dated Sep. 30, 2018, 6 pages (11 pages with translation).
Japanese Decision to Grant, Application No. JP2016-134648, dated May 22, 2018, 6 pages.
Application and File History for U.S. Appl. No. 15/997,113, filed Jun. 4, 2018.
Application and File History for U.S. Appl. No. 14/594,065, filed Jan. 9, 2015.
Application and File History for U.S. Appl. No. 16/096,554, filed Oct. 25, 2018.
Chinese Search Report, Application No. 201610086101.4, dated Apr. 25, 2018, 1 page.
Chinese Office Action, 201610086101.4, dated May 4, 2018, 3 pages.
Chinese Notification to Grant Patent, Application No. 201610086101.4, dated Oct. 25, 2018, 2 pages.
Russian Decision to Grant Application No. 2011120430/14, dated Apr. 1, 2014, 10 pages.
Japanese Search Report, Application No. 2016-134648, dated Apr. 14, 2017, 26 pages.
Japanese Search Report, Application No. 2014-179732, dated Aug. 25, 2015, 5 pages.
Japanese Search Report, Application No. 2011-532464, dated Sep. 19, 2013, 116 pages.
Company Filtrona Richmond, Inc., www.filtronaporoustechnologies.com, dated Nov. 19, 2018.
Japanese Decision to Grant, Application No. 2011-532464, dated Aug. 5, 2014, 3 pages (6 pages with translation).
International Preliminary Report on Patentability, Application No. PCT/GB2017/051139, dated Aug. 6, 2018, 8 pages.
International Search Report and Written Opinion, Application No. PCT/GB2017/051139, dated Aug. 9, 2017, 16 pages.
Japanese Office Action and Search Report, Application No. 2018-088088, dated Feb. 28, 2019, 25 pages.
European Communication, Application No. 17189951.1, dated Jan. 25, 2019, 4 pages.
European Search Report, Application No. 18205608.5, dated Jul. 12, 2019, 7 pages.
Russian Search Report, Application No. 2018137501, dated Apr. 29, 2019, 12 pages.

\* cited by examiner

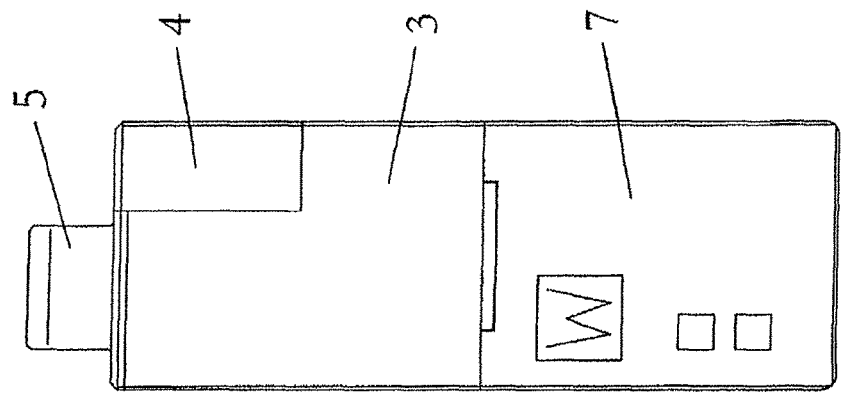
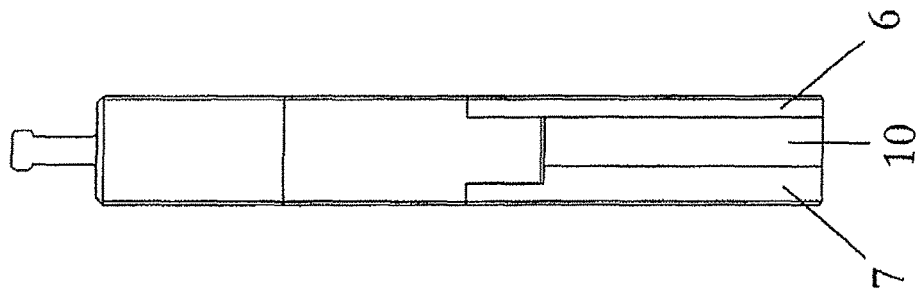
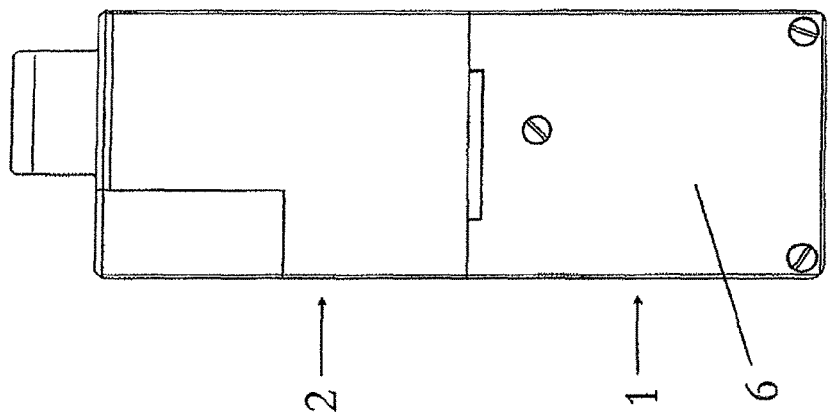

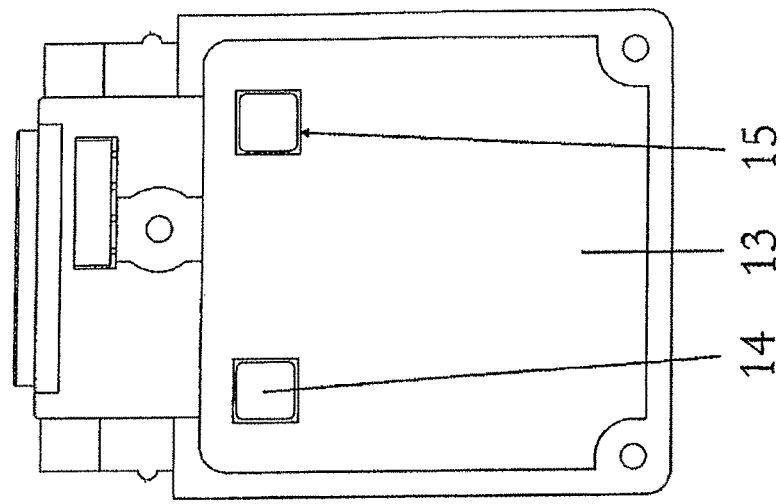
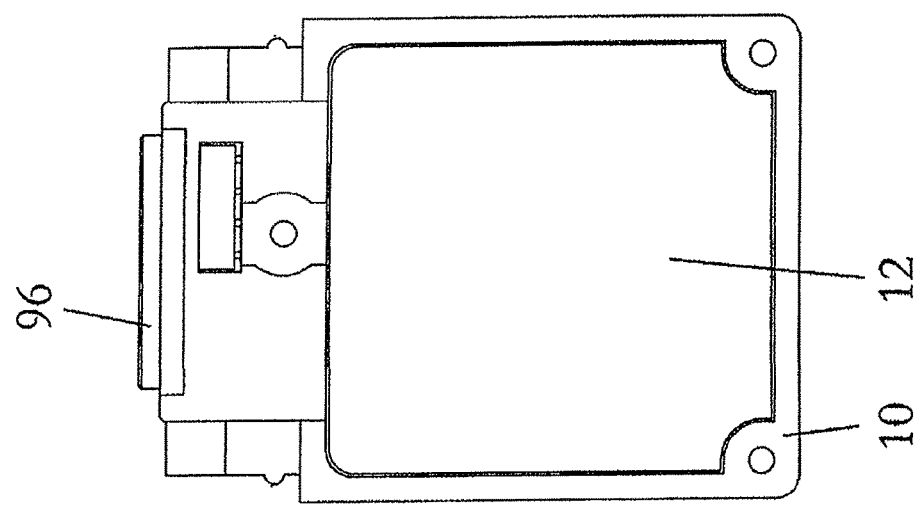
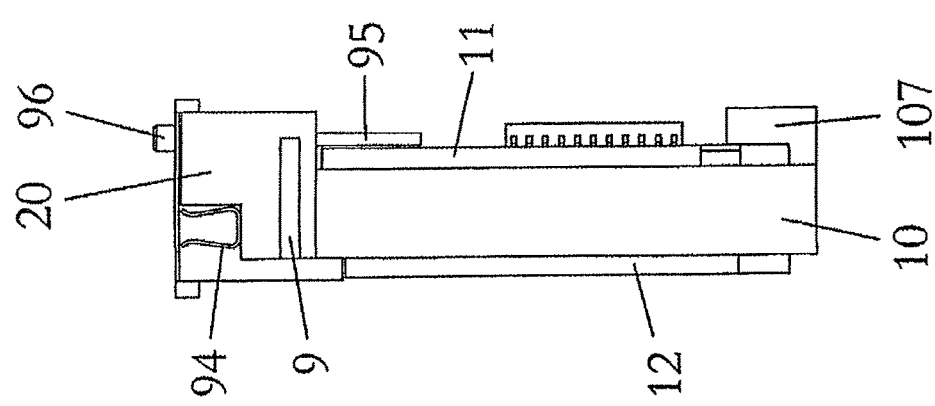
FIG. 5C
FIG. 5B
FIG. 5A

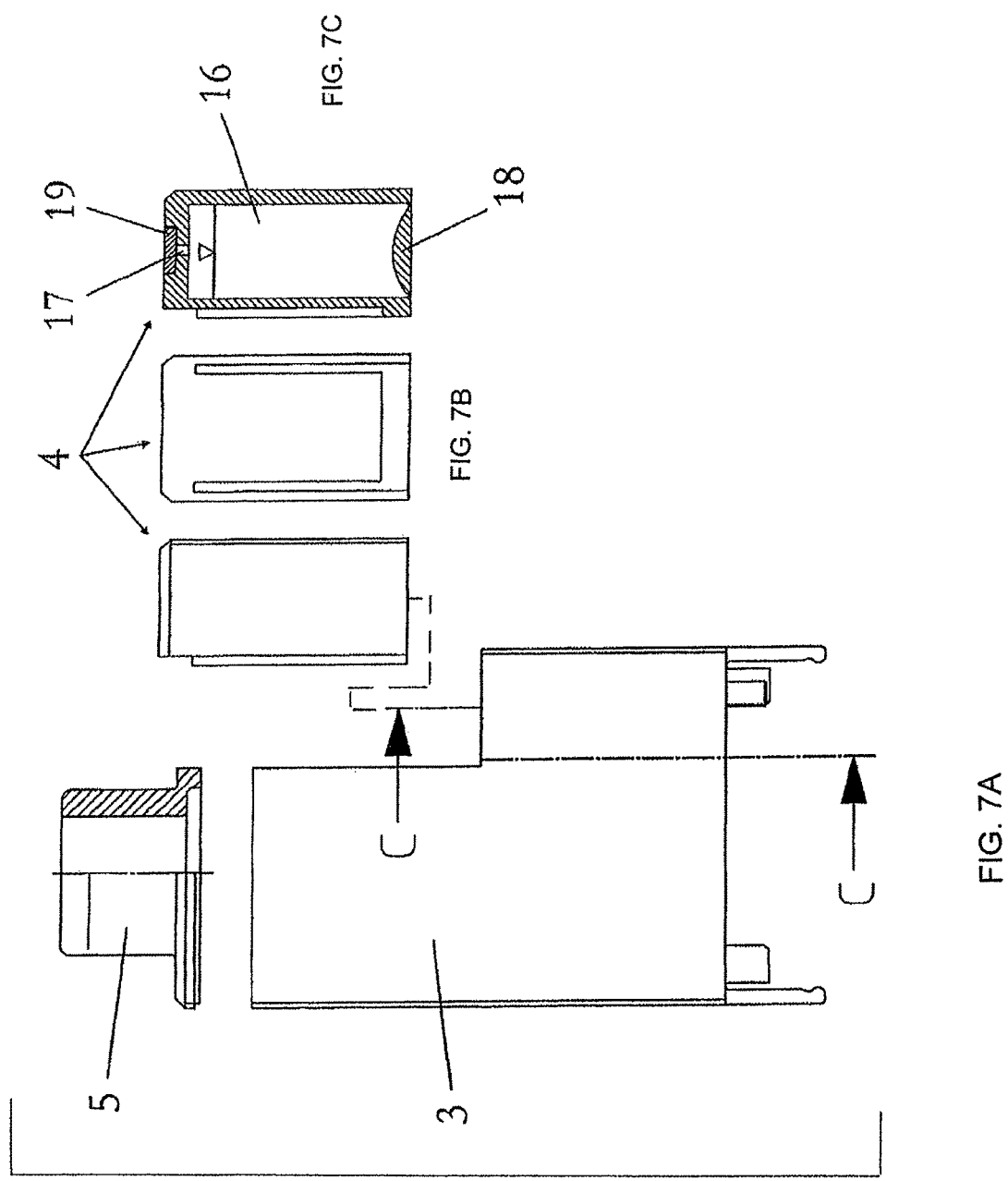

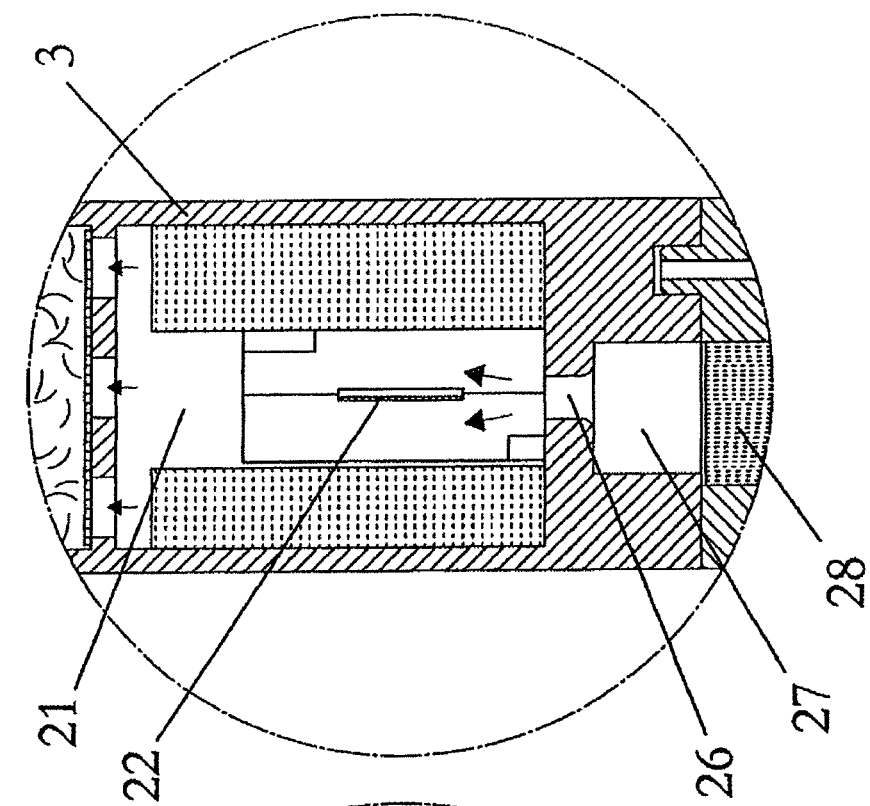
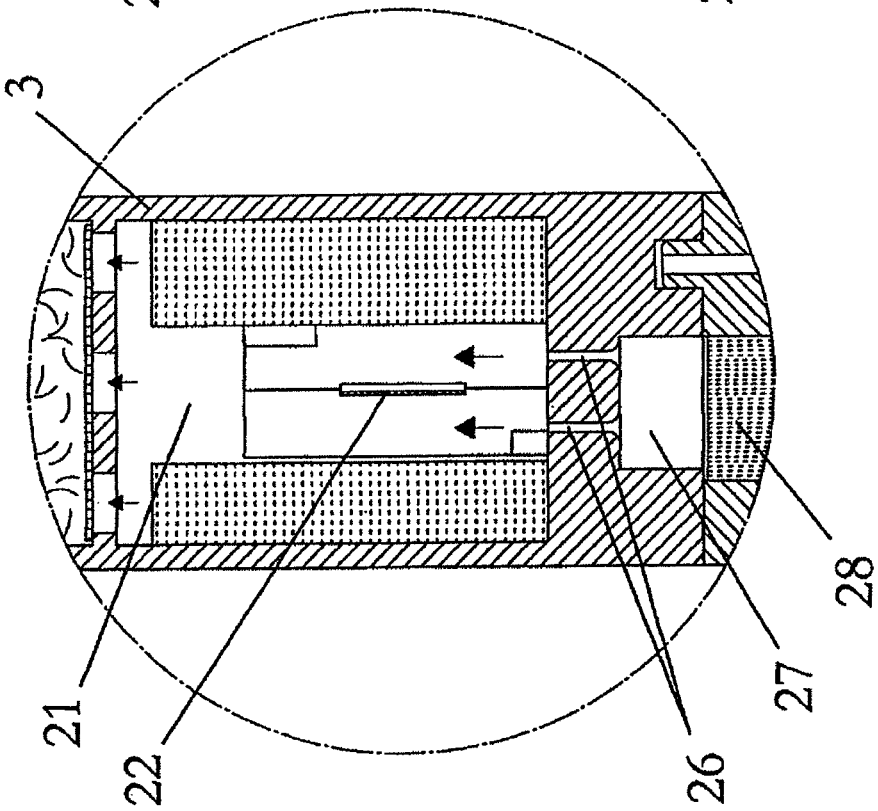
Fig. 13a
Fig. 13b

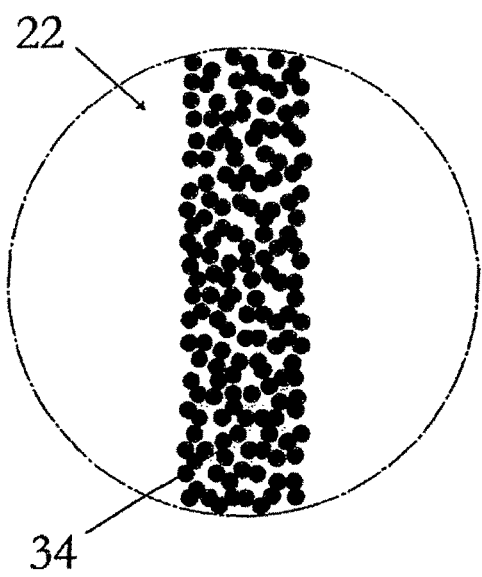
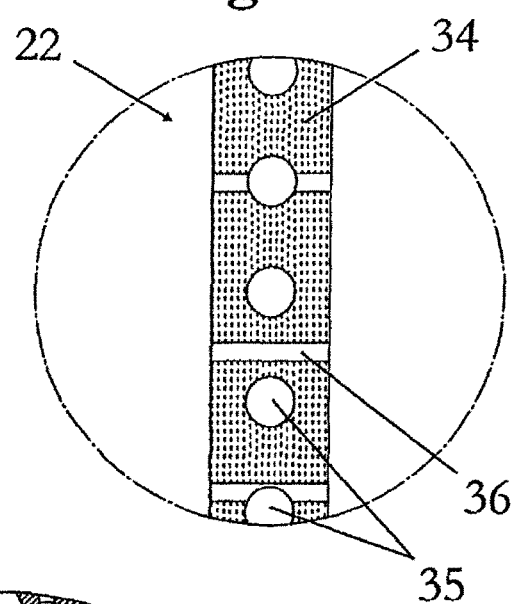
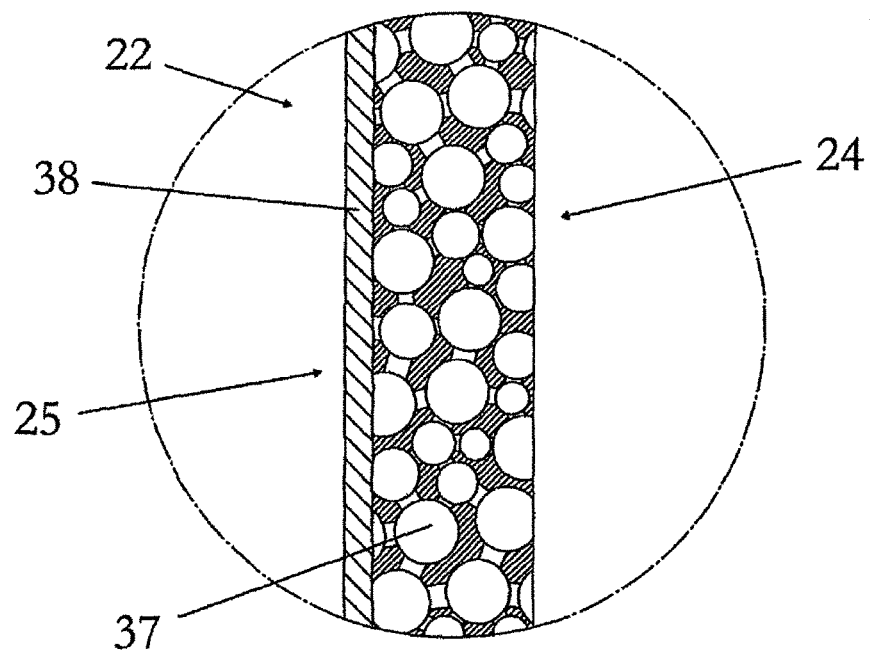
Fig. 15a
Fig. 15b
Fig. 15c

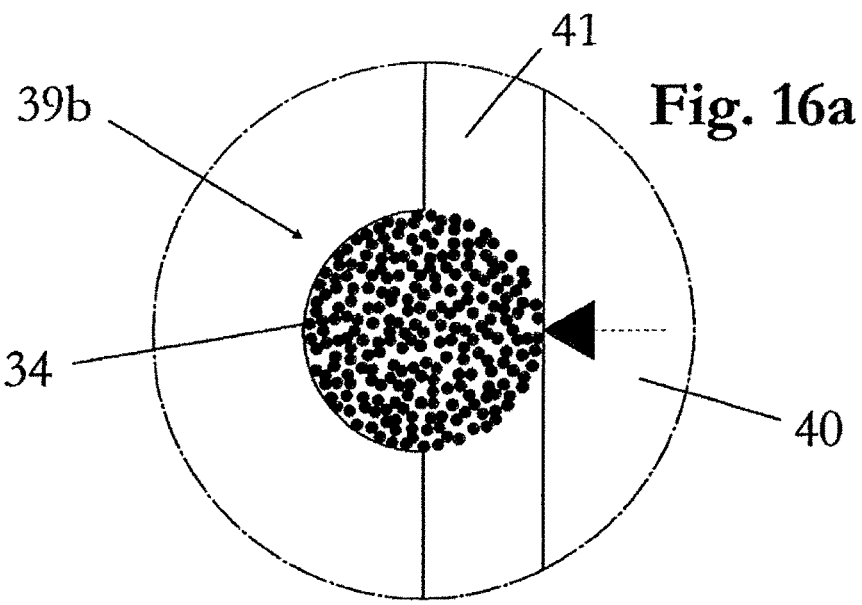
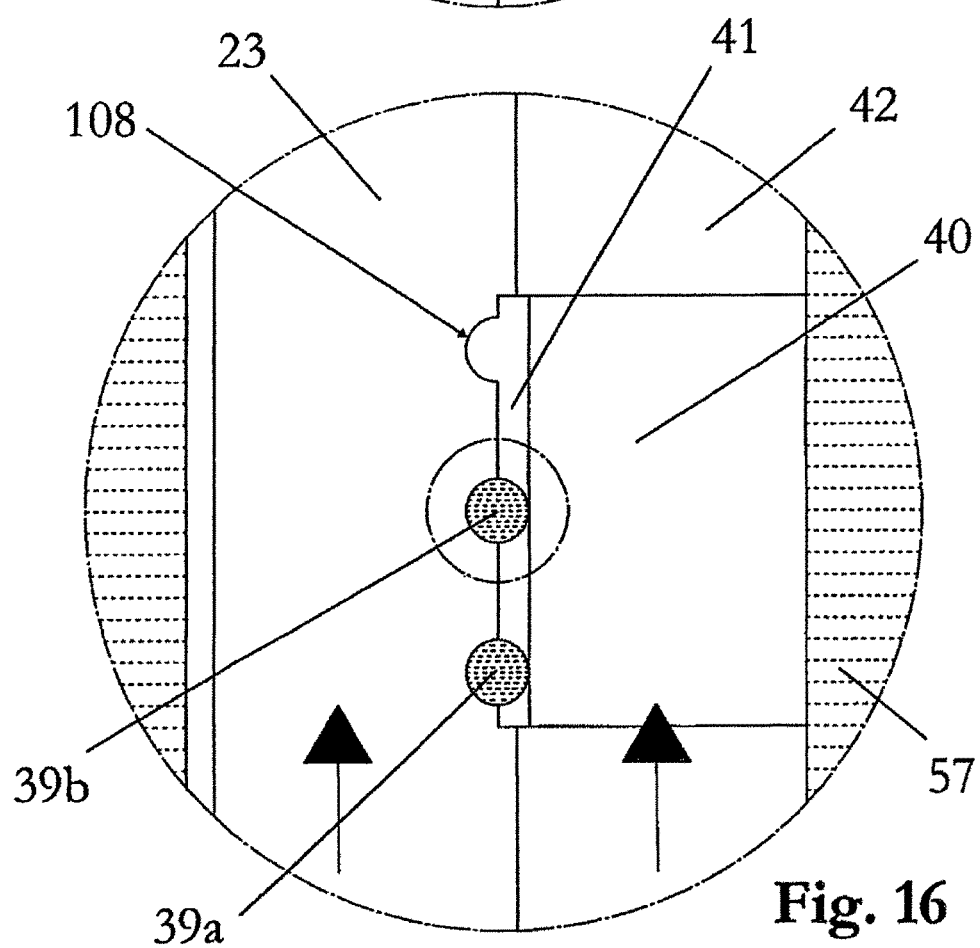

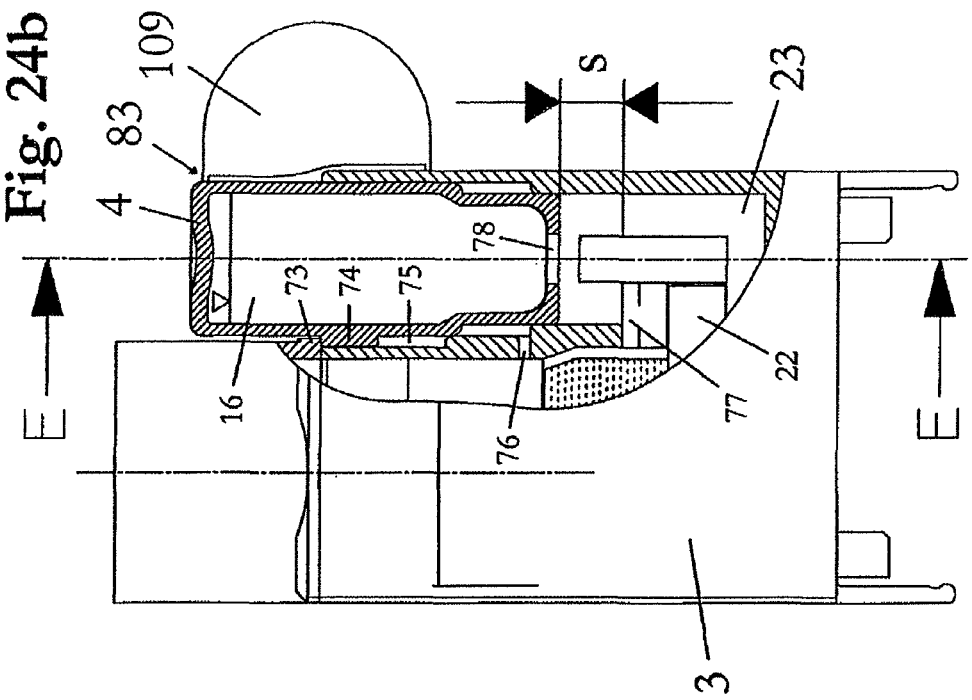
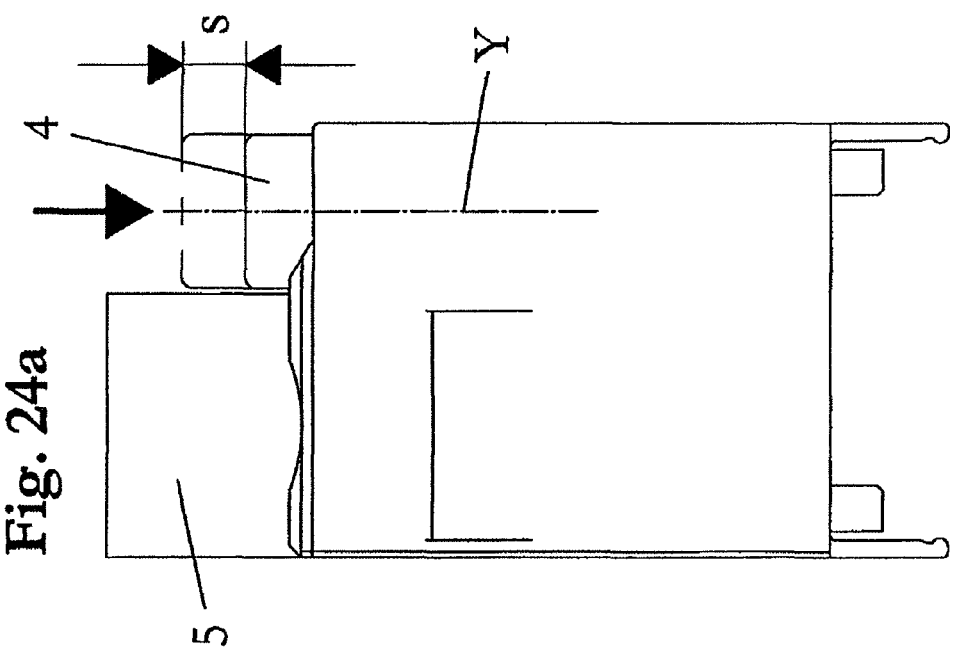

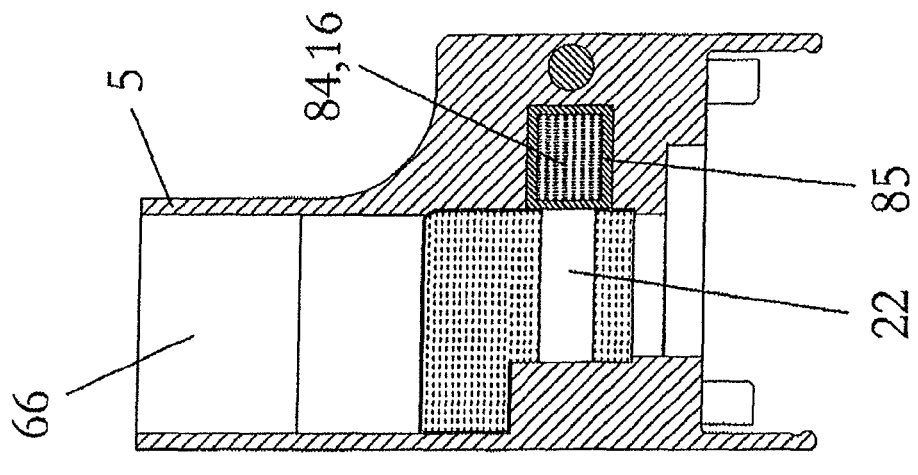
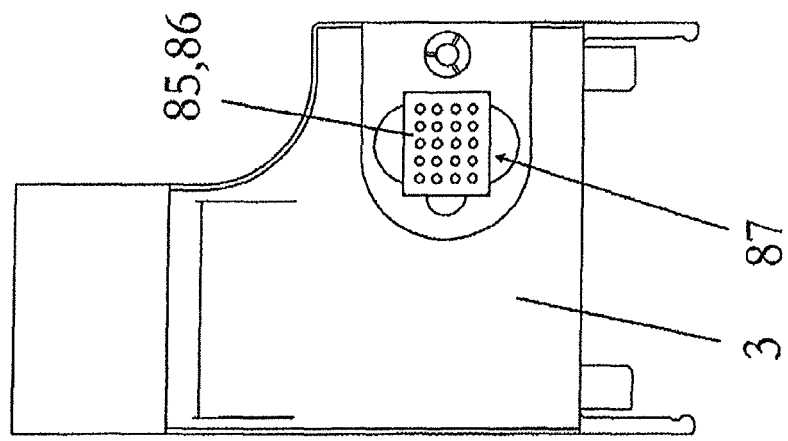
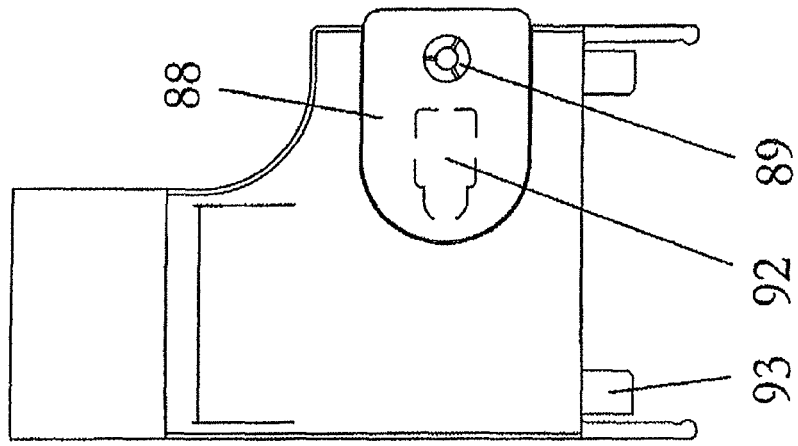

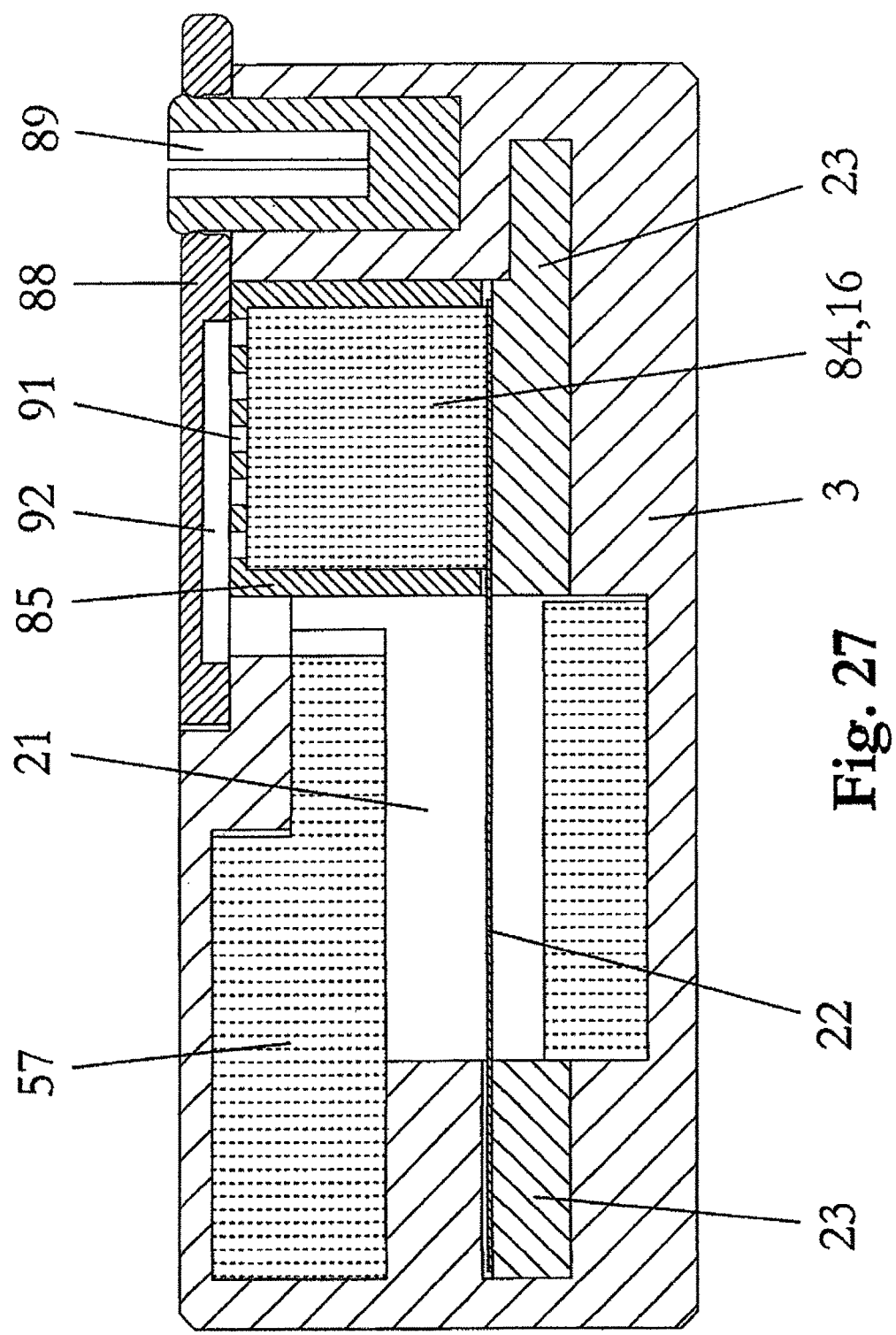

INHALER

CROSS REFERENCE TO RELATED APPLICATIONS

The present application is a continuation of U.S. patent application Ser. No. 13/125,343, filed Apr. 21, 2011, which is a 35 U.S.C. § 371 National Phase conversion of PCT/AT2009/000414, filed Oct. 21, 2009, which claims benefit of Austrian Application No. A 1660/2008, filed Oct. 23, 2008 and Austrian Application No. A 597/2009, filed Apr. 17, 2009, the contents of which are incorporated in full herein by reference.

The invention relates to an inhalator component for the intermittent formation, synchronous with inhalation or drawing, of a vapor-air mixture or/and condensation aerosol, comprising:

a housing;

a chamber arranged in the housing; an air admission opening for the supply of air from the surroundings to the chamber; an electric heating element for evaporating a portion of a liquid material, wherein the vapor which is formed is mixed in the chamber with the air supplied through the air admission opening, and the vapor-air mixture or/and condensation aerosol is formed; and a wick with a capillary structure, which wick forms a composite with the heating element and automatically resupplies the heating element with the liquid material following evaporation.

The invention concerns inhalators which permit intermittent operation synchronous with inhalation or drawing. An operating mode of this type is present if the liquid material is heated and evaporated only during drawing or during inhalation. The heating element is largely deactivated in intervals between two drawings or inhalations. The heating element is activated or energized generally right at the beginning of drawing or inhalation, either manually, for example by means of a switch, but preferably automatically via a suitable sensor and an electronic switching circuit. In the latter case, inhalation—or drawing-activated operation of the inhalator is also referred to.

In the present patent application, the term "inhalator" refers to medicinal and nonmedicinal inhalators. The term furthermore refers to inhalators for administering drugs and substances which are not declared as drugs. The term also refers to smoking articles and cigarette replacement articles, as contained, for example, in European patent class A24F47/00B, in so far as said articles are intended to administer the vapor-air mixture or/and condensation aerosol to the user. The term "inhalator" is also not intended to impose any restrictions on how the vapor-air mixture formed or/and condensation aerosol is supplied to the user or to the user's body. The vapor-air mixture or/and condensation aerosol may be inhaled into the lungs or else also only supplied to the mouth cavity—without inhalation into the lungs. Finally, the term "inhalator" includes both apparatuses which permit direct inhalation into the lungs in a single step ("classic inhalators") and apparatuses which—as in the case of a cigarette—require at least two steps, namely first of all drawing into the mouth cavity (drawing volume: approx. 20-80 mL) and—after putting the inhalator down—a following inhalation into the lungs ("drawing inhalators"). In comparison to drawing inhalators, classic inhalators have a significantly higher air throughput through the inhalator: approx. 100-750 mL/s in comparison to 10-40 mL/s. By contrast, drawing inhalators generally have a significantly higher flow resistance or drawing resistance than classic inhalators.

Definition of Terms

Evaporation energy: sensitive plus latent quantity of heat which is transmitted to the liquid material actually evaporating.

Evaporative capacity: evaporation energy converted per unit of time.

Specific evaporative capacity: evaporative capacity related to the unit of mass of the evaporating liquid material.

Evaporator efficiency: quotient of the evaporation energy and energy produced by the heating element.

Over the years, a multiplicity of inhalators and electric smoking articles has been proposed, said inhalators and smoking articles using electric energy in order to evaporate drugs and/or aroma substances and providing the vapor produced or/and the condensation aerosol formed to a user, optionally for inhalation.

GB 25,575 A.D.1911 (Elwin Kendal Hill) describes an inhalator with an electric evaporator for evaporating medicaments. The apparatus consists of a disk 38 and of a perforated covering 39. An absorption material 40 absorbing the medicament and an electric heating element 41—for example in the form of a resistance heating wire—are located in the space between the disk 38 and the covering 39. The liquid medicament is automatically supplied to the absorption material 40 and the heating element 41 from a supply container 30 via a corresponding number of wicks 45. The air sucked up during inhalation flows through a conical channel 36, as a result of which the stream of air is focused at the evaporator and thereby absorbs the evaporated medicament. The evaporator disk 38 is kept in position by means of spacer sleeves 44.

The particular disadvantages of said arrangement include the complicated construction of the evaporator, the mounting thereof and the connection of the wick to the evaporator. The multipart nature and complex structure of said construction makes the inhalator expensive to produce and makes assembly complicated.

A serious disadvantage is that the ratio of the vapor outlet surface to the evaporator volume is relatively small. This is firstly because of the specific geometry of the evaporator and is secondly caused by the absorption material 40 and the electric heating element 41 being substantially covered, specifically by the disk 38 and the covering 39. Said coverings are required by the construction in order to keep the absorption material 40 and the electric heating element 41 together. It is possible for the vapor formed in the interior of the evaporator to escape exclusively through the holes in the covering 39. As a result, even when the evaporative capacity in the evaporator is comparatively moderate, a boiling crisis may occur, and therefore said arrangement appears unsuitable for intermittent operation synchronous with inhalation or drawing, said operation basically requiring a higher specific evaporative capacity with simultaneously high evaporator efficiency.

A further disadvantage is that, despite the precautions which have been taken against the liquid medicament escaping from the supply container 30, such an escape cannot be entirely prevented by the construction, in particular if the supply container 30 is overfilled, for example due to erroneous operation. Finally, the fact that the liquid medicament in the supply container 30 is virtually freely exposed to the ambient air, which may lead to oxidation of the medicament or/and to a change in the composition thereof due to vaporization effects, should be viewed critically.

U.S. Pat. No. 2,057,353 (Clinton L. Whittemore) describes an evaporator unit for a therapeutic apparatus, consisting of a vessel A for receiving a liquid medicament x, electric conductors 1 and 2 protruding into the vessel through the vessel base, a heating wire 3 which is connected to the electric conductors, and a wick D around which the heating wire 3 is coiled and which extends from said heating wire to the vessel base. The vessel has an air admission opening 4 and a vapor outlet opening 5 which are both curved inward in order to avoid the medicament escaping from the vessel.

A disadvantage of this construction is the complicated process of producing the connection between the heating element and the wick. The heating wire has to be coiled around the wick prior to the composite. Said procedure proves complicated in particular because the parts which are to be joined together are customarily of extremely small dimensions. In addition, it is difficult to ensure that the heating wire coils all bear against the wick. Local detachment may result in the heating wire overheating in these regions, and the resistance material can age more rapidly. This problem also relates to the regions where the heating wire is connected to the electric conductors 1 and 2.

A further disadvantage involves the outer surface of the wick D being partially covered by the heating element 3 being coiled therearound. In this respect, the coiling constitutes an obstacle to the vapor emerging from the wick. Said obstruction of the flow of vapor may entail similar consequences as have already been described in more detail in the document GB 25,575 A.D.1911. Moreover, the vapor formed, as it flows out, comes at least partially into contact with the hot heating wire, which may result in thermal decomposition of the medicament X.

Another disadvantage is that the wick D is held in position merely by the relatively thin heating wire 3. Even a vibration could change the position of the wick D and could considerably change the flow and mixing ratios between the air sucked in through the opening 4 and the vapor flowing out from the wick D and have an adverse effect on the aerosol formation. The apparatus can be operated only in an upright or slightly inclined position; despite the structural measures taken, it is not possible to entirely prevent the medicament x from escaping from the vessel A. Finally, the medicament x in the vessel A is virtually freely exposed to the ambient air; a fact which also has to be considered as being highly unfavorable.

FR 960,469 (M. Eugene Vacheron) describes an inhalation apparatus with an electric evaporator. The inhalation apparatus comprises an electric heating cartridge 4, 5, 6 and a wick 16, which wick is impregnated with the liquid stored in the container 1. The heating cartridge is located outside the container 1, i.e. is not connected directly to the wick. The special structural conditions make the inhalation apparatus sluggish in terms of heating and the latter appears suitable at most for continuous operation of the evaporator; intermittent operation synchronous with inhalation or drawing does not appear to be able to be realized.

CA 2,309,376 (Matsuyama Futoshi) describes an evaporator or atomizer for medicinal applications, consisting of (FIGS. 3A-3C) a vessel 1 containing a liquid composition and a rod-shaped, porous material 3 which is installed in the vessel 1. The rod-shaped, porous material 3 dips at one end into the liquid composition while the other end extends freely upward outside the vessel 1. The vessel 1 and the rod-shaped, porous material 3 are arranged in a curved container 5. The curved container 5 firstly keeps the vessel in position and secondly contains an electric heating device 6 which encases an upper end section of the rod-shaped, porous material 3 at a distance, the distance preferably being within the range of 0.8-2.5 mm. The capillary forces in the rod-shaped, porous material 3 cause the liquid composition to be sucked upward where the composition is finally evaporated by the electric heating device 6. In this case, the active compounds contained in the liquid composition are atomized and pass out of the curved container 5 through the opening 9 into the space such that they can be inhaled by the user. The liquid composition consists of an aqueous solution in which an active compound concentrate is dissolved or dispersed. The aqueous solution preferably consists of water or of a mixture of water and ethanol. The active compound concentrate is obtained from the leaves of *Lagerstroemia Speciosa*, and contains up to 15% by mass of corosolic acid. The active compound concentrate supposedly acts in a manner reducing blood sugar. The portion of active compound concentrate (calculated in the form of corosolic acid) in the aqueous solution is 0.5-3.0% by mass.

The evaporator is designed for continuous operation. The electric heating device 6 is arranged at a distance from the porous material 3 and consequently does not form a composite therewith. The gap in between constitutes a high resistance to heat conduction. Intermittent operation with a correspondingly high specific evaporative capacity would be realized only if the heat were transmitted by means of heat radiation. For this purpose, the electric heating device 6 would need to be heated up suddenly to a very high temperature. The liquid composition would primarily evaporate in the border zone facing the heating device and would flow through the gap already mentioned into the surroundings. Irrespective of the implementation of said concept in practice, the vapor formed would in any case come into contact with the glowing surface of the heating device 6, as a result of which the active compound concentrate would be at least partially thermally decomposed.

U.S. Pat. No. 6,155,268 (Manabu Takeuchi) describes an aroma-generating apparatus consisting of (FIG. 1A) a chamber 121 with an air admission 18 and a mouthpiece opening 22 and mouthpiece 16, thus forming a gas passage channel 20, and furthermore comprises a liquid container 32 for receiving a liquid aroma substance 34, and finally a capillary tube 36 with a first end section which dips into the liquid in the container 32, and with a second end section which communicates with the gas passage channel 20, and furthermore comprises a heating element 42. The liquid aroma substance 34 flows by means of the capillary forces acting in the capillary tube 36 to the heating element 42 where said substance is evaporated and flows as a stream of vapor out of the opening 36b into the gas passage channel 20. The stream of air entering from the outside into the chamber 121 through the air admission 18 is focused by the apertured diaphragm 24, 24a at the capillary opening 36b, as a result of which favorable conditions for intimate mixing between the vapor and sucked-up air and for the formation of an aerosol are intended to be provided.

In alternative embodiments (FIGS. 8-13), plate-like heating elements are proposed. In further exemplary embodiments (FIGS. 14 and 15), the interior of the capillary tube is filled with a pore structure 302 which, in one variant embodiment, can also protrude out of the capillary tube, wherein, in said latter case, the heating element 425 can be arranged at the end of the protruding pore structure.

The disadvantage again of said arrangements is the relatively complicated construction of the evaporator unit—in this case consisting of the capillary tube and the heating element. Said two microcomponents have to be connected to each other, and the heating element has to be connected to the electric supply, which, in the specific case, can probably be realized only via electric wires. Unfortunately, this document does not provide more precise instructions in this regard.

For the arrangements according to FIGS. 14 and 15, the same applies as has already been explained with regard to GB 25,575 A.D.1911: the ratio of the vapor outlet surface to the evaporator volume is extremely small. This is because the pore structure 302 is substantially covered by the encasing 301 and the heating element 425. As a result, even at a moderate evaporative capacity, a boiling crisis may occur, and therefore the functioning of said arrangements should basically be doubted, particularly if intermittent operation synchronous with inhalation or drawing is required.

Two variant embodiments are proposed for the liquid container 32: in a first variant embodiment (FIG. 1A), the liquid container is a specified part of the aroma-generating apparatus. The liquid container can be refilled via a filling opening. However, such a refilling involves risks for the environment, in particular if the liquid aroma substance contains drugs or poisons, such as, for example, nicotine, and the refilling is carried out by the user him/herself. In an alternative variant embodiment (FIG. 8), the liquid container is designed as a small interchangeable container. Details regarding the coupling up of said container have not been disclosed. Small interchangeable containers always involve the risk of being swallowed by small children, which may have a potentially lethal outcome, in particular if the liquid aroma substance contains drugs or poisons, such as, for example, nicotine.

The arrangement according to FIG. 8 furthermore shows an exchangeable mouthpiece 161 with a hollow-cylindrical extension which lines a large part of the chamber 121 and extends virtually as far as the mouth of the capillaries 371. Condensate residues arising in the chamber 121 accumulate primarily on the inner surface of the hollow-cylindrical extension and can be removed together with the mouthpiece. A problem is that the inner surface is capable only to a limited extent of receiving condensate. In particular if the liquid aroma substance contains relatively large portions of low-boiling fractions with a high vapor pressure—for example ethanol or/and water, the mouthpiece has to be exchanged within short intervals. Also, drops are formed on the inner surface of the mouthpiece under the influence of surface tensions, the drops steadily increasing in volume until the adhesion forces are ultimately no longer sufficient in order to hold the drops, and the latter combine to form relatively large accumulations of liquid. Said accumulations of liquid may have an adverse effect on the functioning of the apparatus but may also constitute a risk for the user and the environment if said accumulations contain drug residues or poisons, such as, for example, nicotine. However, even the option of the user him/herself being able to remove the condensate from the apparatus involves a risk for the environment.

U.S. Pat. Nos. 4,922,901, 4,947,874 and 4,947,875 (Johny L. Brooks et al.) describe articles for releasing and administering drugs or/and aromas using an exchangeable unit 12 which contains an electric resistance heating element 18, the surface of which is larger than at least 1 mA2/g; the electric resistance heating element 18 carries aerosol-forming substances. The electric resistance heating element 18 preferably consists of a porous or fibrous material—for example carbon fibers, which material is impregnated with a liquid aerosol former. The articles furthermore contain a drawing-activated electronic control unit 14 for controlling the stream through the electric resistance heating element 18 and are capable of administering at least 0.8 mg of aerosol or drug per drawing, with at least 10 drawings being possible in total before the exchangeable unit 12 together with the resistance heating element 18 has to be replaced by a new one.

In this article, the entire liquid material to be evaporated is therefore already pre-stored in the resistance heating element 18. A supply of liquid via a wick is not provided. This also results in the following disadvantages: the aerosol-forming substances or the drug or/and any added aroma substances which are released, for example, during the final drawing have already been repeatedly heated up beforehand, which circumstance prompts thermal decomposition of the aerosol-forming substances. In addition, said preceding heating operations are unfavorable in so far as additional electric energy is required for this purpose, said energy not making any contribution to the actual evaporation and aerosol formation. This results in a very low evaporator efficiency. A further disadvantage is that, in the case of mixtures of various aerosol-forming substances, drugs and aroma substances, with different boiling points of the individual substances, the chemical composition of the aerosol formed and the organoleptic and pharmacological effect thereof varies from one inhalation to the next, with low-boiling fractions increasingly being evaporated during the first drawings, and higher boiling substances increasingly being released during the final drawings. Finally, the exchangeable unit 12 which is relatively complicated to produce, and therefore also the heating element 18, has to be replaced after just approximately 10 drawings, which makes the use of said articles expensive.

U.S. Pat. Nos. 5,060,671 and 5,095,921 (Mary E. Counts, D. Bruce Losee et al.) describe an article 30 (FIG. 4) in which an aroma-releasing medium 111 is heated by electric heating elements 110 in order to provide inhalable aromas in vapor or aerosol form. The article contains a plurality of charges of the aroma-releasing medium 111, which charges are heated sequentially and thereby provide individual drawings. The plurality of charges of aroma-releasing medium 111 are applied to the heating elements 110 preferably in the form of a covering, coating or a thin film and may also contain aerosol-forming substances. The adhesion of the aroma-releasing medium 111 to the heating elements 110 can be improved by an adhesion-promoting agent, for example pectin. The electric heating elements 110 and the charges of aroma-releasing medium 111 applied to said heating elements are preferably arranged in an exchangeable unit 11 which is connected to a reusable unit 31 via electric contact pins. The reusable unit 31 contains an electric energy source 121 and an electronic control circuit 32. U.S. Pat. No. 5,322,075 (Seetharama C. Deevi et al.) describes a similar article.

Although said article eliminates some of the disadvantages of the previously described articles (U.S. Pat. Nos. 4,922,901, 4,947,874 and 4,947,875), the construction of the exchangeable unit 11 appears to be even more complex, since, in the specific case, a multiplicity of heating elements is provided together with electric contact connection means. If it is furthermore taken into consideration that the complex, exchangeable unit 11 scarcely permits more than 15 drawings (cf. FIGS. 7A-7K), it is clear that the use of such an article would be expensive. Furthermore, in the specific case, the aroma-releasing medium 111 is present in the form of a relatively large thin layer which, particularly during storage of the exchangeable unit 11, is exposed to diverse environmental influences (oxidation, etc.). In order to avoid said influences, a complicated packaging which protects the medium 111 from the environment but does not as far as possible touch the medium would have to be provided. U.S. Pat. Nos. 5,060,671 and 5,095,921 do not discuss this aspect.

US 2005/0268911 (Steven D. Cross et al.) is very similar to the previously described article according to U.S. Pat. Nos. 5,060,671 and 5,095,921 and describes an apparatus for producing and dispensing a plurality of doses of a condensation aerosol for the inhalation of high purity medicaments and, in the simplest case (FIG. 1A), consists of an air duct 10 with an inlet and an outlet, a plurality of supports 28 which are arranged in the air duct and each bear a certain dose of a substance/medicament, and a device for evaporating said discrete doses. The stream of air flowing in through the inlet is conducted to the supports 28 where the condensation aerosol is finally formed. The supports 28 each contain an electric resistance heating element—preferably consisting of a metal foil 78 of stainless steel. The metal foil heating elements 78 are preferably mounted on a printed circuit board (FIG. 4). The disadvantages of the article according to U.S. Pat. Nos. 5,060,671 and 5,095,921 apply equally to the apparatus according to US 2005/0268911.

U.S. Pat. Nos. 5,505,214 and 5,865,185 (Alfred L. Collins et al.) describe electric smoking articles consisting of (FIG. 4; U.S. Pat. No. 5,505,214) an exchangeable unit 21 and a reusable part 20. The exchangeable unit 21 contains tobacco aromas 27 which are located on a support 36. The reusable part 20 contains a plurality of heating elements 23 which are supplied with current or energy by an electric energy source—for example a rechargeable battery—via an electric control circuit. After the exchangeable unit 21 is inserted into the reusable part 20, the support 36 comes to lie on the heating elements 23. During inhalation or drawing, one individual heating element is activated in each case by the control circuit, as a result of which the support 36 is partially heated and the tobacco aromas 27 are evaporated and released, optionally in the form of an aerosol. In the exemplary embodiment according to FIG. 4, the reusable part 20 has eight heating elements 23, with eight inhalations or drawings being possible similarly to a cigarette. The exchangeable unit 21 then has to be replaced by a new unit.

The smoking articles according to U.S. Pat. Nos. 5,505, 214 and 5,865,185 have the advantage over the article according to U.S. Pat. Nos. 5,060,671 and 5,095,921 that the heating elements 23 are arranged in a stationary manner in the reusable part 20 and can therefore be used more than once. Electric contacts between the exchangeable unit 21 and the reusable part 20 are not required. However, a disadvantage over the article according to U.S. Pat. Nos. 5,060,671 and 5,095,921 is that the support 36 has to be heated in addition to the heating elements 23; the heat required for this lowers the evaporator efficiency. The other disadvantages, already explained earlier, of the article according to U.S. Pat. Nos. 5,060,671 and 5,095,921 are accordingly applicable.

U.S. Pat. No. 4,735,217 (Donald L. Gerth et al.) describes a metering unit for administering evaporated medicaments in the form of fine aerosol particles which pass into the lungs by inhalation. In one exemplary embodiment (FIGS. 4 and 5), the metering unit consists of a film-like NICHROME® heating element segment 72 (length×width×thickness: 1×1/8.times.0.001 inch) which is connected in series to a battery 65 and a switch 60, 69 activated by a stream of air or by drawing. The medicament to be evaporated—for example nicotine—is present in the form of a solid pellet 40 which makes contact with the heating element 72. As an alternative, the medicament to be evaporated can be applied directly to the heating element surface in the form of a coating or a film.

Some of the disadvantages of this metering unit have already been mentioned in U.S. Pat. No. 4,922,901. Added thereto is the fact that the transfer of heat from the heating element to the pellet turns out to be highly unfavorable. A large part of the heating element 72 is heated up without a purpose, since only a small part of the heat formed in peripheral regions of the heating element can be used for the pellet. In principle, it is disadvantageous that, in order to form the pellet, use is made of solids which generally have to be melted first before they can be evaporated, thus causing a further deterioration in the energy balance.

EP 1,736,065 (Hon Lik) describes an "electronic cigarette" for atomizing a solution of nicotine and essentially consists of a container 11 for receiving the liquid to be atomized, and an atomizer 9. An atomizer chamber 10 formed by the atomizer chamber wall 25 is located in the interior of the atomizer 9. An electric heating element 26, for example in the form of a resistance heating wire or a PTC ceramic, is arranged within the atomizer chamber 10. Furthermore, ejection holes 24, 30 pointing in the direction of the heating element 26 are provided in the atomizer or in the atomizer wall 25. The container 11 contains a porous body 28—for example composed of synthetic fibers or foam, which is impregnated with the liquid to be atomized. The atomizer chamber wall 25 is likewise surrounded by a porous body 27—for example consisting of nickel foam or of a metal felt. The porous body 27 is in contact with the porous body 28 via a bulge 36. Capillary forces have the effect that the porous body 27, which at the same time forms the outer casing of the atomizer 9, is infiltrated by the liquid to be atomized. The atomizer furthermore comprises a piezoelectric element 23.

The "electronic cigarette" is operated in a manner activated by drawing. During drawing, a negative pressure arises in the atomizer chamber 10, since the latter is connected to the mouthpiece 15. As a result, air flows out of the surroundings via the ejection holes 24, 30 into the atomizer chamber. The high flow velocity in the ejection holes 24, 30 has the effect that liquid is sucked out of the porous body 27 and is entrained by the stream of air in the form of drops (Venturi effect). The nicotine-containing liquid passes into the atomizer chamber 10 where the liquid is atomized by ultrasound by means of the piezoelectric element 23. The heating element 26 is intended to bring about additional atomization or evaporation of the solution of nicotine. In an alternative variant embodiment, the atomization takes place exclusively by means of the heating element 26.

The arrangement has functional similarities to the smoking apparatus disclosed in U.S. Pat. No. 4,848,374 (Brian C. Chard et al.). It is disadvantageous in both cases that, similarly as with a cigarette, the metering of the liquid to be atomized and of the aerosol formed depends on the particular drawing profile of the user. However, this is undesirable for medicinal or therapeutic applications. Added to this is the fact that the atomization by means of ultrasound generally produces significantly larger aerosol particles than condensation aerosols customarily have. Said larger particle fractions do not pass into the pulmonary alveoli but rather are already absorbed in lung sections located upstream, which, in the case of drugs acting systemically, such as nicotine, has a highly unfavorable effect on the absorption kinetics and the efficiency of supply of the active compound. Furthermore, in particular in the case of the alternative variant embodiment without ultrasound atomization, it has to be doubted whether the electric heating element, which is designed in a manner similar to an incandescent bulb wire, is even capable of transmitting the heating energy required during drawing for the evaporation to the liquid material. This would probably be possible only by heat radiation, for which purpose the heating element would have to be brought proverbially to a glowing temperature. Such high temperatures are basically associated with various risks and disadvantages—including with the risk of thermal decomposition of the liquid to be atomized or already atomized. Finally, it should be considered to be a high safety risk that the container containing the highly poisonous solution of nicotine is open on an end side and furthermore can be detached from the "electric cigarette". This risk has already been identified, and in a development—as in DE 202006013439U—has been partially neutralized by the container being formed by a hermetically sealed cartridge, but the cartridge can disadvantageously still always be detached from the "electric cigarette" and can be swallowed, for example by small children.

Finally, it should be noted that some of the documents just depicted have been described, although they are not included in the generic type of the invention referred to at the beginning, since they at least depict the further prior art and in this respect are worthy of being taken into consideration.

The invention is based on the object of eliminating the disadvantages shown above of the arrangements known from the prior art. The invention is based in particular on the object of designing an inhalator component of the type described at the beginning such that the high specific evaporative capacity required for intermittent operation synchronous with inhalation or drawing can be realized with simultaneously high evaporator efficiency. The power and energy requirement required should be able to be covered here by an energy store approximately in the format of an average cell phone battery. The occurrence of a boiling crisis in the wick is intended to be avoided, and the liquid material is intended to be able to be evaporated as gently as possible, i.e. without substantial thermal decomposition.

The inhalator component is furthermore intended to permit user-friendly and safe operation, and is intended to be able to be produced as cost-effectively as possible, which specifically means: the composite is intended to be infiltrated as rapidly as possible by the liquid material such that substantial waiting times do not have to be maintained between two inhalations or drawings. The inhalator component is intended to be able to be operated independently of position. The risk of liquid material—including liquid condensate residues—passing into the environment or impairing the functioning of the inhalator component is intended to be minimized. The composite is intended to be able to be produced as cost-effectively as possible. The inhalator component is intended to be configured to be handy and ergonomic and to be simple to operate.

Furthermore, the properties of the vapor-air mixture formed or/and condensation aerosol are intended to be able to be influenced at least within certain limits—in particular the particle size distribution of the condensation aerosol formed and the organoleptic effects thereof.

Finally, the inhalator component is intended to be designed in two basically different variant embodiments such that it can be used both in classic inhalators and in drawing inhalators.

The object is achieved in that the composite is of planar design, and at least one heated section of the composite is arranged in the chamber in a contact-free manner, and the capillary structure of the wick in said section is substantially exposed at least on one side of the planar composite. In a development of the invention, the capillary structure of the wick in said section is substantially exposed on both sides of the planar composite. Owing to the fact that the capillary structure of the wick in said section is substantially exposed, the vapor formed can flow unhindered out of the wick, as a result of which the evaporative capacity can be increased and a boiling crisis in the wick can be avoided.

Explanations of Terms

"Planar composite" means that the heating element and the wick are arranged in the same surface or/and in mutually parallel surfaces and are connected to each other, the same surface or/and the mutually parallel surfaces comprising at least one planar surface or area, at least one curved surface or area, or a combination of at least one planar surface or area and at least one curved surface or area. The capillary transport of the liquid material in the planar composite takes place primarily in the surface direction. "In a contact-free manner" means that neither the chamber wall nor other structural elements of the inhalator component are touched; the effect achieved by the contact-free arrangement in the chamber is that the heat conduction losses of the composite are substantially reduced in said section, and the composite is heated until the liquid material stored in the wick can evaporate.

"Chamber" is intended also to include channels; therefore, even a tubular channel is included in the term "chamber"; in this case, an open tube end could form, for example, the air admission opening.

In a preferred refinement, the planar composite has a thickness of less than 0.6 mm, and, in a particularly preferred refinement, a thickness of less than 0.3 mm. The result of this dimensioning is that the heat which is introduced in a planar manner can flow in efficiently by means of heat conduction—i.e. at a low temperature gradient, to the exposed wick surface or capillary structure where said heat causes the evaporation of the liquid material. In addition, vapor already formed in the interior of the wick can more easily reach the exposed wick surface. These conditions permit a further increase in the evaporative capacity and contribute to the liquid material being evaporated particularly gently. It should be noted that this does not merely involve simple dimensioning but rather an essential feature of the invention. Even the inventor was surprised to find in experiments that planar wicks with an exposed wick surface and a thickness <300 μm still exhibit a wicking effect in the surface direction.

It is considered as being according to the invention that the composite is designed in the form of a plate, film, strip or band. Said planar arrangements make it possible to use production methods permitting particularly economic mass production.

According to the invention, the planar composite contains one of the following structures: a fabric, open-pored fiber structure, open-pored sintered structure, open-pored foam or open-pored deposition structure. Said structures are suitable in particular for providing a wick body with a high degree of porosity. A high degree of porosity ensures that the heat produced by the heating element is used for the most part for evaporating the liquid material located in the pores, and high evaporator efficiency can be obtained. Specifically, a porosity of greater than 50% can be realized with said structures. The open-pored fiber structure can consist, for example, of a nonwoven fabric which can be arbitrarily compacted, and can additionally be sintered in order to improve the cohesion. The open-pored sintered structure can consist, for example, of a granular, fibrous or flocculent sintered composite produced by a film casting process. The open-pored deposition structure can be produced, for example, by a CVD process, PVD process or by flame spraying. Open-pored foams are in principle commercially available and are also obtainable in a thin, fine-pored design.

In one variant embodiment of the invention, the planar composite has at least two layers, wherein the layers contain at least one of the following structures: a plate, foil, paper, fabric, open-pored fiber structure, open-pored sintered structure, open-pored foam or open-pored deposition structure. In this case, certain layers can be assigned to the heating element, and other layers to the wick. For example, the heating element can be formed by an electric heating resistor consisting of a metal foil. However, it is also possible for one layer to take on both heating element and wick functions; such a layer may consist of a metal wire fabric which, firstly, because of the electric resistance thereof, makes a contribution to the heating, and, secondly, exerts a capillary effect on the liquid material. The individual layers are advantageously but not necessarily connected to one another by a heat treatment, such as sintering or welding. For example, the composite can be designed as a sintered composite consisting of a stainless steel foil and one or more layers of a stainless steel wire fabric (material, for example AISI 304 or AISI 316). Instead of stainless steel, use may also be made, by way of example, of heating conductor alloys—in particular NiCr alloys and CrFeAl alloys ("KANTHAL®") which have an even higher specific electric resistance than stainless steel. The material connection between the layers is obtained by the heat treatment, as a result of which the layers maintain contact with one another—even under adverse conditions, for example during heating by the heating element and resultantly induced thermal expansions. If the contact between the layers is lost, a gap could form which, firstly, could interfere with the coupling in terms of capillary action and, secondly, the transmission of heat from the heating element to the liquid material.

In an analogous refinement of the invention, it is provided that the composite is of linear design, and at least one heated section of the composite is arranged in the chamber in a contact-free manner, and the capillary structure of the wick in said section is substantially exposed. Owing to the fact that the capillary structure of the wick in said section is exposed, the vapor formed can flow unhindered out of the wick, thus enabling the evaporative capacity to be increased and a boiling crisis in the wick to be avoided. The liquid material is transported in terms of capillary action in the linear composite primarily in the longitudinal direction of the linear composite. The terms "in a contact-free manner" and "chamber" have already been explained earlier.

The linear composite preferably has a thickness of less than 1.0 mm, wherein the thickness is defined by: $\sqrt{4*A/\pi}$ (A refers to the cross-sectional area of the composite). This dimensioning has the result that the heat introduced linearly can flow efficiently by means of heat conduction—i.e. at a low temperature gradient—to the exposed wick surface where it causes evaporation of the liquid material. In addition, vapor already formed in the interior of the wick can more easily reach the exposed wick surface. These conditions permit a further increase in the evaporative capacity.

According to the invention, the linear composite contains at least one of the following structures: wire, yarn, an open-pored sintered structure, open-pored foam or open-pored deposition structure. Said structures are suitable in particular for providing a linear composite with sufficient mechanical stability and a high degree of porosity.

In a preferred refinement of the planar or linear composite, the heating element is at least partially integrated in the wick. This arrangement has the advantageous effect that the heat is produced and released directly in the wick body and is transmitted there directly to the liquid material to be evaporated. The heating element can consist, for example, of an electrically conductive thin layer of platinum, nickel, molybdenum, tungsten or tantalum, said thin layer being applied to the wick surface by a PVD or CVD process. In this case, the wick consists of an electrically non-conductive material—for example of quartz glass. In a simpler refinement of the invention in terms of production, the wick itself at least partially consists of an electric resistance material, for example of carbon, of an electrically conductive or semi-conductive ceramic or of a PTC material. It is particularly favorable if the electric resistance material is metallic. Metals have greater ductility than the previously mentioned materials. This property has proven advantageous in so far as the composite is exposed during operation to a thermal alternating load, thus causing the induction of thermal expansions. Metals can better compensate for such thermal expansions. Furthermore, metals have a higher impact toughness by comparison. This property has proven an advantage whenever the inhalator component is exposed to impacts. Examples of suitable metallic resistance materials include: stainless steels, such as AISI 304 or AISI 316, and heating conductor alloys—in particular NiCr alloys and CrFeAl alloys ("KANTHAL®"), such as DIN material number 2,4658, 2,4867, 2,4869, 2,4872, 1,4843, 1,4860, 1,4725, 1,4765 and 1,4767.

In a further preferred refinement of the planar or linear composite, it is provided that the connection between the heating element and the wick extends over the entire extent of the wick. In this case, it is insignificant whether the heating element is also used as such, i.e. is heated, over the entire extent thereof, or only partially. This depends on the particular position of the electric contact connection of the heating element. Even if said contact connection takes place at the outer ends of the heating element, the heating element does not inevitably have to contribute over the entire extent thereof to evaporating the liquid material. Sections of the heating element can thus touch structural components which substantially dissipate the heat produced in the heating element, and therefore the liquid material in the wick is virtually not heated at least in said section. However, said outflowing heat would be considered in the energy balance as a loss. This refinement makes it possible to use production processes which provide significant cost advantages over the prior art and for the first time make mass production economical. The planar composite can thus be obtained by large scale manufacture from a planar multiple panel by the composite being detached from said multiple panel by means of suitable separating processes, such as punching or laser cutting. The linear composite can advantageously be obtained from an endless material. The term "endless material" also includes a material having a finite length if said length is much larger than the length of the linear composite.

As has already been explained earlier, a high degree of porosity of the wick and of the composite is desirable with regard to effective use of the heat energy introduced by the heating element. The porosity can additionally be increased by the composite or the preliminary production stage thereof—for example the multiple panel—being etched. By way of example, a sintered composite consisting of a stainless steel foil and one or more layers of a stainless steel mesh (for example AISI 304, AISI 316) can be correspondingly treated in an aqueous etching bath consisting of 50% of azotic acid and 13% of hydrofluoric acid, wherein the electric resistance of the heating element and/or composite can also be influenced, namely increased, as a side effect.

According to the invention, the surface of the composite or the preliminary production stage thereof can also be activated. This measure also includes cleaning of the surface and brings about better wetting of the composite material by the liquid material and, associated therewith, more rapid infiltration of the wick. For example, for the sintered composite cited previously by way of example and consisting of a stainless steel foil and one or more layers of a stainless steel mesh, treatment in 20% strength phosphoric acid is very readily suitable in order to obtain the previously mentioned effects.

In an advantageous refinement of the invention, the wick is designed as arterial wick. Said type of wick is used in particular in heat exchanger tubes and is described more precisely in the relevant literature—see, for example, ISBN 0080419038. A wick of this type can consist, for example, of a bundle of channels or capillaries—"arteries" which are surrounded by a finer pore structure or are formed by the latter. In comparison to a homogeneous pore structure of identical capillary action or identical capillary pressure (capillary rise), the bundle of channels or capillaries offers a lower flow resistance to the liquid material, thus enabling the infiltration of the wick with the liquid material to be substantially accelerated.

In one variant embodiment, the wick is perforated in the thickness direction. The perforation can take place, for example, by means of laser and has the following effects: firstly, the porosity is further increased; secondly, the flow resistance in the thickness direction is reduced. The latter effect occurs in particular when an arterial wick is used in so far as the liquid material in the wick undergoes an increase in pressure during the evaporation, and the perforation acts as pressure relief. This avoids the vapor formed in the wick from pressing the liquid material back via the arteries to the source of the liquid material, which can severely disturb the supply of liquid material.

It is furthermore considered as being according to the invention that the planer composite is of substantially flat design, and the air admission opening is designed as a slot-shaped channel, and the slot-shaped channel is oriented parallel to the flat composite surface. Analogously, it is considered as being according to the invention that the linear composite is of substantially rectilinear design, and the air admission opening is designed as a slot-shaped channel, and the slot-shaped channel is oriented parallel to the rectilinear composite. By means of these geometrically simple arrangements, very favorable mixing conditions between the inflowing air and the vapor emerging from the wick can be provided, which mixing conditions can furthermore be varied in a simple manner by changing the position of the slot-shaped channel or/and by changing the slot height; it is thereby possible to have a certain influence on the properties of the aerosol formed—in particular on the size of the aerosol particles formed.

According to the invention, the composite passes through the chamber in the manner of a bridge and is mounted by two end sections on two electrically conductive, plate-like contacts, and the heating element is in contact electrically with the contacts. If it is considered that the composite involves an extremely small and mechanically sensitive component which, in addition, is exposed to the flow forces of the air flowing into the chamber and to forces as a consequence of thermal expansion, it is clear that the arrangement just described is a relatively stable and simple to produce anchoring and contact connection of the composite. In a preferred refinement of the invention, the electric contact connection of the heating element consists of a welded or sintered connection. The welded connection can be produced by spot welding, resistance welding, ultrasound welding, laser welding, bonding or other suitable welding processes. It is particularly favorable for the welding or sintering if the plate-like contacts consist of the same or of a similar material as the heating element. In another advantageous refinement of the invention, the electric contact connection of the heating element consists of an adhesive bonding connection by means of an electrically conductive adhesive, for example by means of a silver-containing adhesive on the basis of epoxide. In this case, the plate-like contacts can in principle be produced from any electric contact material as long as the material is compatible with the adhesive used; as an alternative, the plate-like contacts can also be formed by printed circuit boards or by a common printed circuit board. Thick copper printed circuit boards having copper layer thicknesses in the range of 100-500 μm are preferred because of the better heat dissipation. Of course, the invention is not restricted to the previously mentioned contact connection processes. As an alternative, the electric contact connection could also take place by means of mechanical clamping. In a development of the invention, the plate-like contacts protrude out of the outer surface of the housing in the form of two plug contacts. The two plug contacts are provided in order to supply the required electric energy to the heating element.

In a preferred development of the invention, one end of the composite projects into a capillary gap, the flow resistance of which is lower than the flow resistance of the wick. The capillary gap feeds the wick with liquid material; the flow resistance which is reduced in comparison to the wick causes the liquid material to pass more rapidly to the evaporation zone in the composite. As a result, however, the time required to completely infiltrate the wick again with liquid material following evaporation is also reduced. This time corresponds to a waiting time which should be at least maintained between two drawings or inhalations. If said waiting time is not maintained, this may result in a reduction in the emitted quantity of vapor or drug dose. In addition, due to the composite being heated up in some sections without liquid material, local overheating causing damage to the composite or shortening the service life thereof may occur. In a development of the invention, it is provided that the cross section of the capillary gap is greater than the cross section of the composite. This has the effect that the liquid material partially circumvents the wick in the manner of a bypass and thereby passes even more rapidly to the evaporation zone in the composite. In a preferred refinement of the invention, the heating element of the composite is in contact connection electrically in the capillary gap. This results in a highly space-saving arrangement.

A preferred embodiment of the invention relates to an inhalator component with a liquid container which is arranged in the housing or is connected to the housing and contains the liquid material, together with an openable closure; according to the invention, the liquid container can neither be removed from the housing nor separated from the housing, and the liquid material in the liquid container can be coupled in terms of capillary action to the capillary gap by manual opening of the openable closure. The liquid container can therefore not be removed from the inhalator component by the user, even if the liquid material is used up, which can be considered to be an advantage in terms of safety in particular if the container contains drugs or/and poisons, for example, nicotine. The housing of the inhalator component is too large to be swallowed by small children. Refilling of the liquid container is not provided; on the contrary, the inhalator component together with the liquid container forms a disposable article which should be disposed of properly after the liquid material is used up. The liquid material is stored in the liquid container in a hermetically sealed manner. Access of air or UV rays is very substantially prevented. In addition, the liquid container can contain an inert gas, such as argon, nitrogen or carbon dioxide, which additionally protects the liquid material from oxidation. The openable closure of the liquid container is expediently opened only shortly prior to use of the inhalator component, after which the liquid material passes via the capillary gap to the wick and infiltrates the latter. The openable closure is opened in a simple manner manually without the assistance of special aids.

In a first variant embodiment, the liquid container is connected rigidly and permanently to the housing or itself forms part of the housing. The liquid container may be designed, for example, as a separate part which is connected nonseparably to the housing by an adhesive bonding connection or a welded connection. In a development of the first variant embodiment, a reservoir which communicates with the capillary gap, adjoins the liquid container and is separated therefrom by the openable closure is provided. The reservoir serves, when the closure is open, to receive at least some of the liquid material from the liquid container and to ensure the coupling in terms of capillary action to the capillary gap. The openable closure is preferably opened by a pin which is mounted in an axially displaceable manner in the housing and the first end of which is directed toward the openable closure and the second end of which protrudes out of the outer surface of the housing in the manner of an extension when the closure is closed, by a compressive force being exerted on the second end. The compressive force is transmitted by the pin to the openable closure, as a result of which the latter is finally torn open along a predetermined breaking point. The compressive force can be produced, for example, by finger pressure. A particularly advantageous refinement of the invention relates to an inhalator, comprising an inhalator component as just described, and a reusable inhalator part which is couplable to the inhalator component; according to the invention, the second end of the pin is in ram-like operative connection to the reusable inhalator part during the coupling, as a result of which the previously described compressive force is produced. Therefore, the inhalator component is coupled to the reusable inhalator part and the liquid container is opened simultaneously by a single manipulation.

According to the invention, the reservoir communicates with the chamber via a ventilation duct, as a result of which air passes into the reservoir and compensates for the pressure. By this means, each portion of liquid material which passes into the capillary gap is immediately replaced by a portion of air identical in volume. It is essential that the ventilation duct is connected to the chamber and does not communicate with the external surroundings since otherwise the suction pressure would combine with the capillary flow during inhalation, and liquid material would be sucked out of the liquid container in accordance with the straw principle.

In a second variant embodiment, the liquid container is arranged in the housing so as to be manually displaceable along a displacement axis between two stop positions, and, in the first stop position, the liquid container interacts with a blocking device which is not unlockable, and, in the second stop position, the liquid container interacts with an opening means which opens the openable closure. The blocking device basically prevents the liquid container from being removed from the housing. Therefore, as in the first variant embodiment, the liquid container cannot be removed from the housing—involving the same advantages in terms of safety as already described earlier. In a development of the second variant embodiment, the opening means comprises a first spike which is formed by the capillary gap and penetrates the openable closure in the second stop position, thus producing the coupling in terms of capillary action to the liquid material. Furthermore, a ventilation duct is again provided, the first end of which communicates with the chamber, and the second end of which is designed as a second spike which penetrates the openable closure in the second stop position. The first spike and the second spike therefore together form the opening means. The effect of this arrangement is similar to that of a coupling between a fountain pen and the ink cartridge thereof. Of course, the first spike and the second spike may also be combined to form a single common spike. The blocking device which is not unlockable can consist in a simple manner of a projection which is formed, for example, by the housing or the mouthpiece and against which the liquid container strikes in the first stop position. Finally, the second variant embodiment is concerned with an inhalator component, comprising a mouthpiece with a mouthpiece channel through which a user obtains the vapor-air mixture or/and condensation aerosol offered, and, according to the invention, the displacement axis is orientated at least approximately parallel to the center axis of the mouthpiece channel, and, at least in the first stop position, an end section of the liquid container laterally next to the mouthpiece projects out of the housing. The displaceable liquid container can be displaced in a simple manner into the second stop position thereof by the user pressing on the protruding end of the liquid container. The mouthpiece and the liquid container protrude out of the housing on the same end side of the inhalator component, this making the inhalator component handy and the use of same ergonomic.

Furthermore, according to the invention, a buffer store which communicates with the capillary gap and itself consists of capillaries can be provided. The buffer store has the capability of receiving liquid material from the capillary gap and, when the need arises, of dispensing the stored liquid material again via the capillary gap to the wick irrespective of position. As a result, the inhalator component can be operated in any position, at least as long as liquid material is stored in the buffer store. The capillaries can consist, for example, of slots, holes or of a porous material, wherein care should be taken to ensure that the capillary action or capillary pressure thereof (capillary rise) is lower than the capillary action of the wick, since otherwise capillary flow does not come about.

As an alternative to the previously described liquid container, the inhalator component can contain a liquid store which is composed of an elastic, open-pored material and is impregnated with the liquid material; according to the invention, the composite is clamped in the manner of a sandwich between one of the two plate-like contacts—as already described previously—and the liquid store, as a result of which the wick is coupled in terms of capillary action to the liquid material in the liquid store. The elastic, open-pored material can be composed, for example, of a fiber material or of foam. The liquid material is automatically sucked out of the liquid store into the wick and infiltrates the latter. A prerequisite is that the capillary action or the capillary pressure (capillary rise) of the wick is greater than the capillary action of the liquid store. The sandwich-like clamping constitutes a structurally simple arrangement which is cost-effective to produce.

In a development of the invention, the inhalation component contains a condensate binding device for receiving and storing condensate residues which are formed in the course of the production of the vapor-air mixture or/and condensation aerosol; considerable quantities of condensate residues can occur especially if the liquid material to be evaporated contains relatively large portions of low-boiling fractions with high vapor pressure, for example ethanol or/and water. Such portions of low-boiling fractions are advantageous especially for two reasons and also necessary in the case of the inhalator component according to the invention: firstly, such portions reduce the viscosity of the liquid material, thus enabling the liquid material to infiltrate the wick more rapidly. This effect has proven particularly advantageous in the composite according to the invention, since the thickness of the composite and, due thereto, also the average pore diameter of the wick are extremely small. Secondly, the low-boiling fractions cause drugs and other additives contained in the liquid material to more easily evaporate, and fewer evaporation residues are formed, and the thermal decomposition of the liquid material is reduced. In order to make said positive effects useful to a satisfactory extent, the mass portion of the low-boiling fractions should be significantly above 50%. As a consequence, considerable quantities of condensate residues which expediently have to be bonded are anticipated during operation of the inhalator component according to the invention.

According to the invention, the condensate binding device consists of an open-pored, absorbent body which is arranged spaced apart from, but in the direct vicinity of the wick capillary structure which is exposed in said section. The pores of the open-pored, absorbent body receive condensate deposits formed from the vapor phase and in this respect act in principle in a manner similar to a sponge. Even a relatively large quantity of condensate can easily be bonded. The open-pored, absorbent body prevents freely moveable condensate accumulations from forming in the inhalator component, in particular in the chamber, which condensate accumulations may have an adverse effect on the functioning in the inhalator component but also constitute a risk to the user and the environment if said accumulations contain drug residues or poisons, such as nicotine. The effect achieved by the special arrangement of the open-pored, absorbent body in the immediate vicinity of the vapor formation zone—i.e. in a region of high vapor density—is that the condensate residues are absorbed in a very high concentration and therefore highly effectively, and said condensate residues cannot offer the opportunity at all of dispersing into peripheral regions. It is particularly favorable if the open-pored, absorbent body directly covers the wick capillary structure which is exposed in said section, since the greatest vapor density should be anticipated in this zone. In an advantageous refinement of the invention, the open-pored, absorbent body comprises two parts or sections which are arranged spaced apart from each other, and the composite is at least partially arranged between the two parts or sections. Furthermore, it is considered as being according to the invention that the open-pored, absorbent body is arranged in the chamber and fills the predominant part of the chamber. This enables a particularly large absorption capacity for the liquid condensate residues to be realized with a compact construction. It is furthermore favorable if the open-pored, absorbent body consists of a dimensionally stable material which substantially retains the shape thereof even after complete infiltration by the condensate residues. In order to establish whether a specific material is dimensionally stable, it suffices to impregnate said material with an ethanol-water solution and to check the dimensional stability after a residence period of three days. The dimensional stability ensures that the flow conditions in the chamber, in particular around the composite, and therefore the conditions for forming the vapor-air mixture or/and condensation aerosol remain constant. By way of example, the open-pored, absorbent body can consist of a solid, foam-like material, such as metal foam or ceramic foam, of a porous sintered compact, of a porous filling material without swelling tendency, for example of a drying agent and granular material fill, or of a porous fiber composite, for example formed from natural or chemical fibers interconnected thermally or with the aid of a binding agent. In addition, it is essential for the material to be very substantially chemically inert to the condensate residues.

According to a preferred embodiment of the invention, the open-pored, absorbent body is substantially surrounded by the housing and is connected nonseparably to the housing. The effect which is therefore intended to be achieved is for the open-pored, absorbent body not to be able to come into contact directly with the environment, and for removal of said body from the housing to be possible only by the application of force and destruction of the inhalator component. Said protective measure has proven advantageous especially if the condensate contains drug residues or/and poisons, such as nicotine. The inhalator component together with the open-pored, absorbent body forms a disposable article which should be disposed of properly after the designated service life is reached.

In an advantageous development of the invention, a two-stage condensate deposition device is provided, consisting firstly of the open-pored, absorbent body and secondly of a cooler through which the vapor-air mixture formed and/or condensation aerosol can pass. This development of the invention is suitable in particular for use in drawing inhalators. The cooler cools the vapor-air mixture or/and condensation aerosol passing therethrough and in the process removes even more condensate therefrom. The cooler can be formed, for example, by a pore body through which the flow can pass and which is substantially permeable to the particles of the condensation aerosol formed. In addition to the cooling, the pore body also brings about intimate mixing of the vapor-air mixture or condensation aerosol passing therethrough, as a result of which the properties of said mixture or aerosol are homogenized, for example, concentration peaks are reduced. The pore body typically consists of a wide-pored material, for example of an open-cell foam material, of a coarse-pored, porous filling material or of a fiber material in the manner of a nonwoven. Synthetic nonwovens manufactured from polyolefin fibers (PE, PP) or polyester fibers should be mentioned as an example of a fiber material in the manner of a nonwoven. The pore body may also be composed of a regenerator material. The regenerator material, with a large surface or heat exchange surface, is capable of absorbing a large amount of heat rapidly without substantial flow losses. Typical regenerator materials include: metal wool, metal chips, metal mesh, wire knits, metal nonwovens, open-cell metal foams, and fills made from metallic or ceramic granular material. Finally, the cooler may also be of multi-stage construction by various porous materials being combined with one another. Of course, the invention is not restricted to the previously enumerated cooler materials. By means of the cooling and homogenization, the organoleptic properties of the vapor-air mixture or/and condensation aerosol received by the user can be significantly improved.

In a particularly preferred refinement of the invention, the cooler is formed by a tobacco filling. In addition to the cooling/condensation and homogenization, the tobacco filling additionally brings about aromatization of the vapor-air mixture or condensation aerosol passing therethrough and is especially appropriate if the liquid material contains nicotine as the drug. Moreover, in laboratory tests with prototypes operating in accordance with the drawing inhalator principle and with nicotine-containing drug preparations as the liquid material, further favorable effects have also been established: for example, the inhalability of the nicotine-containing vapor-air mixture and condensation aerosol could be improved, which can partially be attributed to a certain extent to the effects described above. However, there is the hypothesis that additional operative mechanisms are involved—in particular diffusion and adsorption processes relating to the free, unprotonized nicotine, which still have to be investigated in detail. The filling density of the tobacco filling is upwardly restricted by the fact that the filling firstly has to be as permeable as possible to the aerosol particles passing therethrough and, secondly, the induced flow resistance should not be greater than that of cigarettes. The tobacco filling can be formed from cut tobacco, finely cut tobacco, stuffing tobacco, from a cigar-like bundle of tobacco or from comparable or similar forms of tobacco. In particular, dried and fermented tobacco, reconstituted tobacco, expanded tobacco or mixtures thereof are suitable as the tobacco. The tobacco can additionally be sauced, spiced, aromatized or/and perfumed. The use of a tobacco filling as the cooler can also make the change from tobacco products to the inhalator component according to the invention more attractive or/and facilitate said change. In a preferred development of the invention, it is provided that the volume of the tobacco filling is greater than 3 $cm^3$. In separate laboratory tests, it has been shown that the abovementioned effects of the tobacco filling are beneficial in an extent satisfactory for the user only above the previously specified minimum value.

According to a further embodiment of the invention, the inhalator component comprises a mouthpiece opening which is formed by a mouthpiece and communicates with the chamber and through which a user receives the vapor-air mixture or/and condensation aerosol offered, wherein, in the course of the inhalation, a flow in the direction of the mouthpiece opening is formed between the air admission opening and the mouthpiece opening, at least part of which flow passes the composite. According to the invention, at least one air bypass opening is arranged downstream of the composite, through which air is additionally fed into the flow from the surroundings, and the effective flow cross section of the air bypass opening is at least 0.5 $cm^2$. This arrangement makes the inhalator component also useable for classic inhalators which basically require as low a flow resistance as possible. The air additionally flowing through the air bypass opening ("bypass air") does not itself pass the composite and, as a result, also does not have any direct influence on the formation of the vapor-air mixture or/and condensation aerosol and on the properties thereof. However, there is an indirect influence in so far as the bypass air reduces the quantity of air ("primary air") flowing in through the air inlet opening if a constant quantity of inhalation air is required. The quantity of primary air can thereby be reduced arbitrarily. A reduction in the quantity of primary air results, inter alia, in an increase in the aerosol particles formed; at the same time, however, the quantity of condensate residues formed also increases, but this can be counteracted by the arrangement of a condensate binding device—as previously described. According to the invention, a further reduction in the flow resistance and a further reduction in the quantity of primary air are obtained by the air bypass opening consisting of two bypass openings which are arranged in opposite housing sections.

According to the invention, it is furthermore provided that the two bypass openings are adjoined by two guide vanes which point in the direction of the mouthpiece opening and strive toward each other, and the free ends of which form a nozzle-shaped mouth opening through which the vapor-air mixture formed or/and condensation aerosol flows out of the chamber and is subsequently mixed with the air flowing in from the bypass openings. The two guide vanes have the effect of substantially covering the chamber to the outside, thus significantly reducing the risk of, for example rainwater or saliva entering the chamber. In addition, the exchange of air between the chamber and the surroundings is also limited, and therefore the natural vaporization of portions of the liquid material in the wick is reduced. Such a vaporization can prove unfavorable, in particular during prolonged periods of the inhalator component not being used, in so far as the composition of the liquid material can change, and, in the case of drugs, the dosing thereof may differ from the target.

It is also considered as being according to the invention that a flow homogenizer is arranged downstream of the air bypass opening, the flow resistance of which flow homogenizer is lower than 1 mbar at an air throughput of 250 mL/sec. The flow homogenizer is passed through both by the vapor-air mixture formed or/and condensation aerosol and by the bypass air flowing in through the air bypass opening, and thoroughly mixes and homogenizes said two flow components. Concentration peaks are dissipated, and the homogenized mixture emerging from the mouthpiece opening is more pleasant for the user to inhale. The flow homogenizer can consist by way of example of a material in the manner of a nonwoven or foam; such a material is suitable for producing flow turbulences and eddies to a sufficient degree without exceeding the cited limit value for the flow resistance. Only in this way can the inventive refinement just described be used for a classic inhalator.

In an optional refinement of the invention, a plurality of composites arranged next to one another and having differing heat capacity is provided. In a further optional refinement of the invention, a plurality of composites arranged next to one another and having differing heating element properties is provided. In a further optional refinement of the invention, a plurality of composites arranged next to one another and having electric heating elements which are activatable in different ways is provided. In a further optional refinement of the invention, a plurality of composites arranged next to one another is provided, and the individual composites are assigned liquid materials of differing composition for evaporation by the wick of said composites being fed by sources containing different liquid material. The abovementioned refinement options which, furthermore, can also be combined with one another arbitrarily make it possible to configure the evaporation process to be more variable in terms of space and time. This variability permits even the complex ratios in the distillation zone of a cigarette to be approximately simulated.

In a special refinement of the invention, a plurality of composites arranged next to one another is provided, the heating elements of which consist of electric heating resistors; according to the invention, the heating resistors are connected in series to one another. This special refinement has proven particularly advantageous if the heating resistors consist of a metallic resistance material, for example stainless steel or heating conductor alloys, since the series connection and the associated increase in resistance enable the heating stream to be limited to an extent which can still be readily controlled by the electronic activation and by the energy store. Furthermore, by means of the increase in resistance, the power density in the composite can be throttled if required such that stable evaporation can always be ensured.

Expedient and advantageous exemplary embodiments of the invention are illustrated in the drawings and are explained in more detail in the description below.

In the drawings:

FIGS. 1A, 1B, 1C show, respectively, back, side, and front views of a first embodiment of an inhalator according to the invention, in the form of a drawing inhalator;

Figures 2A, 2B:
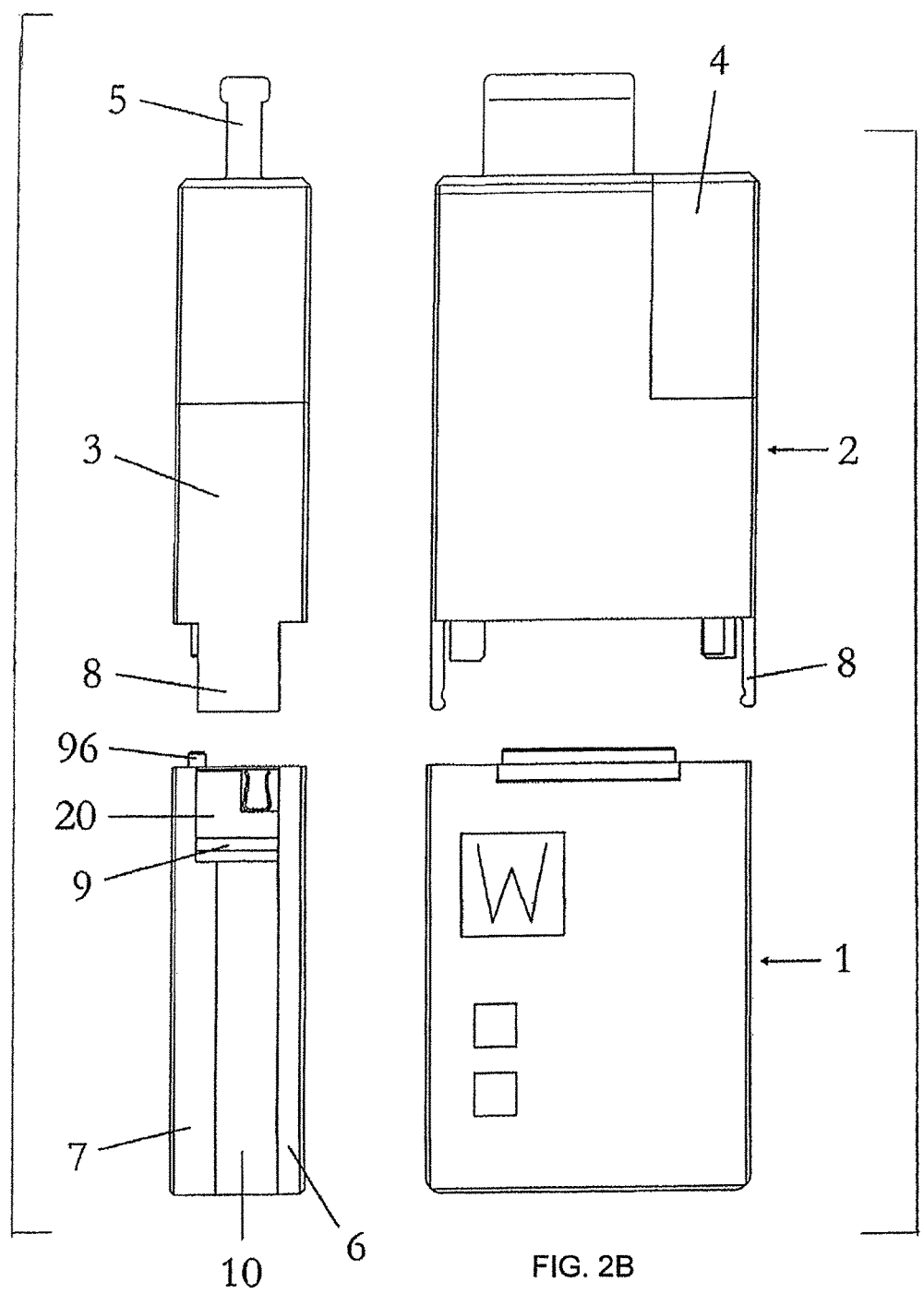
FIGS. 2A and 2B show, respectively, side and front views of an inhalator according to FIG. 1A with a reusable inhalator part and an exchangeable inhalator component in the decoupled state.
Figure 3A:
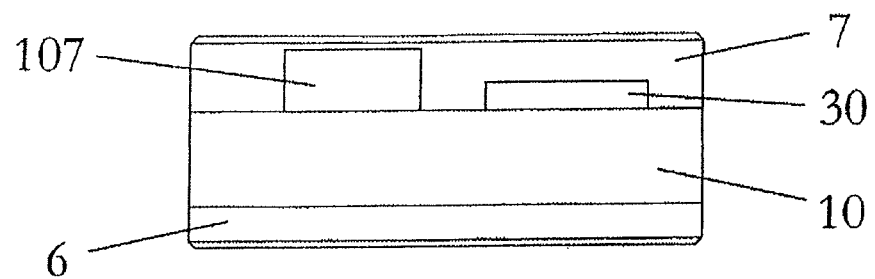
FIGS. 3A, 3B, 3C show, respectively, bottom, front and top views of the reusable inhalator part.
Figure 3B:
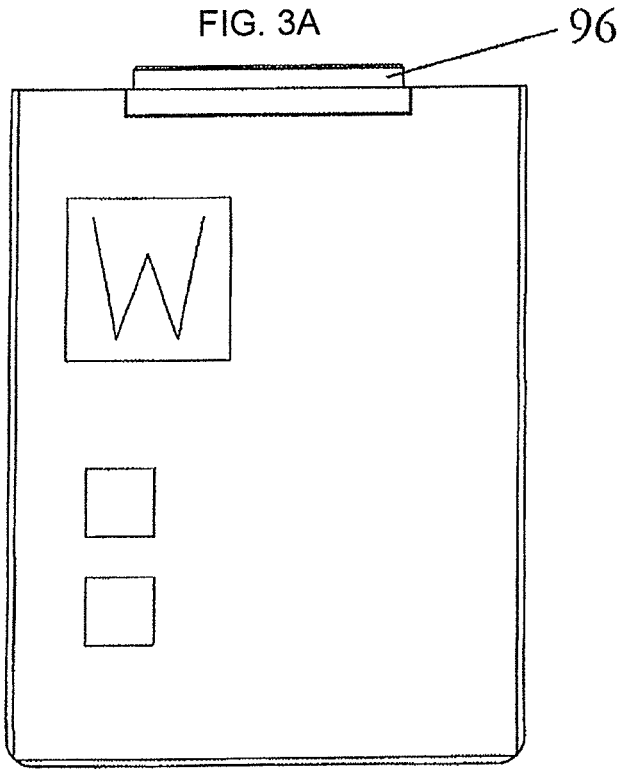
Figure 3C:
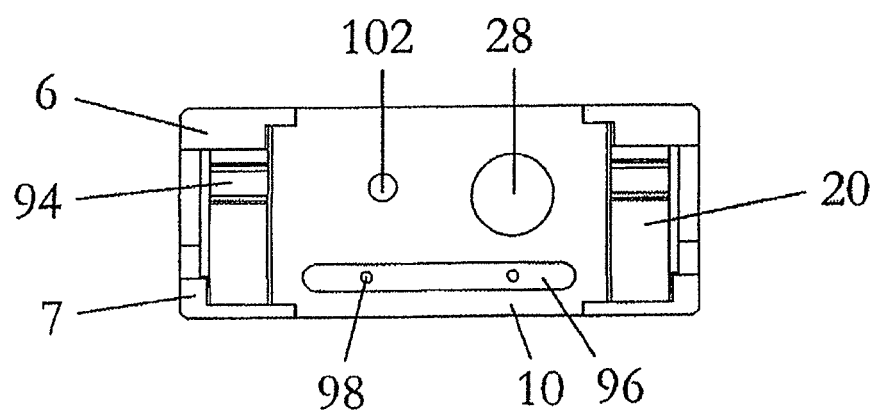
Figure 4A:
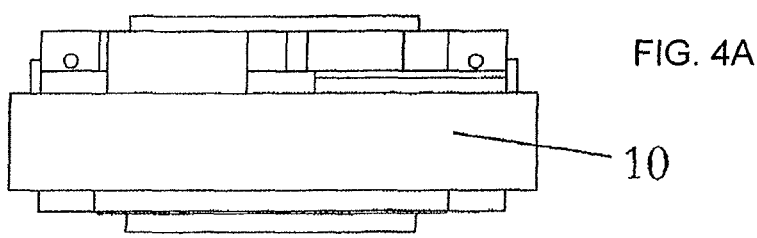
Figure 4B:
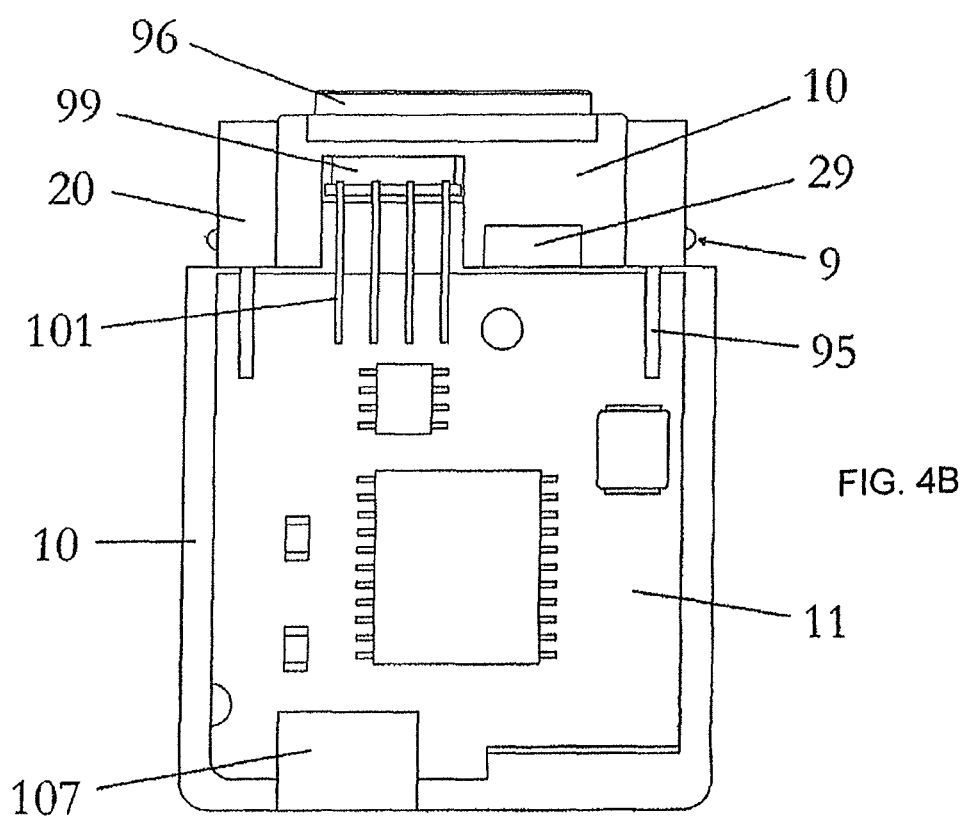
Figure 4C:
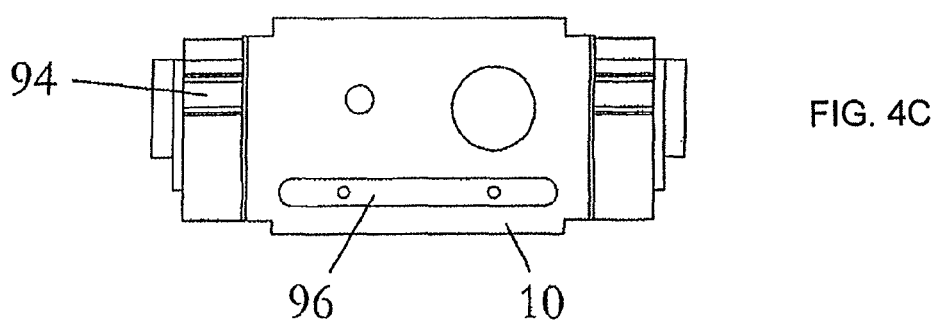
Figure 6A:
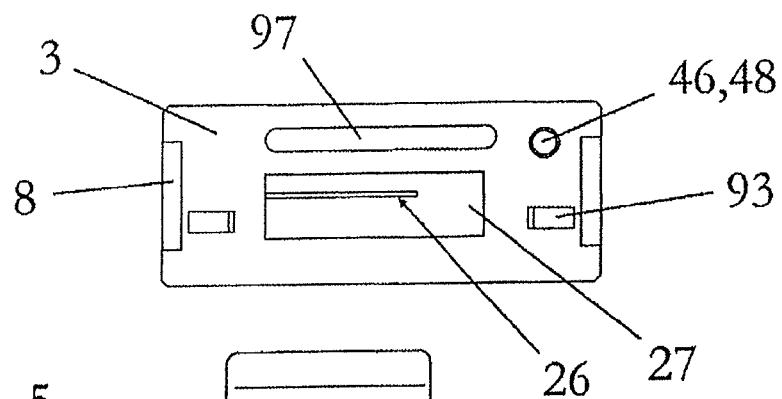
Figure 6B:
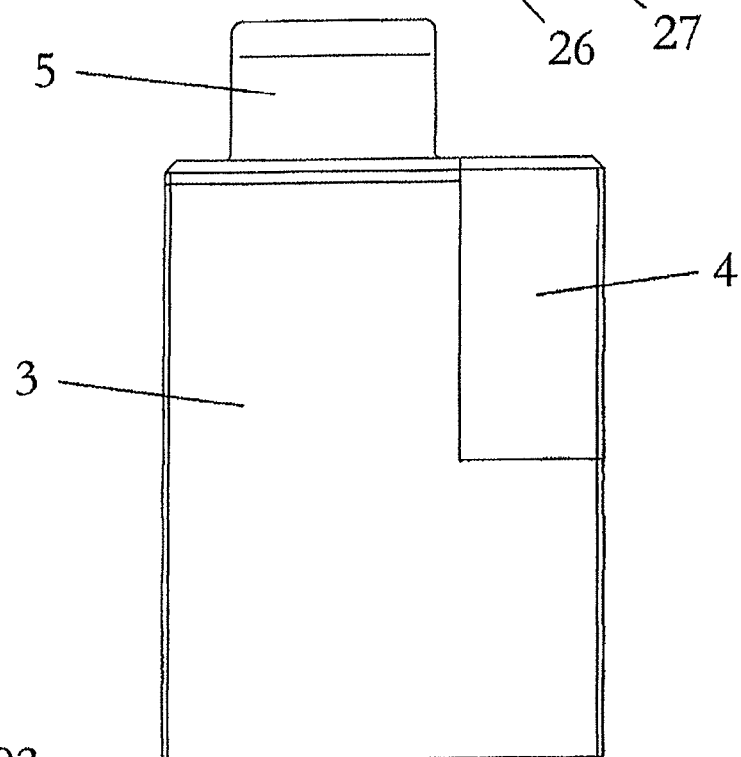
Figure 6C:
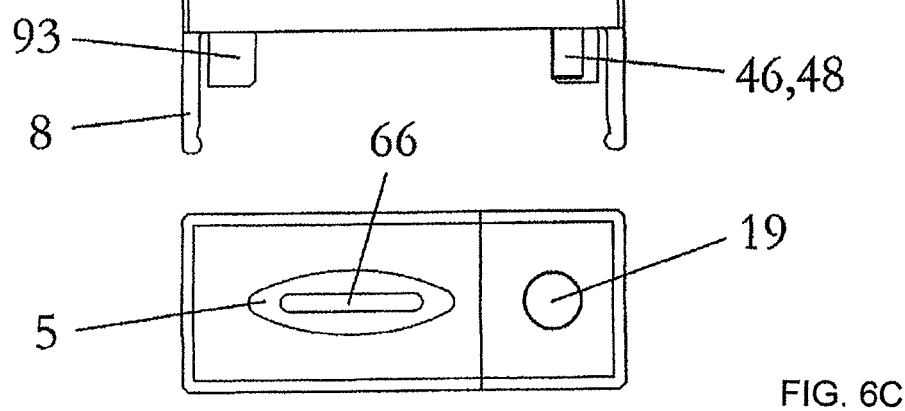
Figure 8:
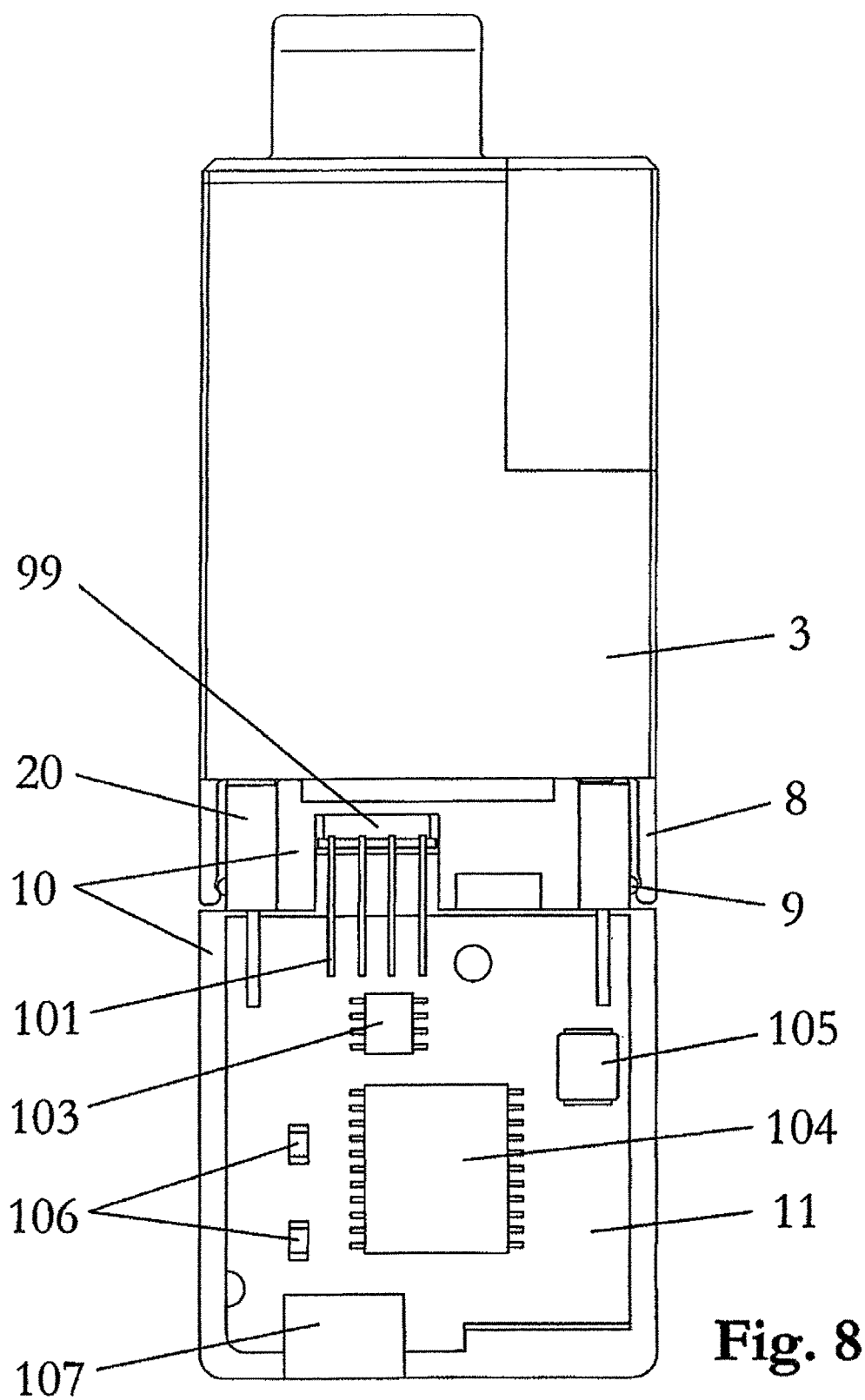
Figure 9:
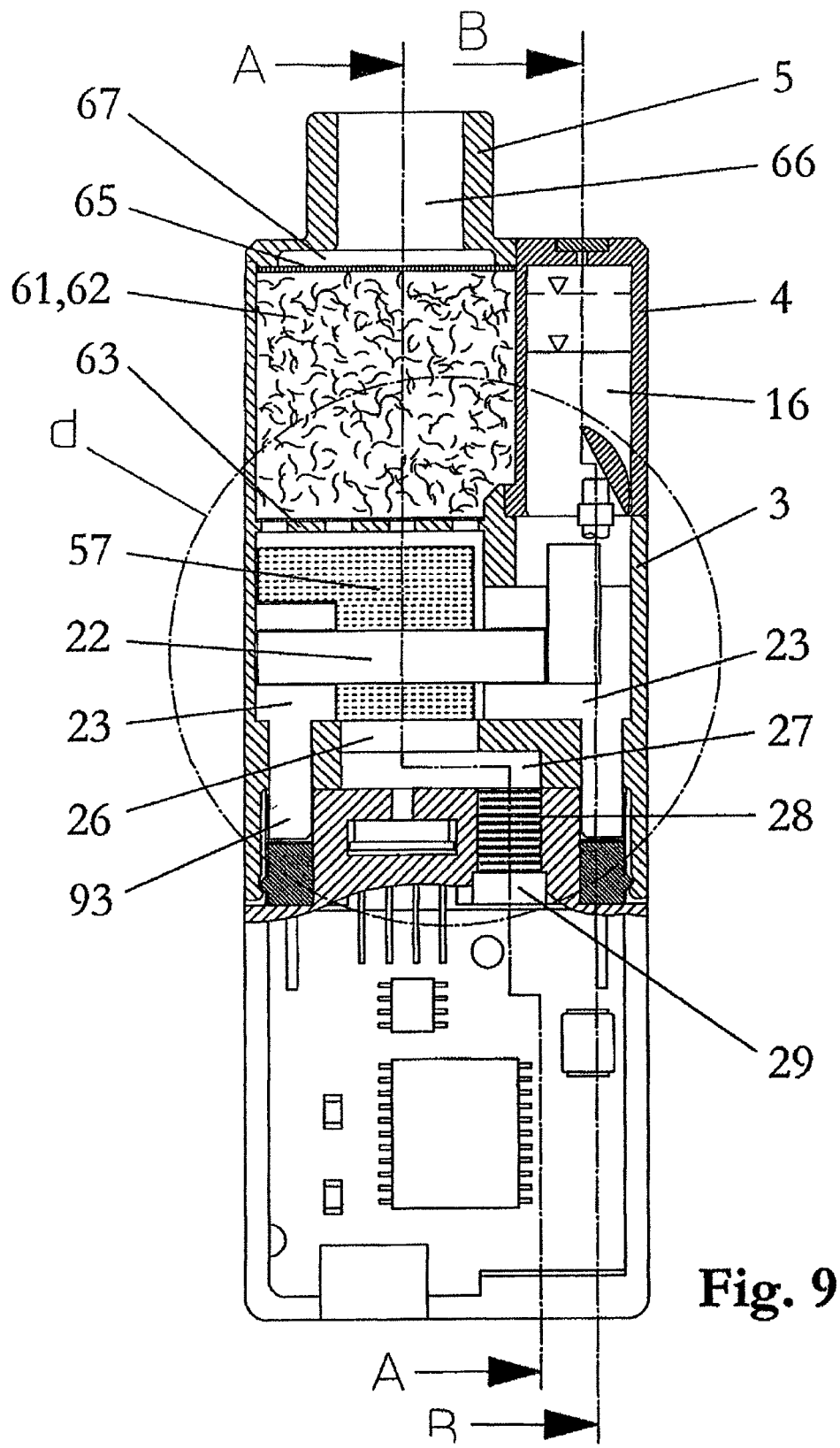
Figure 10:
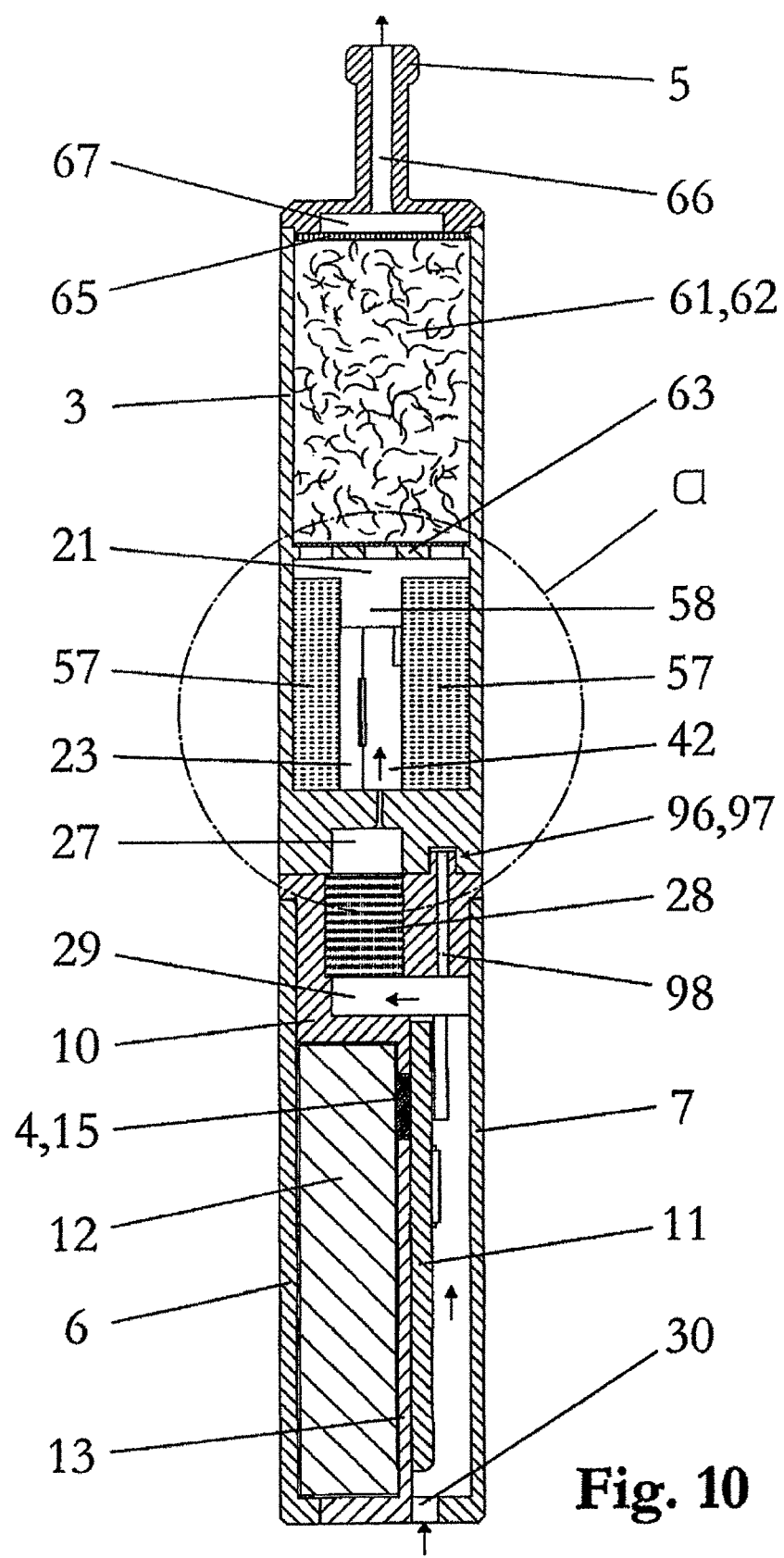
Figure 11:
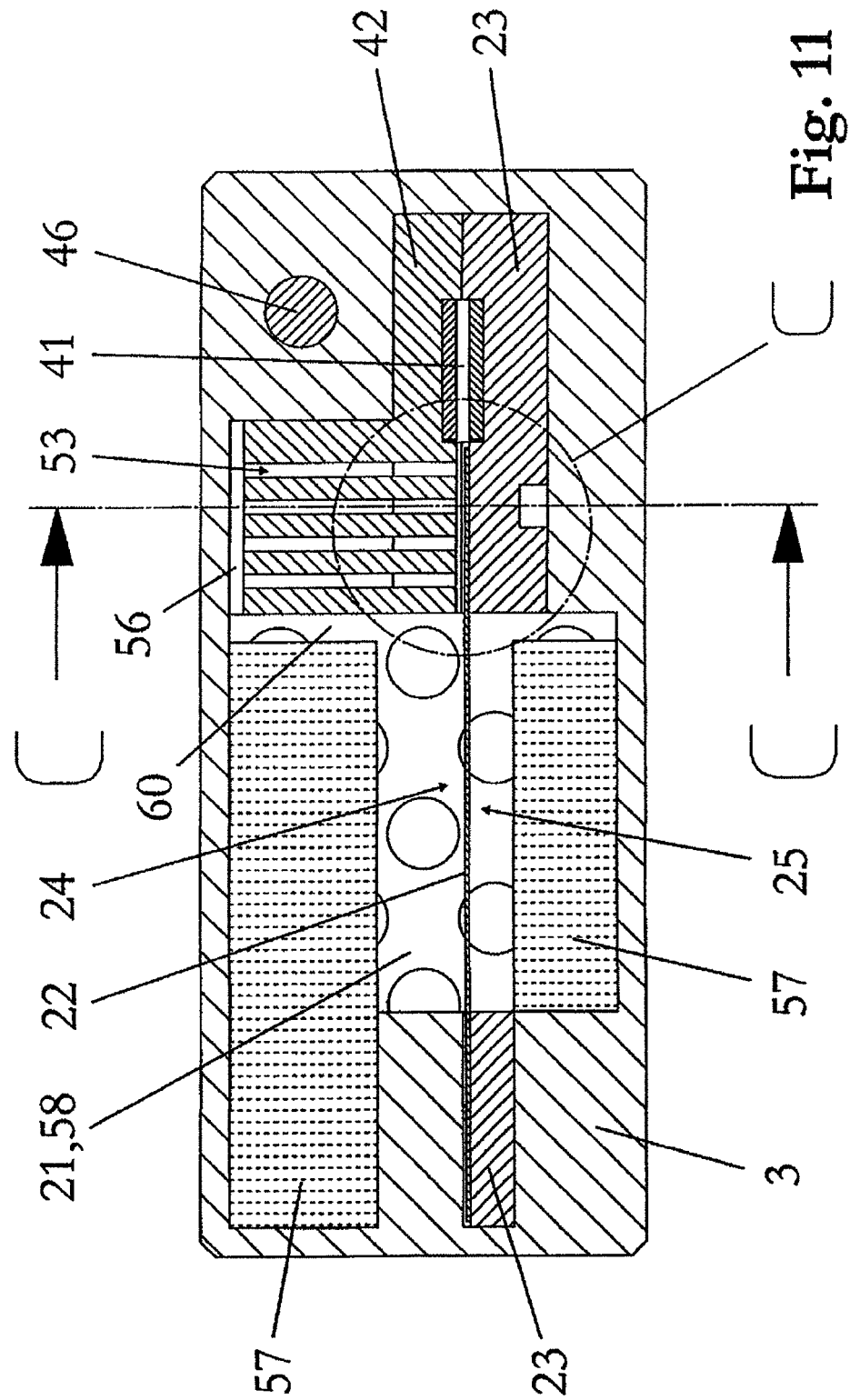
Figure 12A:
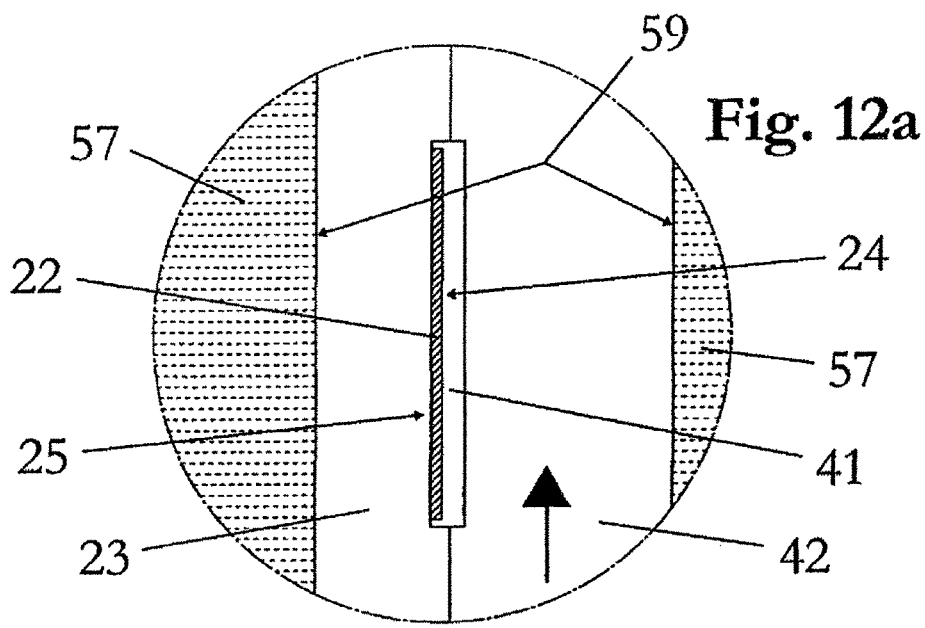
Figure 12:
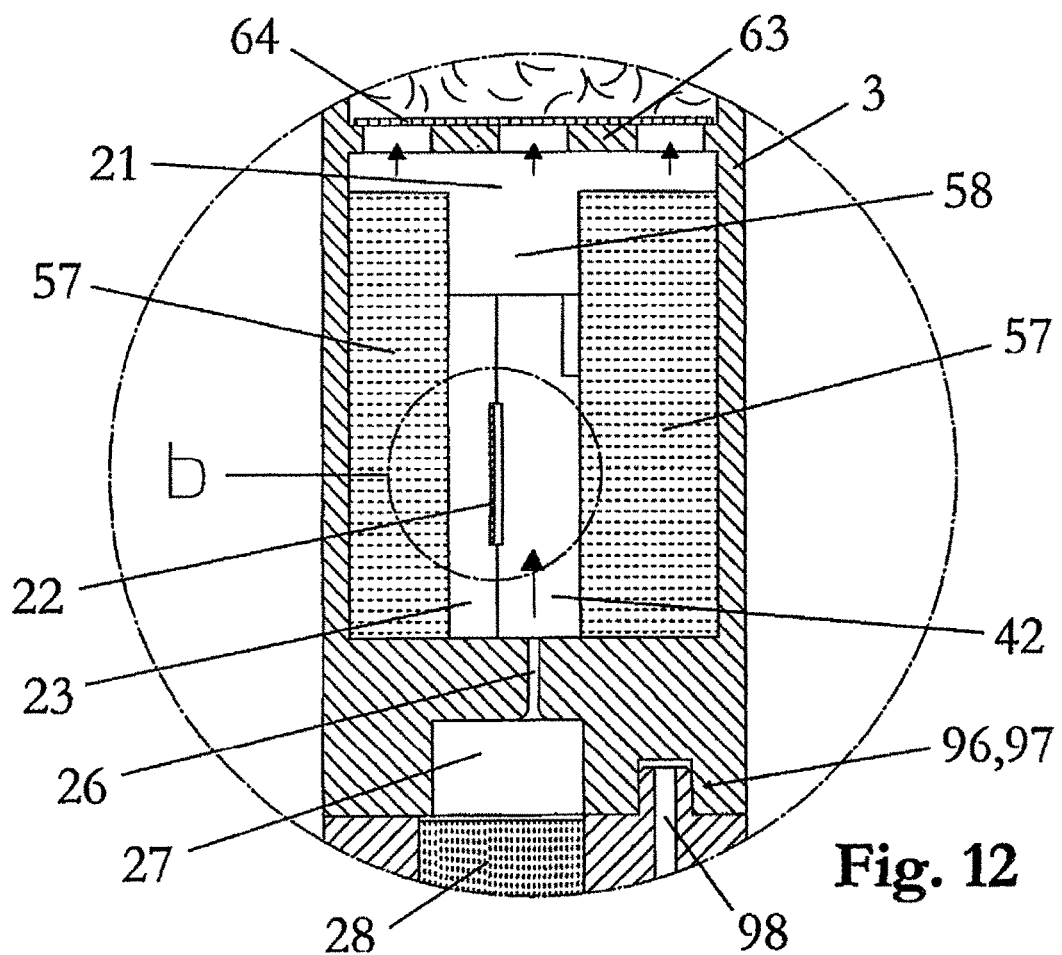
Figure 14A:
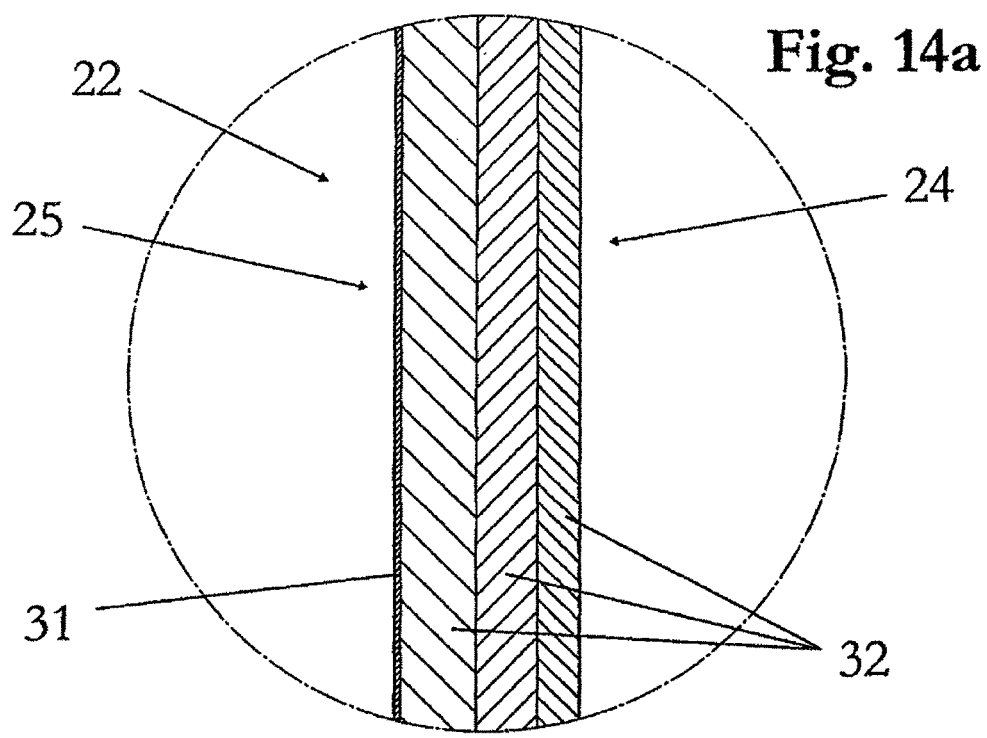
Figure 14B:
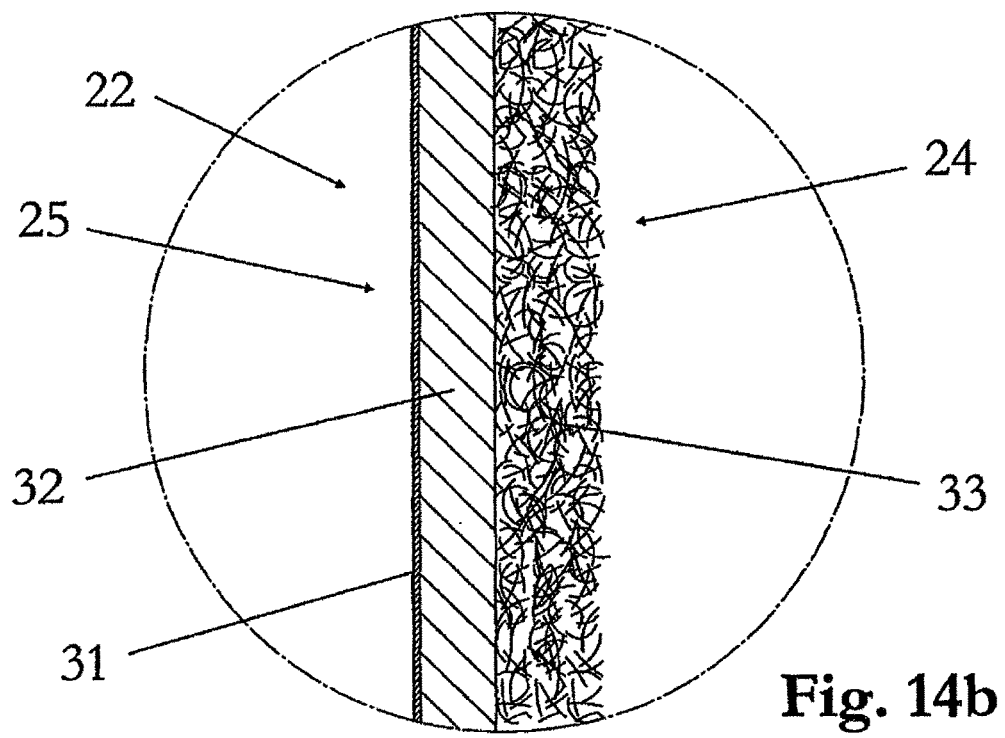

FIGS. 4A, 4B, and 4C show, respectively, bottom, back and top views of the reusable inhalator part without the battery cover;

FIGS. 5A, 5B, and 5C show, respectively, side, back (without the switching circuit cover) and back (without the battery) views of the reusable inhaler part;

FIGS. 6A, 6B, and 6C show, respectively, bottom, front, and top views of the exchangeable inhalator component;

FIG. 7A shows the exchangeable inhalator component with the liquid container and mouthpiece illustrated separately;

FIGS. 7B and 7C show, respectively, side and cross-sectional views of the liquid container shown in FIG. 7A;

FIG. 8 shows the inhalator according to FIG. 1A without the switching circuit cover;

FIG. 9 shows a longitudinal section through the inhalator according to FIG. 8 level with the planar composite, wherein the sectional view on the other side of the composite has been expediently adapted;

FIG. 10 shows a sectional view of the inhalator along the line A-A in FIG. 9 with the switching circuit cover;

FIG. 11 shows a cross section of the inhalator according to FIG. 1A level with the planar composite;

FIG. 12 shows the detail a from FIG. 10 in an enlarged illustration;

FIG. 12a shows the detail b from FIG. 12 in an enlarged illustration;

FIG. 13a and FIG. 13b show alternative variant embodiments relating to the detail a;

FIG. 14a, FIG. 14b and

Figure 17:
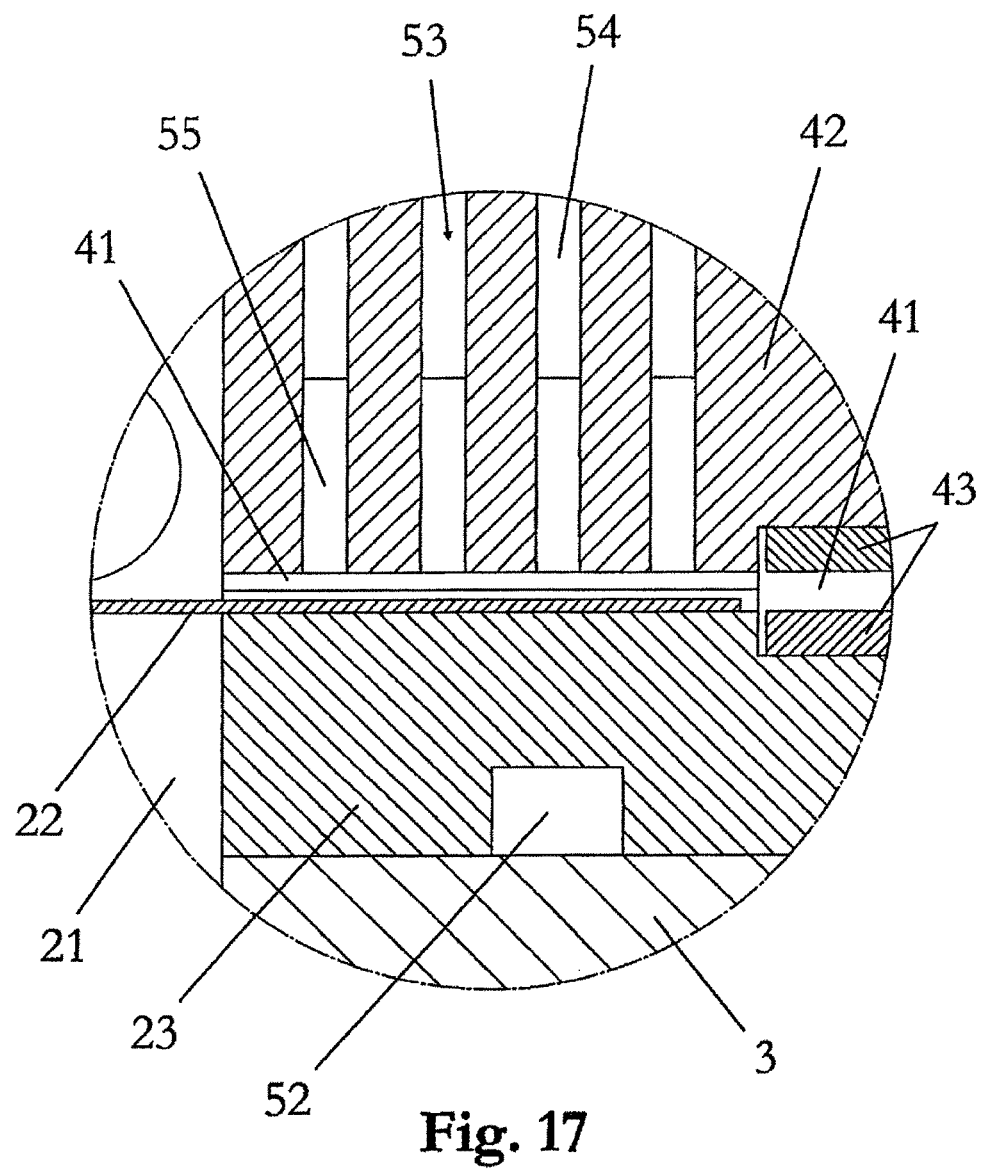
Figure 18:
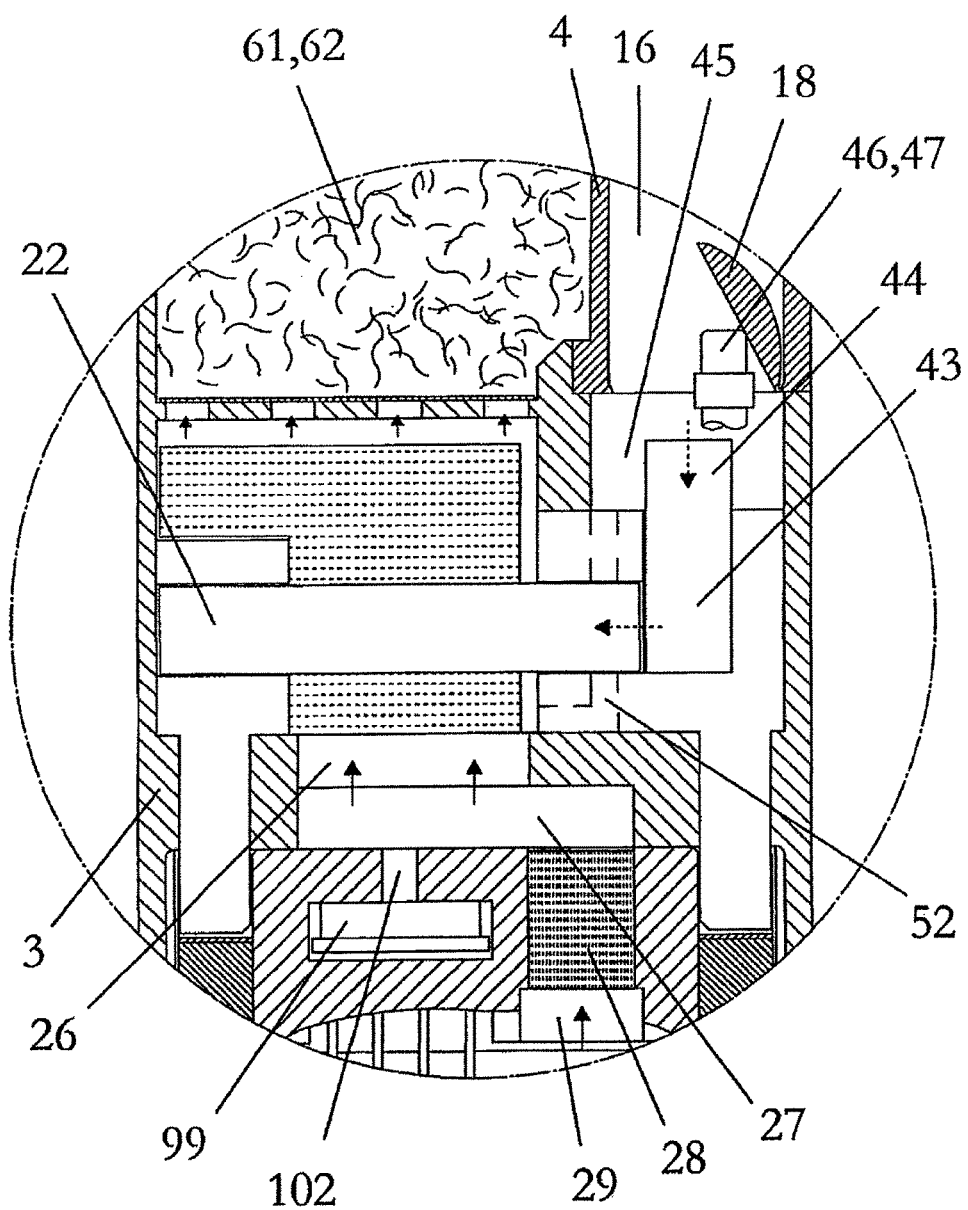
Figure 19:
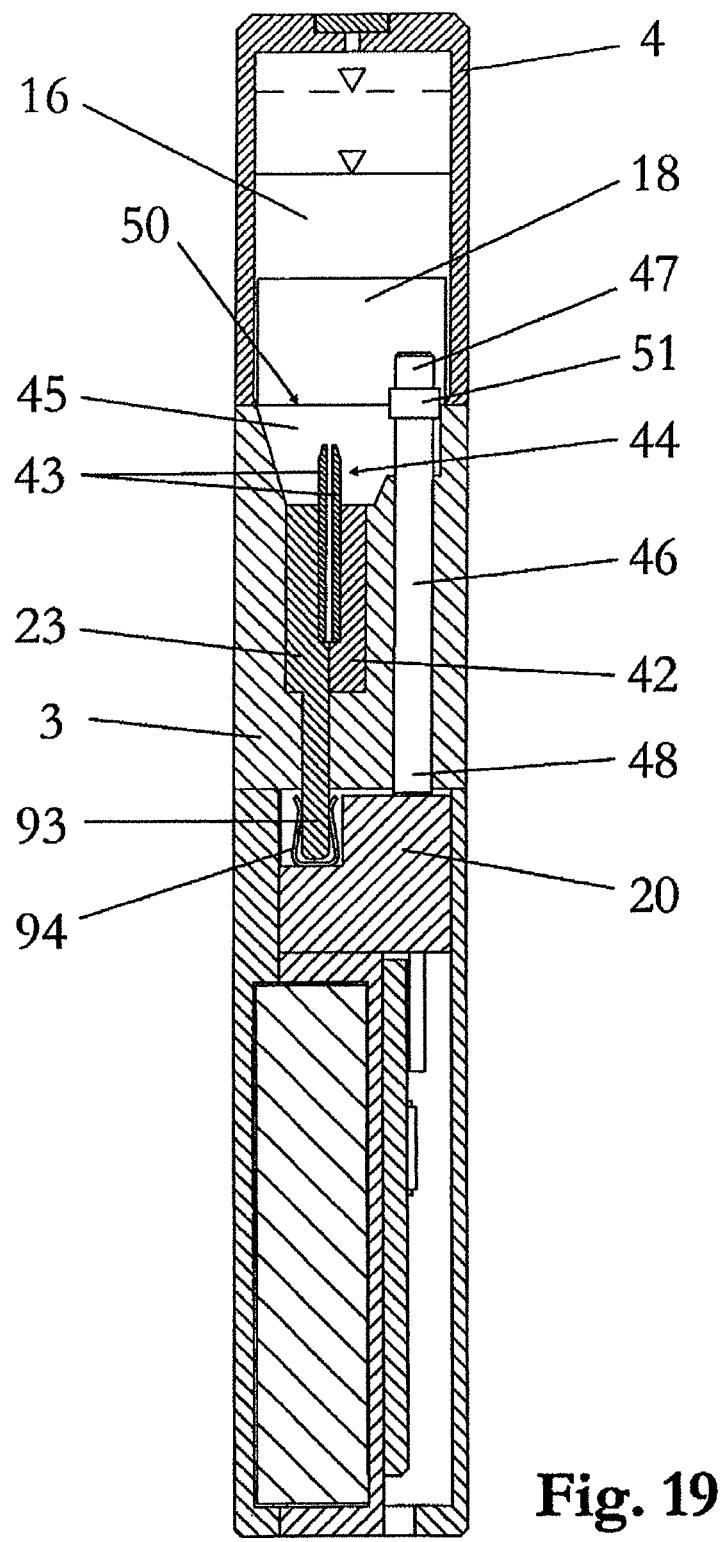
Figure 20:
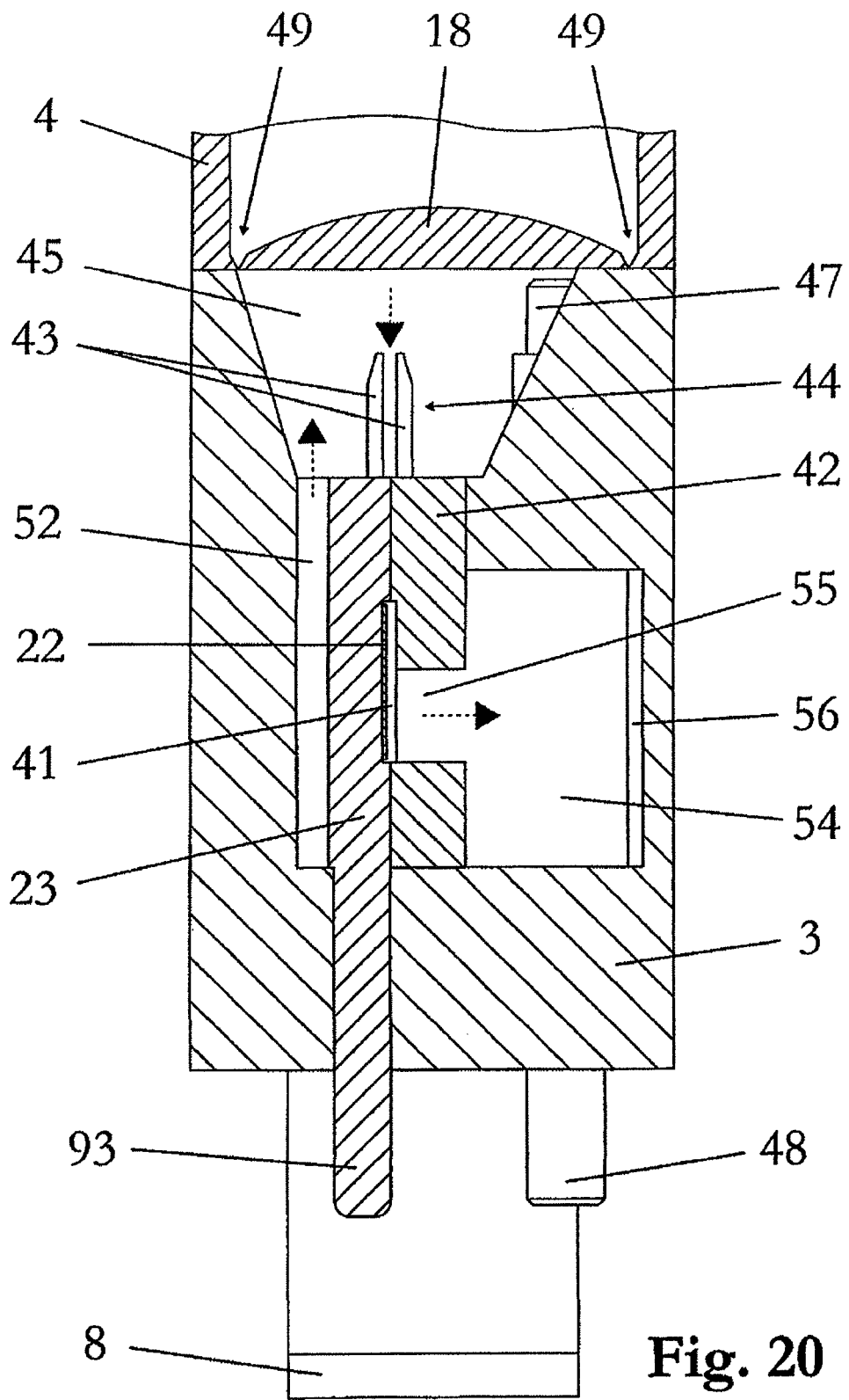
Figure 21:
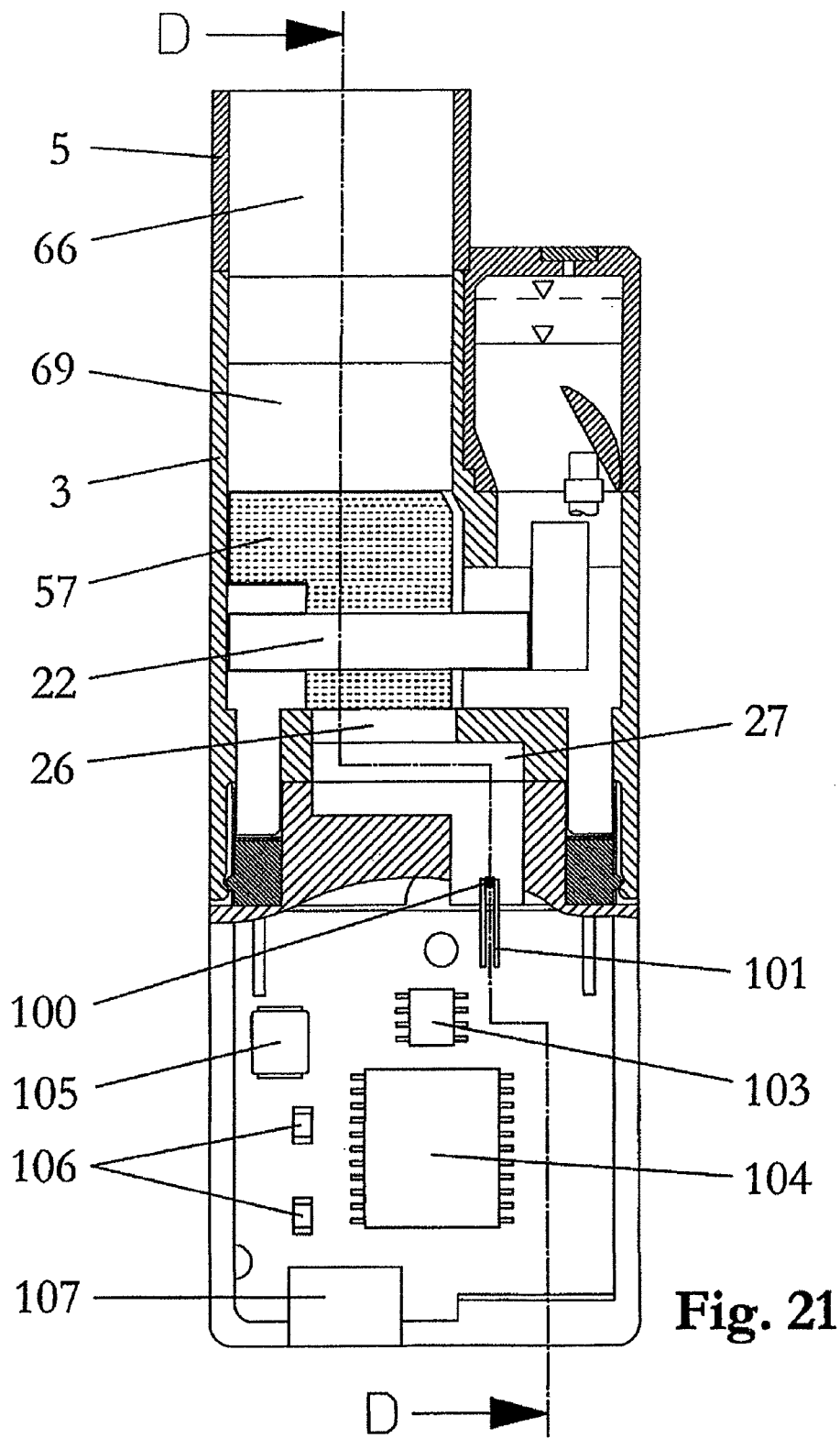
Figure 22:
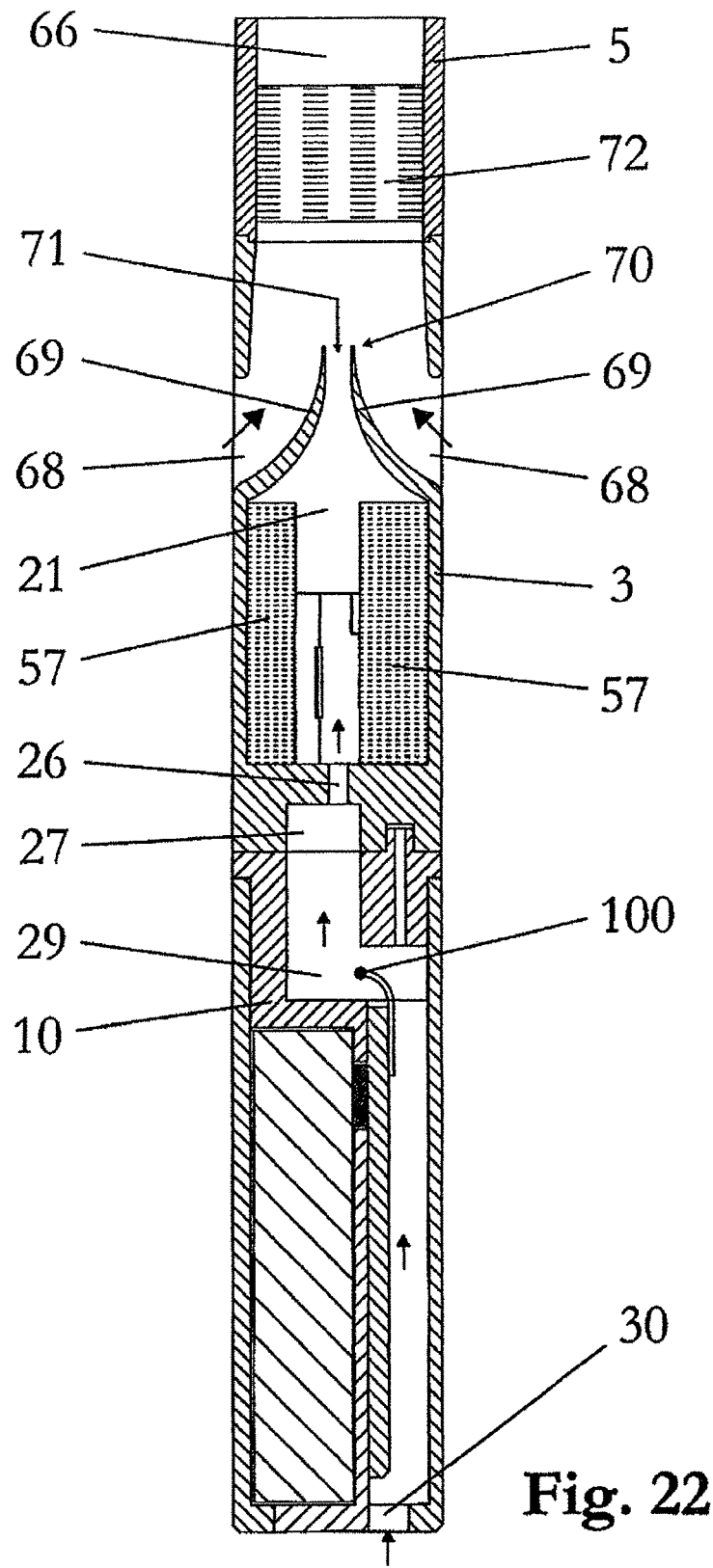
Figure 23A:
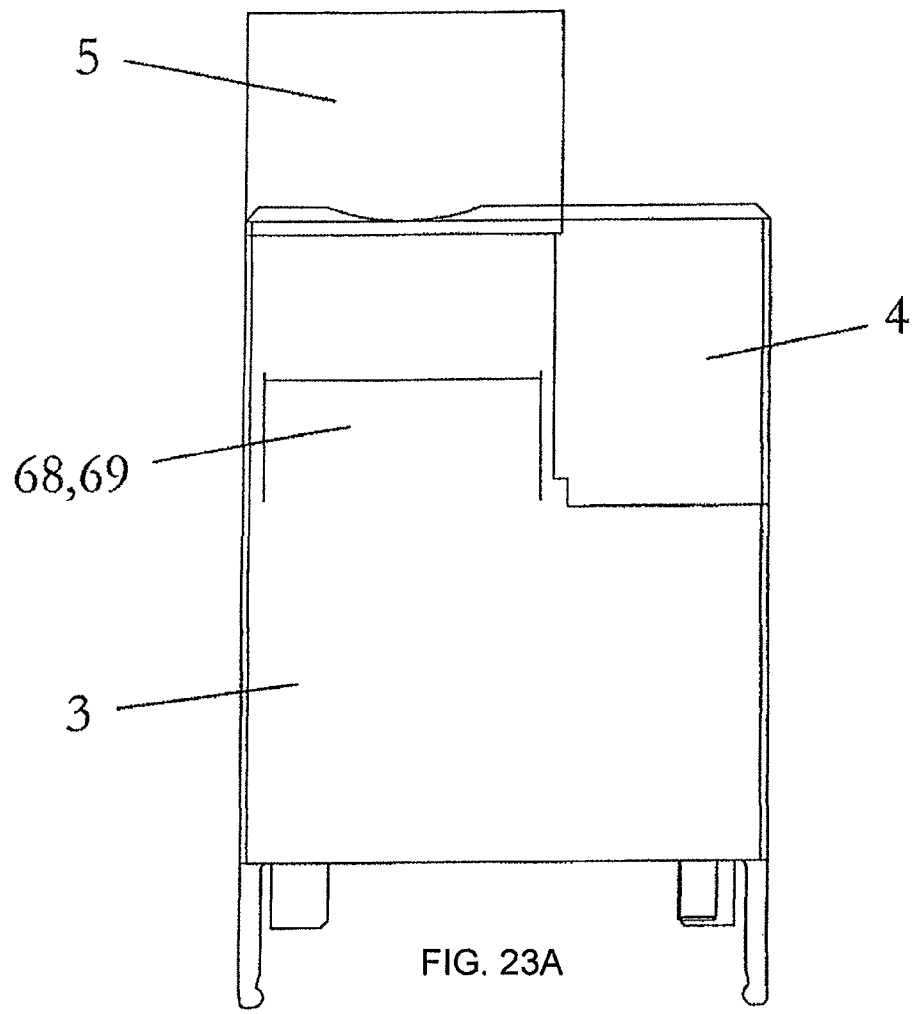
Figure 23B:
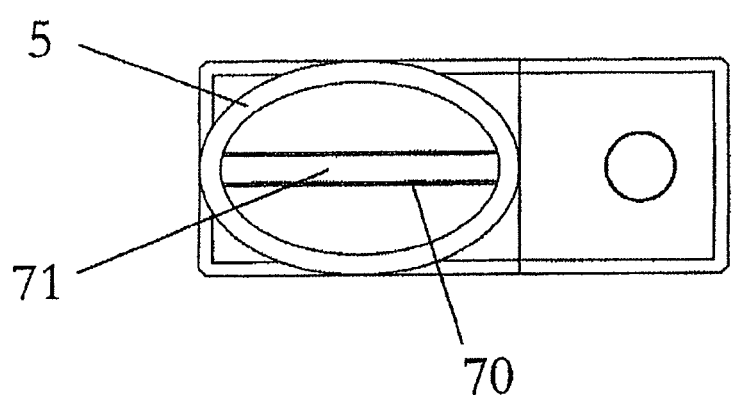
Figure 25:
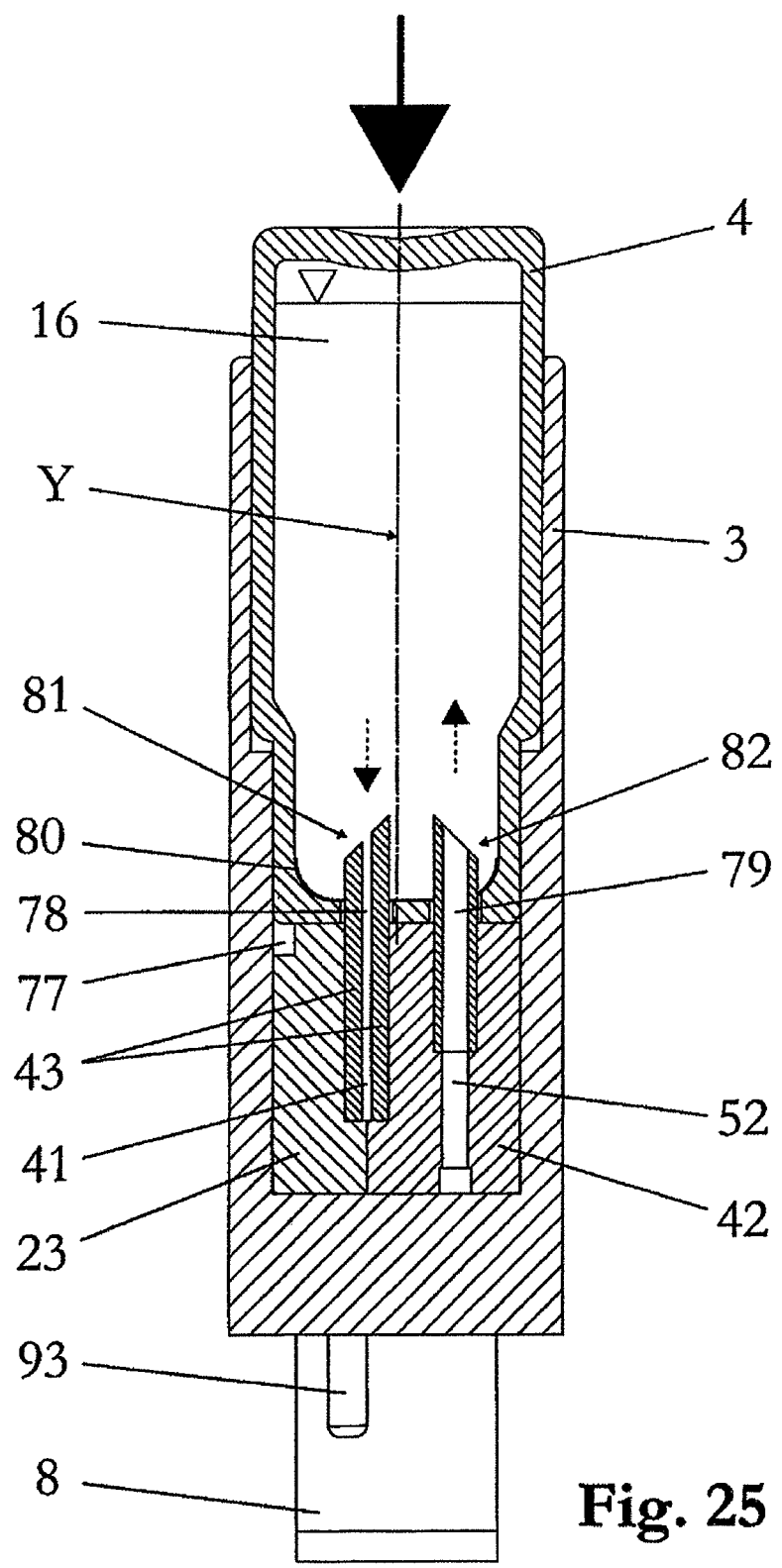
Figure 28:
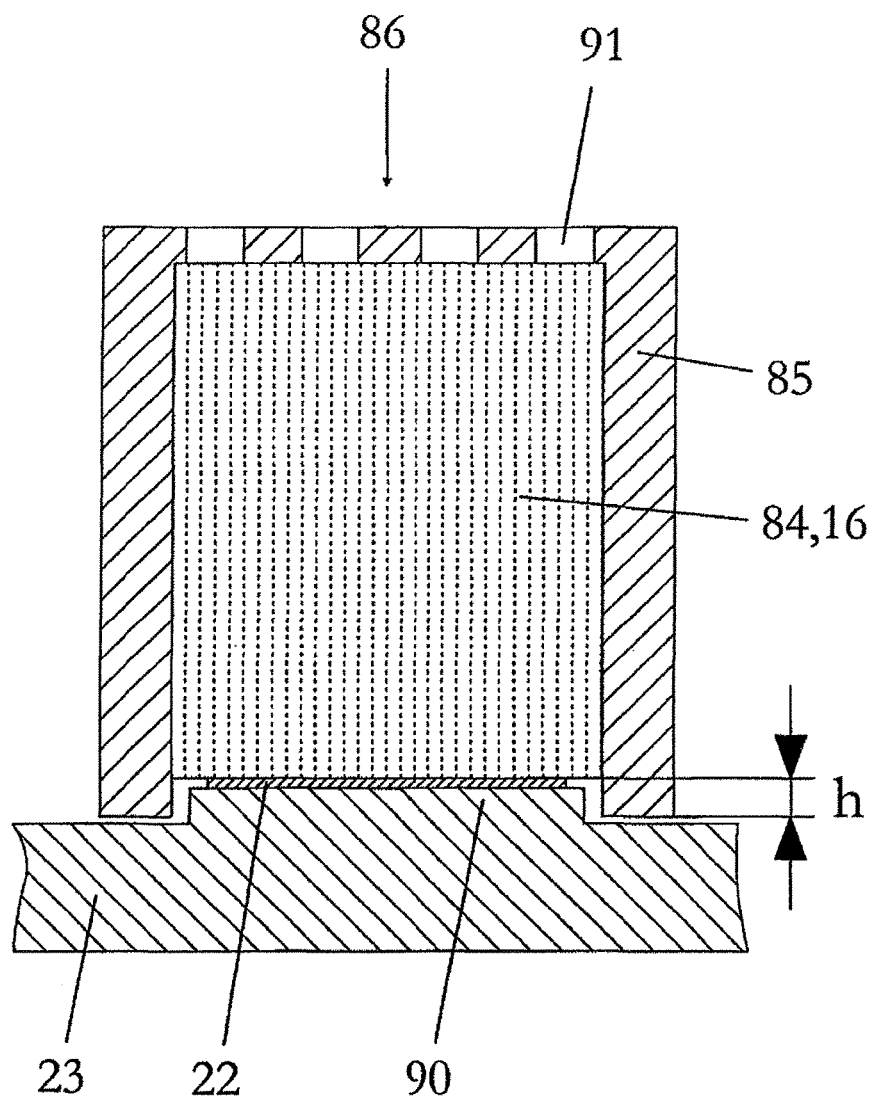
Figures 29A, 29B:
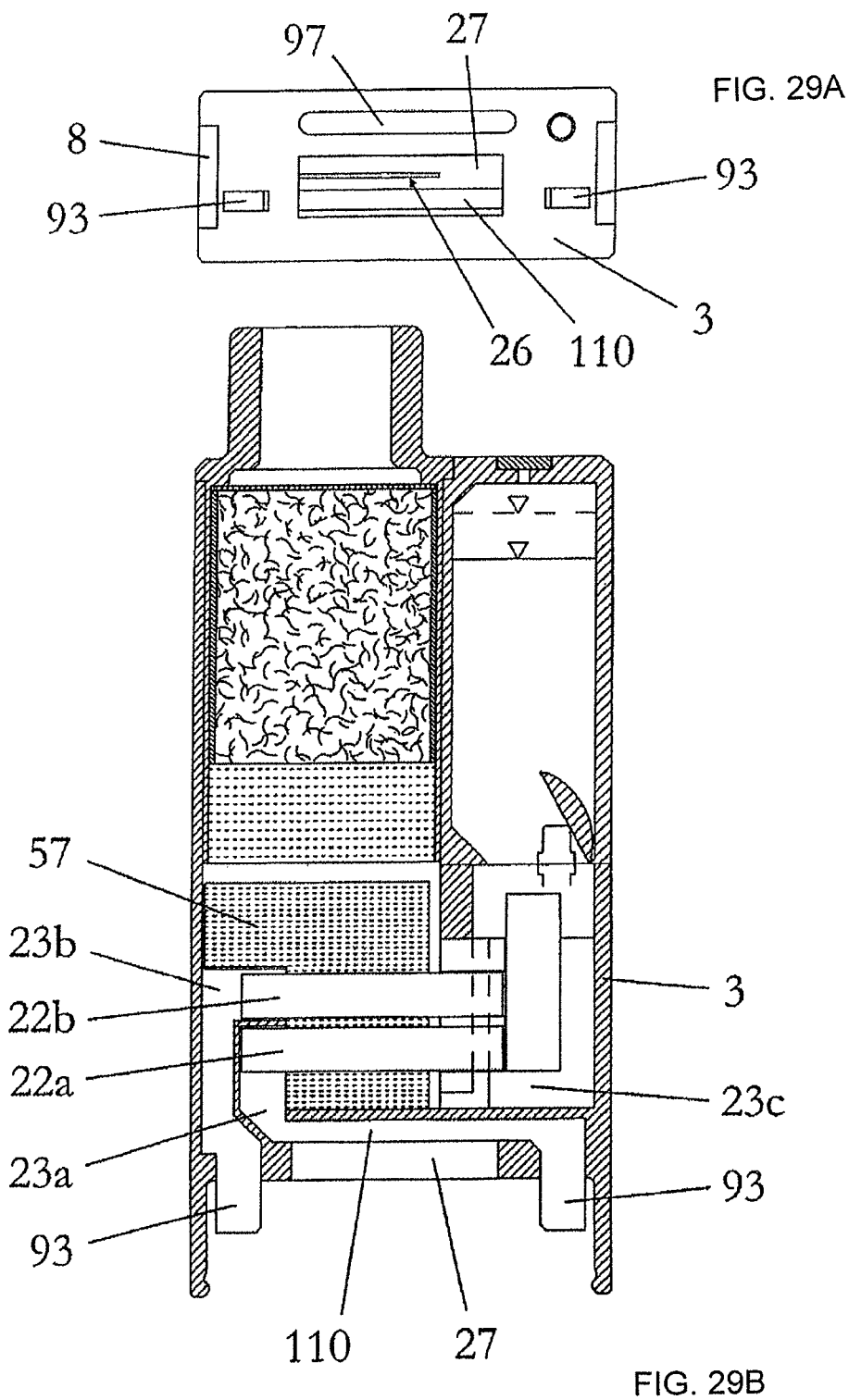

FIG. 15a, FIG. 15b and FIG. 15c show cross sections of various embodiments of planar composites in an enlarged illustration;

FIG. 16 shows a variant embodiment relating to the detail b from FIG. 12 with three linear composites arranged next to one another;

FIG. 16a shows a cross section of an individual linear composite according to FIG. 16 in an enlarged illustration;

FIG. 17 shows the detail c from FIG. 11 in an enlarged illustration;

FIG. 18 shows the detail d from FIG. 9 in an enlarged illustration;

FIG. 19 shows a sectional view of the inhalator along the line B-B in FIG. 9 with the switching circuit cover;

FIG. 20 shows a sectional view of the exchangeable inhalator component along the line C-C in FIG. 7A and FIG. 11 with the liquid container indicated;

FIG. 21 shows a second embodiment of an inhalator according to the invention, in the form of a classic inhalator, in a view analogously to FIG. 9;

FIG. 22 shows a sectional view of the inhalator according to FIG. 21 along the line D-D in FIG. 21 with the switching circuit cover;

FIGS. 23A and 23B show, respectively, front and top views of the exchangeable inhalator component of the inhalator according to FIG. 21;

FIG. 24a and FIG. 24b show an exchangeable inhalator component with an alternative liquid container system, wherein the inhalator component according to FIG. 24b is illustrated torn open around the liquid container;

FIG. 25 shows a sectional view of the inhalator along the line E-E in FIG. 24b;

FIGS. 26A, 26B, and 26C show, respectively, first side, first side without a cover for the cartridge, and cross-sectional views of an exchangeable inhalator component with a further alternative liquid store system;

FIG. 27 shows a cross section of the inhalator component according to FIG. 26A level with the planar composite;

FIG. 28 shows a section through the liquid store according to FIG. 26A transversely with respect to the planar composite;

FIG. 29A shows a side view of an exchangeable inhalator component with two planar composites arranged next to each other;

FIG. 29B shows a sectional view of the component shown in FIG. 29A, wherein the section runs level with the planar composites.

FIG. 1 shows a first exemplary embodiment of an inhalator according to the invention, which inhalator in the specific example is in the form of a drawing inhalator, and the shape and size of which are configured such that the inhalator can be handled simply and comfortably by users. In terms of volume, the inhalator is only approximately half the size of a cigarette pack. In principle, the inhalator which is illustrated by way of example consists of two parts, namely of an inhalator part 1 and of an inhalator component 2. The inhalator component 2 consists of a housing 3 and comprises, inter alia, a liquid container 4 and a mouthpiece 5 in the manner of a tobacco pipe. The liquid container 4 contains a liquid material which evaporates in the inhalator component 2 and is converted into an inhalable vapor-air mixture or/and condensation aerosol. The vapor-air mixture or/and condensation aerosol formed is offered to the user via the mouthpiece 5. In principle, all substances and preparations which can be evaporated in a substantially residue-free manner under atmospheric conditions are suitable as the liquid material. This condition is even already met if the particular substance or the particular preparation is present in diluted form, for example is dissolved in water or/and ethanol, and the solution evaporates in a substantially residue-free manner. By means of a sufficiently high degree of dilution in an easily volatile solvent, such as ethanol or/and water, even substances which are otherwise difficult to evaporate can meet the abovementioned condition, and thermal decomposition of the liquid material can be avoided or significantly reduced.

The liquid material preferably contains a drug. The aerosol particles produced by condensation generally have a mass median aerodynamic diameter (MMAD) of smaller than 2 μm and, as a result, even reach the alveoli. The inhalator according to the invention is suitable in particular for administering drugs acting systemically, for example drugs which deploy the main effect thereof in the central nervous system. An example is nicotine, the boiling point of which is at 246° C. The aerosol particles containing the drug are predominantly deposited in the alveoli where the drug transfers in a flash into the blood circulation. With reference to the example of nicotine, it should be noted that the latter reaches its target organ—namely the central nervous system—in a focused concentration just approximately 7-10 seconds after inhalation. Of course, the inhalator in question could also be operated without drugs, for example just with aroma substances—and even in the form of nonmedical applications.

As is explained in more detail below, the inhalator part 1 contains at least one energy store and an electric switching circuit, wherein the energy store is protected by a battery cover 6 and the switching circuit by a switching circuit cover 7.

As FIGS. 2A and 2B show, in the specific exemplary embodiment, the inhalator part 1 and the inhalator component 2 are designed so as to be detachable from each other. The detachable coupling consists of a snap connection, formed from two snap-in hooks 8 and two latching lugs 9 interacting therewith. This arrangement makes the inhalator part 1 reusable, this basically being expedient if it is taken into consideration that, firstly, the inhalator part 1 does not come into contact with the liquid material, i.e. is not contaminated by the liquid material, and, secondly, contains components which have a longer life than the parts of the inhalator component 2. After the liquid material in the liquid container 4 has been used up, the inhalator component 2 is as a whole disposed of properly by the user and replaced by a new inhalator component 2. The inhalator component 2 in this respect constitutes an exchangeable disposable article. Proper disposal is appropriate especially if the liquid material contains drugs because condensate residues always form and are deposited in the interior of the housing 3 of the inhalator component 2 over the course of the formation of the vapor-air mixture or/and condensation aerosol. Residues of the liquid material always also remain in the liquid container 4. In principle, of course, it would also be conceivable to design the inhalator part 1 and the inhalator component 2 as a single part, i.e. so as not to be separable from each other. However, this embodiment appears to be more uneconomical because, in this case, all of the parts and components of the inhalator, i.e. the inhalator as a whole, form a disposable article for single use. Of course, the present invention also includes this embodiment, wherein, in this case, the entire inhalator can be interpreted as the inhalator component.

FIGS. 3 to 5 shows various views of the reusable inhalator part 1 with and without a cover. The reusable inhalator 1 is essentially composed of the following three housing parts: the battery cover 6, the switching circuit cover 7 and a support housing 10 arranged in between. For weight reasons, the three housing parts are preferably manufactured from plastic. The support housing 10 conceals the electric switching circuit 11 and the energy store 12 and comprises a partition 13 which separates the switching circuit 11 and the energy store 12 from each other. In the exemplary embodiment, the electric switching circuit 11 is designed as a printed circuit board which is populated on one side and is fastened to the partition 13, for example by an adhesive bonding connection. The energy store 12 preferably consists of a rechargeable battery, for example a lithium-ion battery or a lithium-polymer battery, preferably of flat construction. At present, these types of battery provide the highest energy densities and currents and have been used in diverse forms for a relatively long time, wherein the wide use in cell phones should be mentioned first. Current is supplied from the battery 12 to the printed circuit board 11 via two flat contacts 14 which are soldered onto the rear side of the printed circuit board 11—also see FIG. 10. The flat contacts 14 protrude through two somewhat larger windows in the partition 13. The battery 12 comprises two corresponding contacts (not illustrated) which are pressed against the flat contacts 14, thus producing a detachable electric contact. The compressive force required for this purpose is preferably produced by a leaf spring (not illustrated) arranged between the battery 12 and the battery cover 6. The battery cover 6 is connected detachably to the support housing 10—by means of a screw connection in the exemplary embodiment (see FIG. 1A). Of course, as an alternative, the battery cover 6 could also be designed as a latchable sliding cover. The switching circuit cover 7 is connected, preferably nonseparably, to the support housing 10, for example by means of an adhesive bonding or welding connection. This is intended to counter unauthorized manipulation of the switching circuit 11. In the normally rare event of a switching circuit defect, the entire inhalator part 1 with the exception of the battery 12 should be replaced. Further components and properties of the reusable inhalator part 1 are described in more detail below.

FIGS. 6 and 7 show various views of the exchangeable inhalator component 2. As has already been mentioned, the exchangeable inhalator component 2 is essentially formed by the housing 3, and contains, inter alia, the liquid container 4 and the mouthpiece 5 in the manner of a tobacco pipe. The liquid container 4 and the mouthpiece 5 are connected nonseparably to the housing 3. It is favorable in terms of production to manufacture the liquid container 4 and the mouthpiece 5 as separate parts and only to connect said parts subsequently to the housing 3, for example by an adhesive bonding or welding connection—see FIG. 7A. In principle, of course, it is also conceivable to form the liquid container 4 or/and the mouthpiece 5 integrally with the housing 3. For weight reasons, the housing 3, the liquid container 4 and the mouthpiece 5 are preferably manufactured from plastic, wherein the properties of the liquid material 16 should be taken into consideration when selecting the material for the liquid container 4. If the liquid container 16 contains nicotine, for example, use may be made of plastics as per U.S. Pat. No. 5,167,242 (James E. Turner et al.) and U.S. Pat. No. 6,790,496 (Gustaf Levander et al.).

The liquid container 4 is filled with the liquid material 16 via a filling hole 17, preferably under an inert gas atmosphere, such as argon or nitrogen. A flap-like, openable closure 18 is located on an end side of the liquid container 4 and is opened by the user, by being pressed in, before the inhalator component 2 is used. The openable closure 18 is described in more detail below. The liquid container 4 is never completely filled with the liquid material 16. Complete filling would lead, because of the incompressibility of the liquid material 16, to the flap-like, openable closure 18, which always has a certain degree of elasticity, no longer being pressed in and being left open. After filling has taken place, the filling hole 17 is sealed in an airtight manner by a closure cover 19. The closure cover 19 can be, for example, adhesively bonded on or welded on, wherein a heating effect on the liquid material 16 should be avoided as far as possible. As an alternative, the filling hole 17 can be designed as a capillary bore, and the filling with the liquid material 16 can take place via an injection needle. In this case, the closure cover 19 could be omitted, and the capillary bore itself melted shut. Further components and properties of the exchangeable inhalator component 2 are described in more detail below.

FIG. 8 shows the inhalator according to FIG. 1A with the switching circuit cover 7 lifted off. FIG. 8 shows, inter alia, the snap connection, consisting of the two snap-in hooks 8 and the corresponding latching lugs 9, in the coupled, latched-in state. In this case, the snap-in hooks 8 are designed as extensions of the housing 3 while the latching lugs 9 are formed by contact elements 20. The contact elements 20 are fastened to the support housing 10 of the reusable inhalator part 1 by means of an adhesive bonding connection and carry out yet further functions which will be described in more detail below.

FIGS. 9 to 13 provide more detailed information concerning the inside of the inhalator and the basic operation thereof. According thereto, the housing 3 of the exchangeable inhalator component 2 forms a chamber 21 in the interior. As FIG. 11 shows best, the chamber 21 is passed through by a planar composite 22 according to the invention in the manner of a bridge and therefore in a contact-free manner. The planar composite 22 has a flat shape in the form of a film or strip and consists of a heating element and a wick. The capillary structure of the wick is suitable for absorbing liquid material 16. The heating element and the wick can be formed in extremely diverse ways and can be connected to each other. Exemplary embodiments are described in more detail below. The planar composite 22 is mounted with two end sections on two electrically conductive, plate-like contacts 23, on the surface of which said composite also has an electric contact connection at the same time. The contact connection takes place preferably either by a planar adhesive bonding connection by means of a conductive adhesive—for example adhesives from Epoxy Technology, www.epotek.com—or by a welded connection. In the case of a welded connection, care should be taken to ensure that the wick or the capillary structure thereof is as far as possible not impaired by the welding. If required, the welding should be carried out merely in a spotwise manner. Information has already been provided earlier as regards the selection of material for the plate-like contacts 23.

In the exemplary embodiment, the region between the two plate-like contacts 23 defines that heated section of the planar composite 22 which is arranged in the chamber 21 in a contact-free manner. The arrangement in a contact-free manner results in the heat conduction losses being equal to zero in the thickness direction of the planar composite 22. As a result, said section can heat up to an extent such that the liquid material 16 stored in the wick reaches boiling point and evaporates. According to the invention, the capillary structure of the wick in said section is substantially exposed at least on one side of the planar composite. As is made clear below over the course of the description of exemplary embodiments of the composite, this side is preferably that side 24 of the planar composite 22 which faces away from the plate-like contacts 23. The vapor formed over the course of the evaporation of the liquid material can therefore flow out of the exposed capillary structure of the wick over a large area and without substantial obstruction. In a second refinement of the planar composite, which is likewise described below with reference to examples, the capillary structure of the wick in said section is additionally substantially exposed on that side 25 of the planar composite 22 which is opposite the side 24, and therefore the evaporation surface and consequently also the maximum evaporative capacity which can be obtained doubles in comparison to the case first mentioned. The maximum evaporative capacity which can be obtained is defined by the first occurrence of a boiling crisis in the wick.

The housing 3 furthermore forms an air admission opening for the supply of air from the surroundings into the chamber 21. The supplied air mixes in the chamber 21 with the vapor flowing out of the exposed capillary structure of the wick, over the course of which the vapor-air mixture or/and condensation aerosol is formed. The air admission opening 26 is designed as a slot-shaped channel. The slot-shaped channel is oriented parallel to the planar composite 22. In the exemplary embodiment according to FIG. 10 and FIG. 12, the slot-shaped channel is laterally offset somewhat with respect to the planar composite 22, namely is arranged on that side of the planar composite on which the capillary structure of the wick is substantially exposed. The effect achieved by this arrangement is that the air flowing into the chamber 21 through the slot-shaped channel 26 completely overflows the exposed capillary structure of the wick, and homogeneous mixing conditions can arise. If a constant drawing profile (drawing volume, drawing duration) is presupposed, it is possible, by varying the slot height of the slot-shaped channel 26, to change the flow velocity of the inflowing air, and thereby to influence, within certain limits, the aerosol formation dynamics and, in association therewith, the properties of the aerosol produced. A reduction in the flow velocity allows the aerosol particles to increase on average in size. The geometrical position of the slot-shaped channel with respect to the planar composite 22 also has an influence on the aerosol formation.

FIGS. 13*a* and 13*b* show alternative arrangements of the air admission opening 26: according thereto, the air admission opening 26 in the example according to FIG. 13*a* is formed by two slot-shaped channels 26 which are arranged on opposite sides of the planar composite 22. Air flowing into the chamber 21 therefore flows around the planar composite 22 on both sides. In the example according to FIG. 13*b*, the slot-shaped channel 26 is arranged centrally with respect to the planar composite; in this case, the planar composite 22 lies in the plane of the slot-shaped channel and the inflowing air flows directly onto said composite, wherein the stream of air from the planar composite is divided into two parts, and consequently, as in the previous example, the flow passes around the composite on both sides. The arrangements according to FIGS. 13*a* and 13*b* are suitable especially with that variant embodiment of the planar composite 22 in which the capillary structure of the wick is exposed on both sides, since, in this case, vapor flows off from both sides 24 and 25 of the planar composite 22. However, said arrangements are also suitable for the variant embodiment of the planar composite 22 with the capillary structure exposed only on one side in so far as the second portion of the stream of air, which flows, as it were passively, around the composite, weakens the first portion of the stream of air, which brings about the aerosol formation, and therefore the properties of the aerosol formed can again be influenced.

The air admission opening 26 designed in the form of a slot-shaped channel draws the air out of a plenum chamber 27 which serves to distribute the air uniformly to the slot-shaped channel 26 such that identical flow conditions prevail essentially on all sides in the slot-shaped channel. There is a flow throttle 28 upstream of the plenum chamber 27. The flow throttle 28 has the purpose of producing a flow resistance which is similar to that of a cigarette such that, during drawing, the user feels a similar drawing resistance as when drawing on a cigarette. Specifically, the flow resistance should be within the range of 12-16 mbar at a volumetric flow rate of 1.05 L/min and should have as linear a characteristic as possible. The flow throttle 28 can be formed, for example, from an open-pored sintered compact made of metal or plastic, with the air passing through the pores therein. For example, porous shaped plastic bodies from Porex, www.porex.com, have proven successful in prototypes. In the exemplary embodiment, the plenum chamber 27 is part of the exchangeable inhalator component 2 and the flow throttle 28 is part of the reusable inhalator part 1. In principle, it would also be possible to arrange the plenum chamber 27 and the flow throttle 28 in the exchangeable inhalator component 2, or alternatively to arrange both in the reusable inhalator part 1.

FIG. 10 shows the further course of the air flow upstream of the flow throttle 28. The flow is indicated by arrows. According thereto, the flow throttle 28 draws the air out of a transverse channel 29 which, for its part, opens into the space between the printed circuit board 11 and the switching circuit cover 7. The actual supply of the air from the surroundings takes place via a feed opening 30 formed by the switching circuit cover 7. The feed opening 30 is arranged on that end side of the inhalator which is opposite the mouthpiece 5. This position provides protection at the earliest opportunity against the entry of rainwater.

FIGS. 14a, 14b and 15a, 15b, 15c show exemplary embodiments of the planar composite 22 with reference to cross-sectional illustrations, wherein "cross section" is understood as meaning a section normal to the longitudinal direction of the composite (cf. FIG. 9). Specifically, FIGS. 14a and 14b show embodiments with a capillary structure exposed only on one side while FIGS. 15a to 15c show embodiments in which the capillary structure of the wick is exposed on both sides of the planar composite. According to the embodiment as per FIG. 14a, the planar composite 22 consists of four layers: namely of a metal foil 31 and three metal wire meshes 32 sintered thereon. The metal consists of stainless steel (for example AISI 304 or AISI 316) or of a heating conductor alloy—in particular from the group of NiCr alloys or CrFeAl alloys ("KANTHAL®"). When stainless steel is used, carbon-reduced charges are preferred (for example AISI 304L or AISI 316L) because said charges are less susceptible to intercrystalline corrosion. The metal foil 31 in the stainless steel embodiment can be obtained, for example, from Record Metall-Folien GmbH, www.record-metall.de. The wire mesh can be obtained, for example, by Haver & Boecker, www.haverboecker.com or Sporl KG, www.spoerl.de. The four layers are connected to one another by sintering. The sintering is preferably carried out in vacuo or under inert hydrogen gas. Sinterings of this type belong to the prior art and are routinely carried out, for example, by GKN Sinter Metals Filters GmbH, www.gkn-filters.com and by Sporl KG, www.spoerl.de. The sintering advantageously takes place in the form of a multiple panel; that is to say, relatively large planar panels, for example in the format 200.times.200 mm, are sintered rather than individual planar composites. The individual composites are obtained from the multiple panel after sintering by means of laser cutting or punching and are subsequently optionally etched in an etching bath.

Table 1 shows by way of example the specifications of planar composites 22 used in prototypes.

TABLE 1

| | | |
|---|---|---|
| Metal foil thickness | 10 μm | |
| Metal foil material: | AISI 304 | |
| 1st wire mesh layer: | 36 × 90 μm | Wire diameter × mesh width |
| 2nd wire mesh layer: | 30 × 71 μm | Wire diameter × mesh width |
| 3rd wire mesh layer: | 20 × 53 μm | Wire diameter × mesh width |
| Wire mesh material: | AISI 316L | |
| Composite span: | 14 mm | |
| Composite width: | 2-5 mm | |
| Composite thickness: | 140-160 μm | |
| Etching rate: | Up to 50% | Avesta pickling bath 302*) |
| Porosity: | 65-80% | Depending on the etching rate |

*)Manufacturer: Avesta Finishing Chemicals, www.avestafinishing.com

The composite span corresponds to that section in the chamber 21 which the composite 22 spans in a contact-free manner; in the specific exemplary embodiment, this section corresponds to the distance between the two plate-like contacts 23. The composite span and the composite width have an opposed influence on the resulting heating element resistance. The etching rate defines the mass loss obtained as a whole by the etching. The first wire mesh layer rests directly on the metal foil 31. The third wire mesh layer forms the top layer and at the same time the exposed capillary structure of the planar composite 22. The planar composite 22 is preferably mounted by the metal foil 31 on the plate-like contacts 23. The electric contact connection of the metal foil 31 preferably takes place via a planar adhesive bonding connection between the metal foil 31 and the electrically conductive plate-like contacts 23. In principle, the contact connection could also be produced by a welded connection. A planar composite 22 having a contact connection in such a manner and the specifications as per table 1, with a composite width of 2 mm and an etching rate of 35% has a heating element resistance of approximately 310 mOhm. When heating conductor alloys are used instead of stainless steel, the heating element resistance can be significantly increased; specifically, when DIN material number 2,4872 (NiCr20AlSi) is used, by a factor of 1.8 in comparison to AISI 304/AISI 316, and, when DIN material number 1,4765 (CrAl255) is used, even by a factor of 2.0. In consequence, a planar composite with a composite width of 5 mm in an embodiment with DIN material number 2,4872, but with otherwise identical specifications, would have, as indicated previously, a heating element resistance of approximately 225 mOhm. If energy is supplied on the basis of a lithium-polymer cell with a nominal or idling voltage of 3.7 V and a useful voltage under load of approx. 3.1 V, the current flowing through the planar composite is calculated, on the basis of Ohm's law, at 10 A (for 310 mOhm) or 13.8 A (for 225 mOhm). Said current strength can easily be obtained from current lithium-polymer cells. In a further step, the electric nominal power is calculated, this being at the same time the maximum heating power which can be realized, at 31 W (for 310 mOhm) or 42.7 W (for 225 mOhm). As is also described below, said powers can be reduced arbitrarily by the electric switching circuit 11. In alternative embodiments, the evaporator could also be heated up by induction heat, radiation heat or microwaves instead of by ohmic heat.

On the basis of the previously cited specifications of an exemplary planar composite with a composite width of 5 mm and an etching rate of 35%, the pore volume of the planar composite 22 in the section of the composite span (evaporation section) is calculated at approximately 7.5 µL. This volume is filled by the liquid material 16 to be evaporated and corresponds to the maximum amount of liquid material which can be evaporated per drawing or inhalation (intermittent inhalator operation). If the liquid material contains, for example, nicotine as the drug in a concentration of typically 1.5% by volume, then this theoretically results in a maximum nicotine dose released of 110 µg per evaporation or drawing or, calculated on the basis of 10 inhalations, an overall dose of 1.1 mg. For various reasons, the maximum obtainable dose can actually be somewhat below the calculated values. It is essential, however, that the nicotine doses of current cigarettes (0.1-1.0 mg) can easily be administered by the inhalator according to the invention. It is furthermore essential that the active compound dose can be reduced arbitrarily, either by a reduction in the active compound concentration in the liquid material, or by the selection of a smaller composite width, or by throttling of the heating power supplied by means of the electric switching circuit 11. The latter measure also counteracts thermal decomposition of the liquid material 16, since the composite 22 is not heated up as highly.

It should be noted that both the metal foil 31 and the metal wire mesh 32 sintered onto the foil make a contribution to the electric heating resistor. The electric heating resistor can be interpreted in this respect as a parallel connection of said individual resistors. The capillary action of the wick in interaction with the wire mesh 32 is also established by the metal foil 31, wherein even an individual wire mesh layer in combination with the metal foil 31 can produce a capillary effect. Of course, the invention is not restricted to the previously mentioned specifications. It would also be possible, instead of the metal wire mesh 32, to arrange other open-pored structures made of metal on the metal foil 31; furthermore, a fabric or other open-pored structures made of electrically nonconductive material, for example quartz glass, could also be arranged on the metal foil 31 or fritted thereon.

FIG. 14*b* shows a second exemplary embodiment of a planar composite 22 with a capillary structure exposed only on one side. This embodiment differs from that according to FIG. 14*a* only in that, instead of the outer two wire mesh layers, a fiber composite is provided in the form of a nonwoven fabric which is sintered onto the first wire mesh layer 32. Nonwoven fabrics 33 of this type in the stainless steel embodiment can be manufactured according to customer specification, for example by GKN Sinter Metals Filters GmbH, www.gkn-filters.com. The nonwoven fabric 33 preferably has a thickness of 100-300 µm and a porosity >70%. In comparison to the wire meshes 32, the nonwoven fabric 33 forming the exposed capillary structure of the wick has a significantly larger surface; the larger surface has a favorable effect on the evaporation process. Of course, the nonwoven fabric 33 may also be produced from a heating conductor alloy—in particular from the group of NiCr alloys or CrFeAl alloys ("KANTHAL®"); for this purpose, only the raw fibers forming the nonwoven fabric 33 have to be produced in said material specifications. The planar composite 22 can optionally be re-etched after sintering.

FIG. 15*a* shows an embodiment of a planar composite 22 with a capillary structure exposed on both sides. The planar composite accordingly consists of an open-pored sintered structure formed from a homogeneous, granular, fibrous or flocculent sintered composite 34. The production of thin porous sintered composites has long been known. U.S. Pat. No. 3,433,632 (Raymond J. Elbert) describes, for example, a method for producing thin porous metal plates with a thickness of from 75 µm and a pore diameter of between 1-50 µm. Among other things, powders were processed from nickel and stainless steel (AISI 304). Porosities of up to 60% and, in one variant embodiment with a multi-layered construction, porosities even up to 90% (but only in the top layers) are achieved. U.S. Pat. No. 6,652,804 (Peter Neumann et al.) describes a similar method. JP 2004/332069 (Tsujimoto Tetsushi et al., Mitsubishi Materials Corporation) describes a developed process for producing thin porous sintered composites made of metal in the preferred thickness range of from 50-300 µm, the process being distinguished in that removable fillers, in the specific case acrylic resin spherules, are admixed to the metal powder to be processed. The acrylic resin spherules are spacers which, over the course of a heat treatment, and even before the actual sintering, sublimate at approximately 500° C. in vacuum virtually without any residue and leave behind cavities, which cavities also remain during and after the sintering. By this means, flat composites consisting of stainless steel of the specification AISI 316 L were produced with porosities of typically 70-90%. The Institute for Energy Research (IEF) of the Julich Research Center, www.fz-juelich.de/ief/ief-1 is likewise capable of producing thin porous metal foils of up to a thickness of 500 µm. Like the abovementioned process, the production method is based on the "doctor-blade film casting process".

In principle, all of the abovementioned processes can be used for producing a planar sintered composite 22, 34 according to the invention, with the process according to JP 2004/332069 being preferred because of the high degree of porosity obtained. Care merely has to be taken to ensure that the average pore diameter in the homogeneous sintered composite is as far as possible >10 µm in order to ensure sufficiently rapid infiltration of the wick with the liquid material 16. The grain size of the metal powder to be processed and of the acrylic resin spherules should be tailored to said condition. The preferred thickness range of 50-300 µm, which is cited in the process according to JP 2004/332069, is covered by the thickness range particularly preferred for the planar composite 22.

In addition to processing stainless steel, the abovementioned processes are also suitable for processing pulverulent heating conductor alloys and pulverulent ceramic resistance materials.

FIG. 15*b* shows a development or modification of a planar composite as per the embodiment according to FIG. 15*a* by channels or arteries 35 which are oriented in the longitudinal direction of the composite and the advantageous effects of which have already been described earlier being arranged in the planar composite 22. The production of said channels 35 requires adaptation of the abovementioned production processes by removable threads, for example sublimable acrylic resin threads, being inserted into the film casting slip by oxidation, sublimation or chemical decomposition. The threads are spacers which, upon being removed, leave behind cavities forming channels 35. This is best carried out in three process steps: first of all a first film layer is cast. A layer of threads which are oriented parallel to one another and later form the arteries 35 is placed into said film layer. Finally, a second film layer which at the same time forms the top layer is cast. For better handling, the threads, prior to the application thereof, are clamped into an auxiliary frame. In this modified embodiment, the grain size of the metal powder to be processed and optionally of the acrylic resin spherules is preferably within the range of 1-10 μm while the preferred diameter range of the threads is 20-150 μm. In an optional process step following the film casting and sintering, the planar sintered composite 22, 34 is perforated in the thickness direction, as a result of which holes 36 are formed. The perforation can be carried out, for example, by means of a laser. The grid of holes should be selected to be as nonuniform as possible; this is because, with a uniform grid, the unfavorable situation could occur in which all of the holes 36 come to lie between the arteries 35, and the arteries are not cut. In this case, only some of the advantageous perforation effects, which have already been described earlier, would occur.

To further increase the porosity and the electric resistance, the composites as per the embodiments according to FIGS. 15a and 15b can optionally be re-etched after the sintering. The fastening and contact connection of the planar sintered composite 22, 34 on the plate-like contacts 23 are preferably carried out by means of a welded connection. An adhesive bonding connection is possible only if the adhesive used has a sufficiently pasty or viscous consistency. Otherwise, there would be the risk of the adhesive entering the pore structure of the composite and having an adverse effect on the capillary action of the wick. It may possibly be advantageous to expose the perforation of the composite in the region of the adhesive bonding connection.

FIG. 15c finally shows a further embodiment of a planar composite 22 with a capillary structure which is exposed on both sides. According thereto, the planar composite 22 consists of an open-pored foam 37 formed from an electric resistance material. The production of foam-like composites has long been known. For example, U.S. Pat. No. 3,111,396 (Burton B. Ball) already describes a process for producing metal foams, ceramic foams and graphite foams. The process involves an organic, porous structure being impregnated with a slip containing the foam-forming material, and the organic structure is decomposed over the course of a subsequent heat treatment. In this manner, inter alia, foams consisting of nickel and nickel base alloys have been produced. For a planar composite 22 according to the invention, thin, film-like foams having a thickness within the range of 100-500 μm, a preferred pore diameter within the range of 20-150 μm and a porosity of >70% are required. A foam material of this type in a stainless steel embodiment (for example AISI 316L) can be obtained from Mitsubishi Materials Corporation, www.mmc.co.jp. The starting point in this case is a standard foam material with a thickness of 0.5 mm, a pore diameter within the range of 50-150 μm and a porosity of circa 90%, which material can be compressed arbitrarily in thickness to approximately 100 μm by rolling. The compressed material can subsequently optionally also be sintered. Of course, the compression also results in a reduction in the porosity, but the porosity can be increased again, if required, during a final etching treatment. Although the method for producing the standard foam material is based on processing a slip, it differs from the previously described process according to U.S. Pat. No. 3,111,396 in that the foam is actually formed by a foaming or blowing agent added to the slip. Of course, heating conductor alloys—in particular from the group of NiCr alloys and CrFeAl alloys ("KANTHAL®") can also be processed. The planar composite 22 can consist of a single foam layer or of a plurality of foam layers sintered together. In order to increase the stability and strength of the planar composite 22, the foam 37 can optionally be sintered onto a thin support layer 38, for example onto a wire mesh consisting of stainless steel or a heating conductor alloy. With regard to the fastening and contact connection of the foam 37 on the plate-like contacts 23, the same applies as already explained in conjunction with the embodiments as per FIGS. 15a and 15b. Dunlop Equipment provides dimensionally stable foam material made of Ni or NiCr foam and has a porosity of 90-95% and a pore diameter of approximately 300 μm in plate form up to thicknesses of 15 mm.

All of the previously described embodiments of the planar composite 22 merely constitute exemplary embodiments. The invention is in no way restricted to said exemplary embodiments. For example, a planar foam material could be sintered onto a metal foil. Furthermore, an open-pored, porous deposition layer could be applied to a metal foil—for example following the process according to DE 1,950,439 (Peter Batzies et al.). Finally, of course, the planar composite could also be formed from nonmetallic materials, such as carbon fibers or graphite fibers, for example in the form of woven and nonwoven fabrics, or from quartz glass, for example in the form of a granular or fibrous sintered composite, wherein, in the latter case, a conductive thin layer applied to the glass surface could bring about the electric resistance heating. Quartz glass is distinguished by high chemical resistance and thermal shock resistance.

FIG. 16 and FIG. 16a show an exemplary embodiment of a linear composite 39, wherein, in the present exemplary embodiment, three linear composites 39a, 39b, 39c (39 and 39c are not illustrated, and 39 is used in the description to refer to the linear composite(s) 39a, 39b, 39c generally or collectively) arranged parallel to one another are provided. By means of the provision of a plurality of linear composites, the evaporation surface can be significantly increased in comparison to an individual linear composite, if starting from the same total cross section. The individual composites do not absolutely have to have identical properties. For example, it is possible to assign different heat capacities or/and different heating element properties to the individual composites 39a, 39b, 39c. The resultant effects have already been explained earlier.

In the specific example, the linear composites are designed as wire-shaped sintered composites with an open-pored sintered structure 34. The wire-shaped sintered composites 39a, 39b, 39c are mounted in recesses 108 on the plate-like contacts 23, thus positioning the wire-shaped sintered composites. In the specific exemplary embodiment, the electric contact connection takes place by means of clamping by the wire-shaped sintered composites 39a, 39b, 39c being pressed against the plate-like contacts 23 (see arrow in FIG. 16a) by a ram 40 in the manner of a scaffold. The wire-shaped sintered composites 39a, 39b, 39c are preferably produced by means of an extrusion process, for example as per AU 6,393,173 (Ralph E. Shackleford et al.). AU 6,393,173 describes the production of stainless steel wires having a wire diameter of 0.3-2.0 mm. This diameter range at any rate also covers the preferred diameter range for the linear composite according to the invention. The production process is based specifically on the extrusion of a mixture consisting of a metal powder, a binding agent and a plasticizing agent, and on sintering the extrudate. The metal powder can be in a granular, fibrous or flocculent form. The process has to be adapted in order to obtain an open-pored, porous sintered compact. The adaptation involves a removable filler, for example sublimable acrylic resin spherules, being admixed to said mixture. The acrylic resin spherules are spacers which, over the course of a heat treatment at approximately 500° C. even before the actual sintering, subliminate virtually without any residue and leave behind cavities. The binding and plasticizing agents can optionally be matched to the type and quantity of addition of the filler. The particle size of the metal powder to be processed and of the acrylic resin spherules should be coordinated in such a manner that the average pore diameter of the resulting homogeneous sintered composite is as far as possible >10 µm; this ensures sufficiently rapid infiltration of the wick with the liquid material 16. Of course, instead of stainless steel powder, powders of heating conductor alloys—in particular from the group of NiCr alloys and CrFeAl alloys ("KANTHAL®") can be extruded and sintered in accordance with the process.

It is generally intended for the composites 22 and 39 to be cleaned prior to the installation thereof, and for the surface of the capillary structure to be activated. This measure brings about improved wetting of the composite material by the liquid material 16 and, associated therewith, more rapid infiltration of the wick. In the case of stainless steel, for example, treatment with 20% strength phosphoric acid suffices in order to obtain the previously mentioned effects.

The supplying of the composite 22 and 39 with the liquid material 16 will be described in more detail below. The following embodiments apply equally to planar and linear composites 22, 39, although the figures are restricted to illustrating only one embodiment of the composite. As FIG. 12a and FIG. 17 and also FIG. 16 and FIG. 16a show, one end of the composite 22, 39 projects into a capillary gap 41. The capillary gap 41 feeds the wick of the composite with the liquid material 16; as can be gathered from the figures, the cross section of the capillary gap 41 is larger than the cross section of the composite 22, 39. This has the effect that the liquid material 16 primarily flows through the clear cross section of the capillary gap 41 to the evaporation zone, as a result of which the wick can be infiltrated more rapidly, and the waiting time between two drawings or inhalations can be shortened. The effect acts at least as far as the opening of the capillary gap 41 into the chamber 21. From this point, only the wick of the composite 22, 39 is responsible for transporting the liquid. The capillary gap 41 is basically formed by one of the two plate-like contacts 23 and an upper part 42, which is placed in a planar manner onto said capillary gap, by corresponding recesses forming the capillary gap 41 being incorporated into the upper part 42 and into the plate-like contact 23—see FIG. 12a and FIG. 17. It should be noted that even an individual recess, whether arranged in the upper part 42 or in the plate-like contact 23, would suffice to form a capillary gap 41. When a planar composite 22 is used, it is at any rate advantageous to arrange the recess in the plate-like contact 23 since, in this case, the recess can be used at the same time as a positioning aid for the composite 22. The upper part 42 is joined to the plate-like contact 23 preferably by means of an adhesive bonding connection and is composed of a material which is readily wettable with the liquid material 16, preferably of light metal or of a wettable plastic; the wettability and, moreover, also the adhesive bondability of plastics can be considerably improved by surface activation, for example by a plasma treatment using oxygen as the process gas.

Further upstream, the capillary gap 41 is formed by two thin plates 43 which are arranged parallel to and at a distance from each other (see FIG. 17), wherein one plate is connected to the upper part 42 and the other plate to the plate-like contact 23, preferably by means of an adhesive bonding connection. The plates 43 can be punched, for example, from a stainless steel strip. As FIGS. 18-20 best show, the plates 43 forming the capillary gap 41 project into a reservoir 45 via an extension 44. The reservoir 45 directly adjoins the liquid container 4 and is separated therefrom only by the flap-like, openable closure 18. The openable closure 18 is opened with the aid of a pin 46. The pin 46 is mounted in an axially displaceable manner in the housing 3 and preferably consists of stainless steel. A first end 47 of the pin 46 is directed toward the openable closure 18. When the closure 18 is still closed, a second end 48 projects in the manner of an extension out of the outer surface of the housing 3. The second end 48 of the pin 46 is in ram-like operative connection to one of the two contact elements 20 of the inhalator part 1 by the contact element 20, over the course of the coupling of the inhalator component 2 to the inhalator part 1, being pressed against the second end 48 of the pin 46, and the pin 46 being displaced as a result into the housing 3. The compressive force exerted by the contact element 20 is transmitted from the pin 46 to the openable closure 18. The openable closure 18 has, over the circumference thereof, a material weakening 49 which is dimensioned in such a manner that, upon pressurization by the pin 46, said material weakening tears open over a wide circumferential region in the manner of a predetermined breaking point, but forms a hinge 50 on one side. This has the effect of the openable closure 18 opening in the manner of a flap. The pin 46 has, in the vicinity of the first end 47, a cross-sectional widening 51 which, in the manner of a stop, prevents the pin from being able to slide out of or be removed from the housing 3.

The supplying of the composite 22, 39 with the liquid material 16 will be explained in summary below, wherein FIG. 18 and FIG. 20 illustrate the flow conditions by means of arrows: over the course of the coupling of the inhalator component 2 to the reusable inhalator part 1, the flap-like closure 18 is opened via the pin 46 and, in consequence, the reservoir 45 is flooded by liquid material 16 under the effect of gravitational force. The liquid levels before and after the flooding are shown in FIG. 19. The capillary gap 41 sucks up the liquid material 16 via the extension 44 and supplies said material to the composite 22, 39, as a result of which the wick is finally completely infiltrated with the liquid material 16. The extension 44 which is formed by the plates 43 is intended to avoid gas bubbles which could obstruct the coupling in terms of capillary action from accumulating in the mouth region of the capillary gap 41. Furthermore, a ventilation duct 52 which connects the reservoir 45 to the chamber 21 is incorporated into the plate-like contact 23. The function of the ventilation duct 52 has already been explained earlier. The ventilation duct opens into the chamber 21, preferably at a location upstream of the composite 22, 39, since condensate deposits should scarcely be anticipated in this region of the chamber 21; this is because such condensate deposits could block the ventilation duct 52 or pass via the ventilation duct 52 into the reservoir 45 and contaminate the liquid material 16 stored there. Finally, a buffer store 53 is integrated into the upper part 42—also see FIG. 11 and FIG. 17, the effect of which has likewise already been explained earlier. In the present exemplary embodiment, the buffer store 53 consists of slots 54 which are arranged parallel to one another and are incorporated into the upper part 42. The slots 54 communicate with the capillary gap 41 via openings 55 and with the chamber 21 via a ventilation gap 56. The capillary action of the slots 54 causes the liquid material 16 to flow out of the reservoir 45 via the capillary gap 41 and via the openings 55 into the slots 54 where said material is temporarily stored and can be removed again by the wick as the need arises.

FIGS. 9-12 furthermore show a condensate binding device which is arranged in the chamber 21 and consists of two open-pored, absorbent bodies or sponges 57. The effects of the condensate binding device and the necessity thereof for the inhalator component according to the invention have already been explained in detail earlier. The two sponges 57 are of plate-like design and are arranged at a distance from and parallel to each other, with the composite 22 being covered on both sides by the two sponges 57. A flow duct 58 is formed between the two sponges 57, and the formation of the vapor-air mixture or/and condensation aerosol takes place therein. The main portion of the condensate residues is separated off at the wall sections 59 of the sponges 57, said wall sections forming the flow duct 58, and is immediately sucked up by the open pore structure of the sponges. The sponges 57 are fastened to two opposite walls of the chamber 21, for example by means of an adhesive bonding connection, fill the predominant part of the chamber 21 and are preferably composed of a highly porous and dimensionally stable material which is as fine-pored as possible. This is because, if coarse-pored material is used, there is the risk that, in the event of abrupt movements or accelerations of the inhalator component 2, the capillary forces of the sponge material will no longer be sufficient to retain the liquid condensate, and some of the condensate will be hurled out of the sponges 57. Fiber composites formed from natural or chemical fibers connected to one another thermally or with the aid of a binding agent have proven particularly suitable as the sponge material. Filtrona Richmond Inc., www.filtronaporoustechnologies.com, specializes in the production of fiber composites of this type, with the processing including cellulose acetate fibers bonded by means of triacetin and thermally bonded polyolefin and polyester fibers.

The sponges 57 are arranged somewhat spaced apart from the upper part 42 and from the plate-like contact 23 connected to the upper part 42 such that a gap 60 is formed. The gap 60 ensures that the ventilation duct 52 and the ventilation gap 56 can communicate unhindered with the chamber 21. The sponges 57 should be dimensioned in such a manner that the pore volume thereof is capable of absorbing the anticipated quantity of condensate residues formed. The quantity of condensate depends primarily on the portion in the liquid material 16 of low-boiling fractions with a high vapor pressure and on the air throughput through the air admission opening 26 and through the flow duct 58. If less air is put through, less vapor can be absorbed by the air before being saturated.

As FIGS. 9-10 and FIG. 12 show, a cooler 61 is arranged after the sponges 57 downstream of the composite 22, said cooler, in the specific exemplary embodiment, consisting of a porous filling material 61, through the pores of which the vapor-air mixture or/and condensation aerosol formed can pass. The essential effects of the cooler and filling material 61 have already been explained in detail earlier. The filling material 61 is located in a filling space 62 which is bounded on the flow inlet side by a perforated wall 63, on the flow outlet side by the mouthpiece 5, and on the casing side by the housing 3 and by a wall of the liquid container 4. The perforated wall 63 supports the filling material 61 and at the same time stiffens the housing 3. The perforated wall 63 is arranged spaced apart somewhat from the sponges 57—see FIG. 12. The effect achieved by this is that the vapor-air mixture or/and condensation aerosol emerging from the flow duct 58 can be distributed uniformly over the entire cross section of the filling material 61 even before the perforated wall 63, and the flow passes uniformly through the filling material 61. So that the filling material 61 cannot escape from the holes of the perforated wall 63, a first wire mesh 64 is arranged between the filling material 61 and the perforated wall 63. On the mouthpiece side, the filling material 61 is bounded by a second wire mesh 65 which prevents the filling material from being able to pass into the mouthpiece channel 66 or even into the user's mouth cavity. Between the second wire mesh 65 and the mouthpiece channel 66, the mouthpiece forms a collecting chamber 67 causing the flow also to pass uniformly through the filling material 61 in the end section. The second wire mesh 65 is advantageously fastened directly to the mouthpiece 5, for example is melted onto the latter. During installation, first of all the first wire mesh 64 is placed onto the perforated wall 63. A predefined quantity of filling material 61 is then introduced into the filling space 62, with it also being possible for the filling to take place in multiple stages, and the filling material 61 being compressed in between after each partial filling. This enables a homogeneous filling density to be obtained. As an alternative, the filling material 61 could already be pre-packed outside the inhalator component 2, for example in paper cylinders, with the cross section matched to the filling space 62, and the pack inserted into the filling space 62. Packs of this type can be obtained economically from an endless strand. Finally, the mouthpiece 5 is fitted and the filling space 62 closed.

The filling material can be composed, for example, of a regenerator material. It has proven particularly advantageous, especially if the liquid material 16 contains nicotine, to use tobacco as the filling material 61. In prototypes, excellent results have been obtained in respect of the organoleptic effects of the vapor-air mixture or condensation aerosol administered, on the basis of finely cut tobacco and a filling volume of approximately 7 cm.sup.3. The tobacco can additionally be aromatized by aromatic additives and essential oils, for example tobacco extract, tobacco aroma oils, menthol, coffee extract, tobacco smoke condensate or a volatile aromatic fraction of a tobacco smoke condensate being added thereto. Of course, the invention is not restricted to this selection.

The filling density of the filling material 61 determines the flow resistance offered by the filling material 61 to the vapor-air mixture or condensation aerosol; the filling density should be coordinated with the flow resistance of the flow throttle 28 in such a manner that the resulting flow resistance lies within the range already mentioned of 12-16 mbar at an air throughput of 1.05 L/min. In principle, it is also possible to entirely omit the flow throttle 28, and to produce the desired flow resistance solely by means of the filling material 61 by the filling density thereof being correspondingly increased. In general, however, it should be taken into consideration that a filter effect is undesirable; the aerosol particles produced in the chamber 21 should be able to pass through the filling material 61 as far as possible without loss. The alternative variant embodiment without a flow throttle 28 also has effects on the sensor detection of the beginning of the drawing, which effects will be explained in more detail further on. If the filling material 61 contains tobacco or/and aroma substances, the inhalator component 2 should be stored up to use thereof in an airtight packaging in order to prevent aroma substances from escaping. Even after the inhalator component 2 is coupled to the inhalator part 1, it is possible, by closing the mouthpiece channel 66, for example by means of a cap or a stopper (not illustrated), to substantially prevent aroma substances from escaping and vaporizing and fractions of the liquid material 16 stored in the wick from escaping.

FIGS. 21-22 show a second exemplary embodiment of an inhalator according to the invention, and FIGS. 23A and 23B show an exchangeable inhalator component for said inhalator. In the specific example, the inhalator is designed as a classic inhalator and is based substantially on the arrangement according to FIGS. 9-10, but differs therefrom in that a significantly larger quantity of air can be put through, as a result of which direct inhalation into the lungs is possible in a single step. The inhalator differs from the arrangement according to FIGS. 9-10 specifically in that both the flow throttle 28 and the second open-pored body are omitted, and the mouthpiece channel 66 has a substantially larger cross section. The flow resistance is decisively reduced in this manner. A further essential difference consists in that the main portion of the air put through does not pass the composite 22, 39 at all but rather only flows into the inhalator downstream of said composite. For this purpose, two bypass openings 68, the common cross section of which is substantially larger than the cross section of the air admission opening 26, are arranged on opposite sides of the housing 3 downstream of the composite 22, 39. The two bypass openings 68 are adjoined by two guide vanes 69 which are formed by the housing 3, point in the direction of the mouthpiece channel 66 and strive towards each other, and the free ends or tips 70 thereof form a nozzle-shaped mouth opening 71 through which the vapor-air mixture or/and condensation aerosol formed flows out of the chamber 21 and is subsequently mixed with the air flowing in from the bypass openings 68. The effects of the guide vanes 69 have already been explained earlier. For better mixing of the vapor-air mixture or/and condensation aerosol with the bypass air flowing in through the bypass openings 68, a flow homogenizer 72 can optionally be arranged in the mouthpiece channel 66—see FIG. 22. The flow homogenizer 72 can be manufactured, for example, from a synthetic fiber material in the manner of a nonwoven fabric. Freudenberg Vliesstoffe KG, www.freudenberg-filter.com, provides a material of this type in the form of mats/plates under the name VILEDON®-filter mats. The material can be manufactured in accordance with the customer's specification. In particular, the material properties can be coordinated in such a manner that the final product is very substantially permeable to the fine particles of the condensation aerosol produced, and the flow resistance lies within the desired range already specified earlier. The mats/plates are manufactured from polyolefin fibers (PE, PP) or polyester fibers and can be further processed by punching.

FIGS. 24-25 show an exchangeable inhalator component 2 of an inhalator according to the invention with an alternative liquid container system. Although, in the specific example, the exchangeable inhalator component 2 constitutes an inhalator component for use in a classic inhalator, the alternative liquid container system illustrated can also be used in an inhalator component of a drawing inhalator, as previously described. As the figures show, the liquid container 4 is arranged in the housing 3 so as to be displaceable manually along a displacement axis Y between two stop positions. FIG. 24*b* shows the liquid container 4 in the first stop position which at the same time defines the starting position of said liquid container. The first stop position is defined by a projection 73, which is formed by the mouthpiece 5, in interaction with a catch 74 formed by the liquid container 4. The projection 73 makes it impossible to remove the liquid container 4, which optionally contains drugs or/and poisons, from the inhalator component 2. The catch 74 at the same time secures the liquid container against rotation by the catch 74 engaging in a corresponding groove 75 in the housing 3. In the starting position, an end section of the liquid container 4 projects out of the housing 3 laterally next to the mouthpiece 5. The displaceable liquid container 4 can be displaced in a simple manner into the second stop position thereof by the user pressing the projecting end of the liquid container 4. In the process, the liquid container 4 is displaced by the distance s. The second stop is formed by the upper part 42 and the plate-like contact 23 which is connected thereto. The venting opening 76 and the venting duct 77 prevent interfering air cushions from forming during the displacement operation. On the end side facing the second stop, the liquid container 4 has two openings 78, 79 which are closed on the inside of the container by means of a film seal 80. The capillary gap 41 is substantially identical to the arrangement already described earlier. The plates 43 again form an extension in the form of a first spike 81. The first spike 81 is positioned in such a manner that it is aligned with the first opening 78 and penetrates the latter in the second stop position. The obliquely pointed end of the first spike 81 at the same time cuts through the film seal 80 and enters into contact with the liquid material 16, as a result of which finally the coupling in terms of capillary action to the capillary gap 41 is produced. The spike behaves in the same manner with the ventilation duct 52: in contrast to the arrangement described earlier, in the specific exemplary embodiment said ventilation duct is integrated into the upper part 42 and, like the capillary gap 41, forms an extension or second spike 82 at the end facing the liquid container 4, said extension or spike being positioned so as to be aligned with the second opening 79 in the liquid container 4 and to pass through said opening in the second stop position. The second end of the ventilation duct communicates in turn with the chamber 21 (not illustrated). The supplying of the composite 22, 39 with the liquid material 16 functions in precisely the same manner as already described earlier. In the delivery state of the inhalator component 2, the liquid container 4 is in the starting position thereof, i.e. in the first stop position. The liquid container 4 is preferably displaced into the second stop position and coupled to the capillary gap 41 only shortly before use of the inhalator component 2. In order to prevent a premature, unintentional coupling, the liquid container 4 is fixed in the starting position thereof. The fixing can take place, as FIG. 24*b* shows, for example by means of a small semicircular locking plate 109 which is connected via microwebs 83 to the liquid container 4 and to the housing 3. The small locking plate 109 thereby produces a rigid connection between the liquid container 4 and the housing 3. By means of manual application of force to the small locking plate 109—for example by repeated bending thereof—the microwebs 83 can be broken and the fixing of the liquid container 4 undone. As an alternative, the liquid container 4 can be fixed in a simple manner by means of an adhesive tape (not illustrated). Information has already been provided earlier with regard to the selection of material for the liquid container 4, said information applying equally to the specific exemplary embodiment.

FIGS. 26-27 show an exchangeable inhalator component 2 of an inhalator according to the invention with a further alternative liquid storage system. Although, in the specific example, the exchangeable inhalator component 2 constitutes an inhalator component for use in a classic inhalator, the alternative liquid storage system illustrated can also be used in an inhalator component of a drawing inhalator, as described earlier. In the specific exemplary embodiment, the liquid store contains an open-pored foam 84 which is impregnated with the liquid material 16. The composite 22, 39 is clamped in the manner of a sandwich between the foam 84 and one of the two plate-like contacts 23, as a result of which the wick is coupled in terms of capillary action to the liquid material 16. The foam 84 is held by a cartridge housing 85, together with which the foam forms an exchangeable cartridge 86. The cartridge 86 is inserted into a corresponding recess 87 in the housing 3. The recess 87 is sealed in an airtight manner to the outside by a cover 88. The cover 88 is fixed to the housing 3 by means of a snap connection 89. This fixing also causes the cover 88 to exert a compressive force on the cartridge 86 in the direction of the composite 22, 39. As FIG. 28 shows in more detail, the composite 22, 39 is mounted on an elevation 90 of the plate-like contact 23. The elevation 90 together with the compressive force acting on the cartridge causes compression of the foam 84—see compression stroke h. The compression has the effect that a small quantity of the liquid material 16 is pressed out of the foam 84 in the contact region with the composite, which quantity suffices to ensure coupling in terms of capillary action between a newly inserted cartridge 86 and the wick. The cartridge housing 85 is perforated on the side facing the cover 88. The ventilation holes 91 communicate with the chamber 21 via a cutout 92 in the cover 88 and thereby compensate for the pressure between the liquid material 16 bound in the pores of the foam 84 and the chamber 21. The foam 84 preferably consists of a fine-pored polyether-polyurethane foam material which can be additionally compressed. In prototypes, foam material compressed two to three times and having the name "Jet 6" from the manufacturer Fritz Nauer AG, www-.foampartner.com has been successfully used. The liquid storage system just illustrated has the disadvantage that the cartridge 86 can be removed from the inhalator component 2. This is, of course, associated with risks, for example the risk of the relatively small cartridge 86 being swallowed by small children. The liquid storage system is therefore not suitable for storing drugs or/and poisons, for example nicotine.

Further general parts of the inhalator according to the invention, which parts are present in all of the exemplary embodiments, will be described in more detail below: as FIGS. 6A-6C, FIG. 9 and FIG. 19 show, the plate-like contacts 23 of the exchangeable inhalator component 2 protrude out of the outer surface of the housing 3 in the form of two plug contacts 93. Over the course of the coupling of the inhalator component 2 to the inhalator part 1, the plug contacts 93 together with corresponding spring contacts 94 form electric contacts via which the electric energy for evaporating the liquid material 16 is supplied to the heating element. The spring contacts 94 are part of the contact elements 20 and are connected to the latter, preferably by a welded connection—also see FIGS. 4-5. The contact elements 20 are preferably composed of a metallic contact material and can be manufactured, for example, by Ami Doduco GmbH, www.amidoduco.com. In the event that the same or similar material as for the heating element, for example stainless steel, is used for the reasons already mentioned for the plate-like contacts 23, it is necessary, due to the inadequate conductivity of said material, to cover the plate-like contacts 23, at least in the region of the plug contacts 93, for example galvanically, with a conductive layer of gold, silver, palladium or/and nickel, thus substantially reducing the electric contact resistance. The contact elements 20 obtain the electric energy via two wires which connect the contact elements 20 to the printed circuit board 11—see FIGS. 4-5. The wires 95 are preferably fastened on both sides by means of soldering. In summary, it should be pointed out once again that the contact elements 20 carry out up to three different tasks: firstly, as just described previously, they transmit the electric energy from the printed circuit board 11 to the plate-like contacts 23. Secondly, they form lateral latching lugs 9 which interact with the snap-in hooks 8 of the housing 3, thus bringing about snap connection between the inhalator component 2 and the inhalator part 1. Thirdly, one of the two contact elements 20 forms a stop for the pin 46, thus producing the ram-like operative connection for opening the liquid container 4. The latter task appears only in a variant embodiment of the inhalator and the liquid container system thereof.

For the positionally precise coupling of the inhalator component 2 to the inhalator part 1, a positioning device is provided which consists of a sintering projection 96 arranged on the support housing 10 and of a centering recess 97 which corresponds to said sintering projection and is arranged on the housing 3—see FIGS. 3A-3C, FIGS. 6A-6C, FIG. 10 and FIG. 12. The centering projection 96 has two venting holes 98 which vent the centering recess 97 during the coupling.

FIGS. 29A and 29B show an exchangeable inhalator component 2 of an inhalator according to the invention, which inhalator component differs from the inhalator components previously illustrated by having two planar composites 22a and 22b arranged next to each other. The planar composites 22a and 22b can be constructed, for example, as already described in detail in FIGS. 14-15. The planar composites 22a and 22b and the heating resistors thereof are electrically connected to one another in series. The series connection causes the resulting heating resistance to double given an unchanged composite span, if identically sized individual resistances of the composites 22a and 22b are taken as a basis. The advantageous effects of said increase in resistance have already been explained earlier. In principle, the heating resistance of the composite could also be increased by enlarging the composite span. However, this would have highly disadvantageous effects on the infiltration duration which is the duration required by the liquid material 16 in order to completely infiltrate the wick again following evaporation. The infiltration duration would increase abruptly. If, by way of example, the composite specifications according to table 1 are taken as the starting point, and two composites 22a and 22b having a composite width of in each case 4 mm and an etching rate of 25% are connected in series, this results in a heating element resistance of approximately 275 mOhm. At this resistance value, it is appropriate to reduce the composite span even further with regard to a short infiltration period, for example to 12 mm, as result of which the heating element resistance will drop to a value of approximately 235 mOhm. The two composites 22a and 22b can optionally also have different resistance values, which can be realized in an extremely simple manner by different composite widths being assigned to the two composites. This enables the evaporation process to be spatially varied. Furthermore, the two composites 22a and 22b can optionally be fed by different sources of liquid material. By means of the latter two refinement options, it is possible still to have targeted influence on the aerosol formation process and ultimately on the properties of the condensation aerosol formed. For example, the evaporation process in the distillation zone of a cigarette can thereby be approximately simulated in space and time.

The composites 22a and 22b are mounted in turn with the end sections thereof on electrically conductive, plate-like contacts, and the heating elements thereof are in contact connection electrically with the contacts. In contrast to the exemplary embodiments described earlier, the plate-like contacts are split on one side into two contact parts 23a and 23b which are insulated electrically from each other. The first planar composite 22a is mounted with an end section on the contact part 23a, and the second planar composite 22b is mounted with an end section on the contact part 23b. On the opposite side, the two composites 22a and 22b are mounted with the end sections thereof on a common plate-like contact 23c. The plate-like contact 23c connects the two composites 22a and 22b electrically to each other. The plate-like contact 23c brings about the actual electric series connection while the electric energy is supplied to the composites 22a and 22b via the contact parts 23a and 23b. The electric coupling to the reusable inhalator part 1 takes place again via the plug contacts 93, the arrangement of which is identical to the coupling scheme of the previously illustrated exemplary embodiments, cf. FIGS. 6A-6C, FIG. 9 and FIG. 19. In order to be able to maintain said coupling scheme, in the specific exemplary embodiment the contact part 23a is configured such that it extends transversely through the housing 3 to the opposite side of the inhalator component 2 via a connecting web 110. As FIG. 29A shows, the connecting web 110 runs below the slot-shaped channel 26. Instead of the connecting web 110, as an alternative a wire could also produce the electric connection. Furthermore, it would alternatively also be possible to lead the two plug contacts 93 out of the housing on the same housing side, with that side on which the contact parts 23a and 23b are also arranged obviously being appropriate here. Finally, it should also be mentioned that the plate-like contacts or contact parts 23a, 23b and 23c can also be formed by printed circuit boards or by an individual common printed circuit board. Thick copper printed circuit boards having copper layer thicknesses in the range of 100-500 µm are preferred because of better heat dissipation. Good heat dissipation should be ensured especially in the region of the capillary gap 41 in order to prevent boiling of the liquid material 16 in the capillary gap 41.

The sensor 99, 100—see FIG. 8, FIG. 18 and FIGS. 21-22—forms a substantial part of the inhalator according to the invention. The sensor 99, 100 has the task of detecting the beginning of drawing or inhalation, whereupon the electric switching circuit 11 actives the supply of electric energy to the heating element of the composite 22, 39 and initiates the evaporation of the liquid material 16. At least two different types of sensors can be used: in the exemplary embodiment according to FIG. 8, the sensor consists of a pressure sensor 99. The pressure sensor 99 is adhesively bonded into the support housing 10, and the electric connections or pins 101 thereof are soldered directly on the printed circuit board 11. The pressure sensor 99 communicates with the plenum chamber 27 via a bore 102 and measures or monitors the negative pressure in the plenum chamber 27—see FIG. 18. An example of a suitable pressure sensor 99 is the CPCL04GC type with a measuring range of +/−10 mbar from the manufacturer Honeywell Inc., www.honeywell.com. The abovementioned sensor consists substantially of a zero-calibrated and temperature-compensated measuring bridge and can be connected to the printed circuit board 11 as follows: the negative sensor output is grounded via a high ohmic resistance having a defined resistance value—for example 2.2 MOhm, as a result of which the output signal or measuring signal of the pressure sensor 99 is slightly distorted, or in other words, worded, the offset of the measuring bridge is calibrated to a defined value. The distortion or the offset predetermines a switching threshold which corresponds to a certain pressure threshold value. The measuring signal prepared in this manner is connected across to the input of a precision operation booster 103, which is connected in the form of a comparator—for example of the LTC1049CS8 type from the manufacturer Linear Technology Inc., www.linear.com. This connection results in an output signal which rapidly and exactly depicts the beginning of drawing in digital form. The pressure sensor 99 is suitable especially for use in drawing inhalators, if a flow throttle 28 is arranged upstream of the plenum chamber 27. In this case, a negative pressure typically lying within the range of 0-50 mbar with respect to the surroundings occurs in the plenum chamber 27 over the course of drawing. The pressure profile is approximately in the shape of a bell. The beginning of drawing can be detected in a simple manner by, as previously described, predetermining a pressure threshold value which is constantly compared with the actually measured value. The beginning of drawing can be defined as the first time the pressure threshold value is exceeded. Expediently, a value within the range of 0.2-5 mbar is selected for the pressure threshold value. If a lower pressure threshold value is selected, the drawing identification responds more rapidly. A lower limit is defined by the specifications of the pressure sensor and operation booster used in each case.

If there is no flow throttle 28 in the inhalator, ambient pressure virtually prevails in the plenum chamber 27. The exemplary embodiment according to FIGS. 21-22 has these requirements. The classic inhalator illustrated operates approximately under atmospheric pressure conditions and permits direct inhalation into the lungs in a single step. In this case, it is more expedient to detect the beginning of inhalation by means of a flow sensor 100. In the exemplary embodiment according to FIGS. 21-22, the flow sensor 100 is arranged in the transverse channel 29, and the connections or pins 101 of said flow sensor are again soldered directly on the printed circuit board 11. A thermistor 100, preferably of the GR015 type from the manufacturer Betatherm Corporation, www.betatherm.com, is suitable as the flow sensor 100. The thermistor 100 is connected on the printed circuit board 11 to a measuring bridge (not illustrated). For temperature compensation purposes, the measuring bridge contains a second thermistor of identical type and is calibrated to a defined offset threshold value by means of precision resistors. The output signal of the measuring bridge is then again connected across to the input of an operation booster 103, which is connected in the form of a comparator. In the state of equilibrium, the two thermistors are at the same temperature level—typically within the range of 80-200° C., depending on the dissipated power. If a user then begins with the inhalation, air flows through the transverse channel 29. The air cools the thermistor 100, thus increasing the resistance thereof. The change in resistance is processed by the measuring bridge. At the moment at which the output signal of the measuring bridge passes through zero, the comparator 103 tilts and emits a digital signal indicating the beginning of inhalation.

The signals output by the sensors 99, 100 and the connections thereof are preferably further processed in an integrated switching circuit 104—see FIG. 8 and FIG. 21. The integrated switching circuit 104 may also be a microprocessor. The integrated switching circuit 104 processes a large part of all of the electric signals of the inhalator and carries out the control operations essential for operating the inhalator. These control operations will be explained in more detail below: a central control operation constitutes the supply of electric energy to the heating element of the composite 22, 39. The electric energy is supplied by the energy store 12. On the basis of the current prior art, lithium-polymer and lithium-ion cells are particularly appropriate as energy stores 12 owing to the high energy and power density thereof. In the event of metallic heating elements, even an individual lithium-polymer cell or lithium-ion cell with an idling or nominal voltage of approximately 3.7 V suffices. The energy and power supply to the heating element of the composite 22, 39 can be controlled in a simple manner by the battery voltage being chopped with a variable level control degree over the duration of the supply of energy, and the resultant useful voltage being applied to the heating element. The resulting useful voltage is a square wave signal having a variable duty cycle. Apart from low voltage losses, the amplitude of the square wave signal corresponds to the battery voltage. The actual chopping preferably takes place by means of a power MOSFET 105, for example the IRF6635 type from the manufacturer International Rectifier, www.irf.com, which is suitable for switching very high currents with a minimum drain-source forward resistance. In this case, the integrated switching circuit 104 controls the gate of the power MOSFET 105. A very simple control strategy which has moreover also proven successful in prototypes according to the invention consists in dividing the duration of the supply of energy into two periods—into a heating-up period and a following evaporation period. In the intermittent operation of the inhalator, synchronous with inhalation or drawing, the duration of the supply of energy is oriented to the drawing or inhalation duration. In the case of drawing inhalators, for example, the starting point can be an average drawing duration of approximately 2.1 sec (+/−0.4 sec). The same value approximately also applies to cigarettes. If it is taken into consideration that, even after the supply of energy is switched off, a certain degree of reevaporation takes place because of the heat still stored in the composite 22, 39, it appears to be expedient to select the duration of the supply of energy to be somewhat shorter, for example a value within the range of 1.5-1.8 sec. In the case of classic inhalators, it may be advantageous within the context of a high degree of drug absorption in the alveoli to reduce the duration of the supply of energy even further. This is because drawing inhalators have the advantage over classic inhalators that the drug is located as it were at the very front of the air column inhaled into the lungs, as a result of which the drug can more easily penetrate as far as the alveoli. By contrast, in classic inhalators, the drug passes directly into the inhaled air column. It should be taken into consideration in this case that one end section of the inhaled air column serves only to fill the "functional dead space" (approx. 150-200 mL) of the respiratory system. Portions of drug in said dead space at any rate no longer reach the alveoli and are lost in this respect for a rapid, systemic action. If it is furthermore taken into consideration that the inhalation duration greatly fluctuates individually, namely approximately between 1.5-3 sec, it appears to be expedient to select a value <1.5 sec for the duration of the supply of energy in classic inhalators. During the first of the two periods previously mentioned—the heating-up period—the composite 22, 39 together with the liquid material 16 stored in the wick is heated up by the heating element. The evaporation of the liquid material 16 is initiated only when the temperature of the composite 22, 39 has approximately reached the boiling range of the low-boiling fractions of the liquid material 16. The heating-up period should therefore be as short as possible. It is obvious in this respect that the battery voltage should be passed on to the heating element in this period unchopped or with a level control degree or duty cycle of 100%. The duration of the heating-up period depends especially on the specifications of the composite 22, 39 and on the quantity and composition of the liquid material 16 to be evaporated and should be as far as possible <0.5 sec. In the subsequent second period—the evaporation period—the level control degree is substantially withdrawn, and the actual evaporation of the liquid material 16 takes place. In said second period, the supplied energy is used primarily to evaporate the liquid material 16 and secondarily to cover energy losses. By means of appropriate selection of the level control degree, the evaporative capacity and therefore the quantity of liquid material 16 evaporated per drawing or inhalation can be controlled within certain limits. An upper limit is imposed by the occurrence of a boiling crisis and by local drying out and overheating of the wick. In contrast, thermal decomposition of the liquid material 16 can be counteracted by withdrawing or throttling the level control degree.

The control strategy just described can be expanded and refined arbitrarily: for example, it may be expedient also to take the state of the battery into consideration in the control strategy, since the battery voltage significantly drops with increasing discharge and increasing age of the battery, especially under load. This effect can be countered by an increase in the level control degree. In order to be able to carry out this correction even in the heating-up period, it is expedient to drive the battery voltage of a new, charged battery only at 80%, for example, rather than at 100% as proposed earlier, and therefore there is still a sufficient amount of room for adaptation.

In addition, the control of the supply of energy to the heating element of the composite 22, 39 requires various auxiliary operations: for example, provision has to be made for the supply of energy not to be immediately activated again after the end of an evaporation cycle. On the contrary, a waiting time should be maintained leaving sufficient time for the liquid material 16 to completely infiltrate the wick again. The minimum waiting time required depends on the particular specifications of the composite and on the viscosity of the liquid material. In prototypes, it could be shown and calculations could confirm that, given an appropriate configuration, complete infiltration of the wick can be obtained in less than 10 sec. A compulsory waiting time of this order of magnitude should be tolerated by most users, especially if it is taken into consideration that the interval between two drawings is on average 25 sec in the case of a cigarette. A waiting time of this type should also be maintained after coupling a new inhalator component 2 to the inhalator part 1. Another auxiliary operation involves the supply of energy to the heating element being broken off immediately if the user prematurely breaks off the drawing or inhalation. This prevents vapor from unnecessarily being formed in the chamber 21.

A further control operation of the integrated switching circuit 104 relates to the user interface, i.e. communication with the user. The sensor 99, 100 for identifying the beginning of drawing or inhalation constitutes an input interface and is indispensable as such. Furthermore, in a very simple refinement of the user interface, no further input interface is provided, not even an on-off switch, and therefore the use of the inhalator turns out to be extremely uncomplicated. Of course, the lack of an on-off switch presupposes that the electric switching circuit 11 requires an appropriately small amount of current, which should be taken into consideration when preparing the circuit diagram. For example provision may be made for the switching circuit 11 to switch into a particularly energy-saving sleep mode if an inhalator component 2 is not coupled to the inhalator part 1. As output interfaces, use may be made, for example, of two light-emitting diodes 106, the first of which shows the charging state of the battery 12, and the second of which signals the approaching changeover interval of the inhalator component 2. The changeover interval of the inhalator component 2 can be monitored by a counter which counts the number of drawings or inhalations. During the interchanging of the inhalator component 2, the counter is reset to zero, with use being made of the fact that the heating element resistance is infinitely large for a moment. In a somewhat more complicated refinement, instead of the light-emitting diodes 106, a display (not illustrated) can be integrated in the switching circuit cover 7. In addition to the battery charging state and the approaching changing over of the inhalator component 2, the display can also indicate further operating states and information, for example the drug dose supplied as a whole for a certain period of time. In the case of nicotine, it makes it possible in a highly objective manner to ascertain the degree of nicotine dependency of the user and, over the course of a gradual withdrawal, to ascertain the success actually obtained. Finally, the display can assist the user in the form of a user guide for operating the inhalator. It is also possible to provide as an output interface an acoustic, vibratory or/and optical alarm which assists the user in supplying the particular drug at the correct time and in the required dose. Finally, a data interface may also be provided, for example in the form of a USB or Bluetooth interface, via which in particular firmware and software updates are merged, diagnosis functions are carried out and information, in particular relating to the drug dose administered, can be read. By means of the latter function, a doctor carrying out the treatment can exactly and objectively record and evaluate the drug dose supplied over a prolonged period and the temporal profile of said dose, and can coordinate his medicinal treatment thereto.

A further control operation which can optionally be provided relates to the identification of the inhalator component 2 used, the identification of the user and, associated therewith, the ascertaining of misuse of the inhalator. The inhalator component 2 together with the type of composite and liquid material 16 contained therein can be identified in a simple manner by measuring the heating element resistance. However, this method has certain limits because each drug preparation has to be assigned a certain type of composite with a defined heating element resistance. A somewhat more complicated method involves arranging an identification chip (not illustrated) in the inhalator component 2, said identification chip unambiguously identifying the inhalator component 2. With the aid of a chip of this type, it is possible to unambiguously identify each individual inhalator component 2 produced and sold. The chip is preferably arranged on one of the two plate-like contacts 23, with it being particularly favorable if the plate-like contact 23 is formed by a printed circuit board. The information stored in the chip is read by an integrated switching circuit 104 which, in this case, preferably consists of a microprocessor. On the basis of the information read, the microprocessor 104 selects the operating parameters suitable for the inhalator component 2 used. Furthermore, after reaching the changeover interval, the microprocessor 104 can block the particular inhalator component 2 or render the latter unusable by certain means such that no further drawings or inhalations can be carried out with said inhalator component 2. This measure serves especially to avoid misuse of the inhalator component 2. Misuse of this type would involve, for example, a user attempting to continue to use the inhalator component 2 beyond the changeover interval by, for example, forcibly opening the liquid container 4 and refilling the latter with liquid material 16 himself. In the case of nicotine, the lethal dose (LD50) is circa 0.5-1.0 mg/kg of body weight. It can be imagined how hazardous such a misuse would be for the user and his environment. The risk of misuse of this type and the environmental hazard due to used inhalator components 2 which have been thrown away can be further reduced by the inhalator component 2 being sold under the deposit system. The identification of the user serves to prevent the inhalator being used by an unauthorized third party and thereby also prevents theft. The user can be identified, for example, via a touch display by inputting a code, or biometrically by means of a fingerprint.

A further control operation which can be carried out by the integrated switching circuit 104 relates to the cell and charging management of the battery 12. Since switching circuits which are already integrated are available commercially for this purpose, said control operation may alternatively also take place in a separate integrated switching circuit. The charging current is supplied via the charging plug 107 which is arranged on that end side of the inhalator part 1 which faces away from the mouthpiece 5—see FIGS. 3A-3C and FIG. 8. The charging plug 107 may at the same time be a diagnostic plug via which the electric switching circuit 11 and the heating element resistance of the composite 22, 39 can be checked by means of an external analyzer and possible errors can be detected.

The previously described control operations can be converted into a circuit diagram by a person skilled in the art in this field using known methods, and will therefore not be described in more detail in this context.

Finally, the functioning and operation of the inhalator according to the invention will be explained once again in summary: the user makes a new inhalator component 2 ready for use by coupling the latter to the reusable inhalator part 1 via the snap connection 8, 9. In the exemplary embodiment according to FIGS. 6A-6C, the liquid container 4 is opened synchronously to the coupling to the inhalator part 1 by means of the pin 46 in interaction with the contact element (see FIG. 19). By contrast, in the exemplary embodiment according to FIG. 24a and FIG. 24b, the liquid container 4 is opened by the user displacing the liquid container 4 into the housing 3 (see arrow direction). In both cases, one end of the capillary gap 41, which end is designed as an extension 44 (FIG. 19) or as a first spike 81 (FIG. 25), is wetted with the liquid material 16. The capillary gap 41 exerts a capillary force on the wetting liquid material 16, said capillary force causing the capillary gap 41 to be rapidly flooded. The liquid material 16 reaches the composite 22, 39 (see FIG. 11). The composite 22, 39 consists of a wick and an electric heating element. The capillary forces in the wick cause the latter to be infiltrated likewise rapidly by the liquid material 16. At the same time, the buffer store 53 consisting of capillaries 54 is also flooded by the liquid material 16. The buffer store 53 permits position-independent operation of the inhalator. The duration between the opening of the liquid container 4 and complete infiltration of the wick corresponds to a compulsory waiting time for the user and, given an appropriate configuration, is at any rate less than 10 sec. The inhalator is now ready for operation. In the case of a drawing inhalator according to the invention (FIGS. 9-10), the user carries out drawing via the mouthpiece 5 in a similar manner as for a cigarette and, in the case of a classic inhalator according to the invention (FIGS. 21-22), the user carries out direct inhalation into the lungs. The sensor 99, 100 (FIG. 8 and FIG. 21) detects the beginning of drawing or inhalation and leads to the integrated switching circuit 104 supplying the heating element of the composite 22, 39 with electric energy in accordance with a predetermined control strategy. This results in the composite 22, 39 heating up rapidly and evaporating the liquid material 16 in the wick. The vapor formed leaves the composite 22, 39 via the wick surface, which is exposed over wide regions of the composite, and mixes in the chamber 21 with the air flowing into the chamber 21 through the air inlet opening 26. By mixing with the air, the vapor cools and forms a condensation aerosol (FIGS. 9-10 and FIGS. 21-22). Excess condensate which does not contribute to forming the condensation aerosol or vapor-air mixture is sucked up and bound by sponges 57 arranged in the chamber 21. In the exemplary embodiment according to FIGS. 9-10 (drawing inhalator), the vapor-air mixture or/and condensation aerosol formed, in order to improve the organoleptic properties thereof, also flows through the filling material 61 before finally entering the user's mouth cavity via the mouthpiece channel 66. In the exemplary embodiment according to FIGS. 21-22 (classic inhalator), the vapor-air mixture or/and condensation aerosol formed emerges out of the chamber 21 through the mouth opening 71 formed by the guide vanes 69 and is combined with the bypass air flowing through the bypass openings 68 in order finally, after flowing through a flow homogenizer 72 optionally arranged in the mouthpiece channel 66, likewise to enter the user's mouth cavity. After a waiting time of a few seconds, the liquid material 16 has again completely infiltrated the wick of the composite 22, 39, and the inhalator is ready for further inhalation. If the liquid container 4 contains, for example, 2.5 mL of effectively useable liquid material 16, and if the liquid material contains nicotine as the drug in a concentration of typically 1.5% by vol., then with an inhalator component of this type up to 380 drawings or inhalations can be carried out if 100 µg of nicotine is evaporated per inhalation. 380 drawings corresponds approximately to 38 cigarettes. If only 50 µg of nicotine is evaporated per inhalation, then the range extends to 760 inhalations, which value approximately corresponds to four packs of cigarettes.

Finally, with reference to the drug nicotine, an exemplary preparation of the liquid material 16 should be disclosed, which preparation is evaporated in prototypes according to the invention configured as drawing inhalators. With regard to the pharmacological, pharmacokinetic and organoleptic effects, the condensation aerosol formed and administered in this case came very close to the smoke of a conventional cigarette. All of the listed contents are also found again in cigarette smoke.

TABLE 2

Exemplary drug preparation on the basis of nicotine

| Substance | CAS number | % by mass |
|---|---|---|
| Ethanol | 64-7-5 | 68.80 |
| Water | 7732-18-5 | 16.50 |
| Glycerol | 56-81-5 | 9.10 |
| Nicotine | 54-11-5 | 1.80 |
| Lactic acid | 50-21-5 | 0.23 |
| Succinic acid | 110-15-6 | 0.28 |
| Levulinic acid | 123-76-2 | 0.46 |
| Benzoic acid | 65-85-0 | 0.08 |
| Phenyl acetic acid | 103-82-2 | 0.08 |
| Acetic acid | 64-19-7 | 1.67 |
| Formic acid | 64-18-6 | 0.53 |
| Propionic acid | 79-09-4 | 0.27 |
| Solanone | 1937-54-8 | 0.05 |
| Tobacco aroma oils | *) | 0.15 |
| Ambroxide | 6790-58-5 | optional |
| Menthol | 2216-51-5 | optional |
|  | Total: | 100.00 |

For the sake of completeness, it should furthermore also be noted that it is possible to integrate additional functions in the inhalator according to the invention, said functions going beyond the actual task of the inhalator and expanding the inhalator into a multifunctional appliance or hybrid appliance. Functions of this type may include, for example: a clock, mobile data store, player functions (including dictation function), PDA functions, navigation aid (GPS), cell telephony and photography.

In an embodiment, an inhalator component for an inhalator device, for the intermittent formation, synchronous with inhalation or drawing, of at least one of a vapor air mixture or a condensation aerosol, comprises a housing; a chamber arranged in the housing; an air admission opening for the supply of air from the surroundings to the chamber; an electric heating element for evaporating a portion of a liquid material, wherein a vapor that is formed is mixed in the chamber with the air supplied through the air admission opening to form the at least one of the vapor air mixture or condensation aerosol; and a wick with a capillary structure, wherein the wick forms a composite with the heating element and automatically resupplies the heating element with the liquid material following evaporation, wherein the composite has a thickness of less than 0.6 millimeters (mm). In another embodiment, the composite has a thickness of less than 0.3 mm.

In an embodiment, an inhalator component for an inhalator device, for the intermittent formation, synchronous with inhalation or drawing, of at least one of a vapor air mixture or a condensation aerosol, comprises a housing; a chamber arranged in the housing; an air admission opening for the supply of air from the surroundings to the chamber; an electric heating element for evaporating a portion of a liquid material, wherein a vapor that is formed is mixed in the chamber with the air supplied through the air admission opening to form the at least one of the vapor air mixture or condensation aerosol; and a wick with a capillary structure, wherein the wick forms a composite with the heating element and automatically resupplies the heating element with the liquid material following evaporation, wherein the composite has a porosity of greater than 50%. In another embodiment, the composite has a porosity of greater than 70%. In yet another embodiment, the composite has a porosity of greater than 90%.

In an embodiment, an inhalator component for an inhalator device, for the intermittent formation, synchronous with inhalation or drawing, of at least one of a vapor air mixture or a condensation aerosol, comprises a housing; a chamber arranged in the housing; an air admission opening for the supply of air from the surroundings to the chamber; an electric heating element for evaporating a portion of a liquid material, wherein a vapor that is formed is mixed in the chamber with the air supplied through the air admission opening to form the at least one of the vapor air mixture or condensation aerosol; and a wick with a capillary structure, wherein the wick forms a composite with the heating element and automatically resupplies the heating element with the liquid material following evaporation, wherein the composite has an open-pored sintered structure. In other embodiments, the open-pored sintered structure comprises a fibrous sintered structure, a granular sintered structure, or a mesh. The mesh can comprise stainless steel.

In an embodiment, an inhalator component for an inhalator device, for the intermittent formation, synchronous with inhalation or drawing, of at least one of a vapor air mixture or a condensation aerosol, comprises a housing; a chamber arranged in the housing; an air admission opening for the supply of air from the surroundings to the chamber; an electric heating element for evaporating a portion of a liquid material, wherein a vapor that is formed is mixed in the chamber with the air supplied through the air admission opening to form the at least one of the vapor air mixture or condensation aerosol; a wick with a capillary structure, wherein the wick forms a composite with the heating element and automatically resupplies the heating element with the liquid material following evaporation; and a plurality of electrical contacts each connected with the composite at a laser weld.

In an embodiment, an inhalator component for an inhalator device, for the intermittent formation, synchronous with inhalation or drawing, of at least one of a vapor air mixture or a condensation aerosol, comprises a housing; a chamber arranged in the housing; an air admission opening for the supply of air from the surroundings to the chamber; an electric heating element for evaporating a portion of a liquid material, wherein a vapor that is formed is mixed in the chamber with the air supplied through the air admission opening to form the at least one of the vapor air mixture or condensation aerosol; a wick with a capillary structure, wherein the wick forms a composite with the heating element and automatically resupplies the heating element with the liquid material following evaporation; and a buffer store configured to receive liquid material and to dispense the received liquid material to the wick when the liquid material is needed and irrespective of a position of the inhalator component. In one embodiment, the buffer store is configured to receive the liquid material from a capillary gap and dispense the liquid material via the capillary gap. In one embodiment, the capillary gap is arranged at an end of the composite.

In an embodiment, an inhalator component for an inhalator device, for the intermittent formation, synchronous with inhalation or drawing, of at least one of a vapor air mixture or a condensation aerosol, comprises a housing; a chamber arranged in the housing; an air admission opening for the supply of air from the surroundings to the chamber; an electric heating element for evaporating a portion of a liquid material, wherein a vapor that is formed is mixed in the chamber with the air supplied through the air admission opening to form the at least one of the vapor air mixture or condensation aerosol; and a wick with a capillary structure, wherein the wick forms a composite with the heating element and automatically resupplies the heating element with the liquid material following evaporation, and wherein a surface of the composite has been subjected to surface activation.

In an embodiment, an inhalator component for an inhalator device, for the intermittent formation, synchronous with inhalation or drawing, of at least one of a vapor air mixture or a condensation aerosol, comprises a housing; a chamber arranged in the housing; an air admission opening for the supply of air from the surroundings to the chamber; an electric heating element for evaporating a portion of a liquid material, wherein a vapor that is formed is mixed in the chamber with the air supplied through the air admission opening to form the at least one of the vapor air mixture or condensation aerosol; and a flow sensor comprising a first thermistor to detect a beginning of inhalation. In one embodiment, the inhalator component further comprises a second thermistor. In one embodiment, the flow sensor is arranged in an air flow path of the inhalation.

In an embodiment, an inhalator component for an inhalator device, for the intermittent formation, synchronous with inhalation or drawing, of at least one of a vapor air mixture or a condensation aerosol, comprises a housing; a chamber arranged in the housing; an air admission opening for the supply of air from the surroundings to the chamber; an electric heating element for evaporating a portion of a liquid material, wherein a vapor that is formed is mixed in the chamber with the air supplied through the air admission opening to form the at least one of the vapor air mixture or condensation aerosol; and wherein a supply of energy from the inhalator device to the heating element is divided into at least two periods, a heating up period and an evaporation period, the evaporation period following the heating up period. In one embodiment, during the evaporation period a modulated voltage is applied to the heating element. In one embodiment, during the heating up period an unmodulated voltage is applied to the heating element.

In an embodiment, an inhalator component for an inhalator device, for the intermittent formation, synchronous with inhalation or drawing, of at least one of a vapor air mixture or a condensation aerosol, comprises a housing; a chamber arranged in the housing; an air admission opening for the supply of air from the surroundings to the chamber; and an electric heating element for evaporating a portion of a liquid material, wherein a vapor that is formed is mixed in the chamber with the air supplied through the air admission opening to form the at least one of the vapor air mixture or condensation aerosol, wherein a supply of energy from the inhalator device to the heating element is for a time period less than a period of activation of the inhalator device. In one embodiment, the period of activation is a period of inhalation. In one embodiment, the period of activation is a period of activation of a switch/button by a user.

In an embodiment, inhalator component for an inhalator device, for the intermittent formation, synchronous with inhalation or drawing, of at least one of a vapor air mixture or a condensation aerosol, comprises a housing; a chamber arranged in the housing; an air admission opening for the supply of air from the surroundings to the chamber; and an electric heating element for evaporating a portion of a liquid material, wherein a vapor that is formed is mixed in the chamber with the air supplied through the air admission opening to form the at least one of the vapor air mixture or condensation aerosol, wherein a supply of energy from the inhalator device to the heating element is modulated to prevent thermal decomposition of the liquid material.

In an embodiment, an inhalator component for an inhalator device, for the intermittent formation, synchronous with inhalation or drawing, of at least one of a vapor air mixture or a condensation aerosol, comprises a housing; a chamber arranged in the housing; an air admission opening for the supply of air from the surroundings to the chamber; and an electric heating element for evaporating a portion of a liquid material, wherein a vapor that is formed is mixed in the chamber with the air supplied through the air admission opening to form the at least one of the vapor air mixture or condensation aerosol, wherein a supply of energy from the inhalator device to the heating element is modulated to control at least one characteristic of the at least one of the vapor air mixture or condensation aerosol. In one embodiment, the at least one characteristic is a quantity of liquid material evaporated per inhalation. In one embodiment, the supply of energy to the heating element is modulated during inhalation. In one embodiment, the supply of energy to the heating element is modulated between inhalations. In one embodiment, the supply of energy is modulated according to a rate of inhalation. In one embodiment, the inhalator component further comprises a user interface, wherein the supply of energy is modulated according to input received via the user interface.

In an embodiment, an inhalator component for an inhalator device, for the intermittent formation, synchronous with inhalation or drawing, of at least one of a vapor air mixture or a condensation aerosol, comprises a housing; a chamber arranged in the housing; an air admission opening for the supply of air from the surroundings to the chamber; an electric heating element for evaporating a portion of a liquid material, wherein a vapor that is formed is mixed in the chamber with the air supplied through the air admission opening to form the at least one of the vapor air mixture or condensation aerosol; and a cooler through which the at least one of the vapor air mixture or condensation aerosol passes. In one embodiment, the cooler provides aromatization of the at least one of the vapor air mixture or condensation aerosol. In one embodiment, the cooler comprises a tobacco filling. In one embodiment, the cooler is formed by the tobacco filling. In one embodiment, the cooler comprises a pore body. In one embodiment, the pore body comprises at least one of a wide-pored material, a coarse-pored porous filling material, a nonwoven fiber material or a regenerator material. In one embodiment, the pore body comprises a wide-pored material, and wherein the wide-pored material comprises an open-cell foam material. In one embodiment, the pore body comprises a nonwoven fiber material, and wherein the nonwoven fiber material comprises a synthetic nonwoven fiber material. In one embodiment, the synthetic nonwoven fiber material comprises polyolefin fibers or polyester fibers. In one embodiment, the pore body comprises a regenerator material, and wherein the regenerator material comprises at least one of a metal wool, a metal chip, a metal mesh, a wire knit, a metal nonwoven, an open-cell metal foam, a metallic granular material, or a ceramic granular material.

In an embodiment, an inhalator component for an inhalator device, for the intermittent formation, synchronous with inhalation or drawing, of at least one of a vapor air mixture or a condensation aerosol, comprises a housing; a chamber arranged in the housing; an air admission opening for the supply of air from the surroundings to the chamber; an electric heating element for evaporating a portion of a liquid material, wherein the electric heating element comprises an induction heating element, and wherein a vapor that is formed is mixed in the chamber with the air supplied through the air admission opening to form the at least one of the vapor air mixture or condensation aerosol; and a wick with a capillary structure, wherein the wick forms a composite with the electric heating element and automatically resupplies the electric heating element with the liquid material following evaporation.

LIST OF REFERENCE NUMBERS

1 Inhalator part
2 Inhalator component
3 Housing
4 Liquid container
5 Mouthpiece
6 Battery cover
7 Switching circuit cover
8 Snap-in hook
9 Latching lug
10 Support housing
11 Electric switching circuit, printed circuit board
12 Energy store; battery
13 Partition
14 Flat contact
15 Window
16 Liquid material; drug preparation
17 Filling hole
18 Openable closure
19 Closure cover
20 Contact element
21 Chamber
22, 22a, 22b Planar composite
23, 23a, 23b, 23c Plate-like contact
24 First side of the planar composite
25 Second side of the planar composite
26 Air admission opening; slot-shaped channel
27 Plenum chamber
28 Flow throttle
29 Transverse channel
30 Feeding opening
31 Film; metal foil
32 Fabric; metal wire mesh
33 Open-pored fiber structure; nonwoven fabric
34 Open-pored sintered structure; granular, fibrous or flocculent sintered composite
35 Channel; artery
36 Hole
37 Open-pored foam
38 Support layer
39 Linear composite
40 Ram
41 Capillary gap
42 Upper part
43 Plate
44 Extension
45 Reservoir
46 Pin
47 First end
48 Second end
49 Material weakening
50 Hinge
51 Cross-sectional expansion
52 Ventilation duct
53 Buffer store
54 Capillary; slot
55 Opening
56 Ventilation gap
57 Open-pored, absorbent body; sponge
58 Flow duct
59 Wall section
60 Gap
61 Cooler; filling material; tobacco filling
62 Filling space
63 Perforated wall
64 First wire mesh
65 Second wire mesh
66 Mouthpiece channel
67 Collecting chamber
68 Bypass opening
69 Guide vane
70 Guide vane tip
71 Mouth opening
72 Flow homogenizer
73 Blocking device which cannot be unlocked; projection
74 Catch
75 Groove
76 Venting opening
77 Venting duct
78 First opening
79 Second opening
80 Film seal
81 First spike 82 Second spike
83 Microweb
84 Liquid store; open-pored foam
85 Cartridge housing
86 Cartridge
87 Recess
88 Cover
89 Snap connection
90 Elevation
91 Ventilation hole
92 Cutout
93 Plug contact
94 Spring contact
95 Wire
96 Centering projection
97 Centering recess
98 Venting hole
99 Pressure sensor
100 Flow sensor, thermistor
101 Electric connection; pin
102 Bore
103 Operation booster; comparator
104 Integrated switching circuit; microprocessor
105 Power MOSFET
106 Light-emitting diode
107 Charging plug
108 Recess
109 Small locking plate
110 Connecting web

What is claimed is:

1. An inhalator component for an inhalator device, for the intermittent formation, synchronous with inhalation or drawing, of at least one of a vapor air mixture or a condensation aerosol, the inhalator component comprising:
    a housing;
    a chamber arranged in the housing;
    an air admission opening for a supply of air from surroundings to the chamber;
    an electric heating element for evaporating a portion of a liquid material, wherein the electric heating element is configured to form a vapor to be mixed in the chamber with air supplied through the air admission opening to form the at least one of the vapor air mixture or condensation aerosol; and
    a wick with a capillary structure, wherein the wick forms a composite with the electric heating element and automatically resupplies the electric heating element with the liquid material following evaporation, wherein the composite has a maximum thickness of less than 0.6 millimeters (mm) and wherein the capillary structure of the composite is exposed to the chamber over a majority of the wick.

2. The inhalator component of claim 1, wherein the composite has a maximum thickness of less than 0.3 mm.

3. An inhalator component for an inhalator device, for the intermittent formation, synchronous with inhalation or drawing, of at least one of a vapor air mixture or a condensation aerosol, the inhalator component comprising:
    a housing;
    a chamber arranged in the housing;
    an air admission opening for a supply of air from surroundings to the chamber;
    an electric heating element for evaporating a portion of a liquid material, wherein the electric heating element is configured to form a vapor to be mixed in the chamber with air supplied through the air admission opening to form the at least one of the vapor air mixture or condensation aerosol; and
    a wick with a capillary structure, wherein the wick forms a composite with the electric heating element and automatically resupplies the electric heating element with the liquid material following evaporation, wherein the composite has a porosity of greater than 50% and wherein the capillary structure of the composite is exposed to the chamber of a majority of the wick.

4. The inhalator component of claim 3, wherein the composite has a porosity of greater than 70%.

5. The inhalator component of claim 3, wherein the composite has a porosity of greater than 90%.

6. An inhalator component for an inhalator device, for the intermittent formation, synchronous with inhalation or drawing, of at least one of a vapor air mixture or a condensation aerosol, the inhalator component comprising:
    a housing;
    a chamber arranged in the housing;
    an air admission opening for a supply of air from surroundings to the chamber;
    an electric heating element for evaporating a portion of a liquid material, wherein the electric heating element is configured to form a vapor to be mixed in the chamber with air supplied through the air admission opening to form the at least one of the vapor air mixture or condensation aerosol; and
    a wick with a capillary structure, wherein the wick forms a composite with the electric heating element and automatically resupplies the electric heating element with the liquid material following evaporation, wherein the electric heating element is at least partially integrated in the wick and the wick at least partially consists of an electric resistance material, and wherein the composite has an open-pored sintered structure and wherein the capillary structure of the composite is exposed to the chamber over a majority of the wick.

7. The inhalator component of claim 6, wherein the open-pored sintered structure comprises a fibrous sintered structure.

8. The inhalator component of claim 6, wherein the open-pored sintered structure comprises a granular sintered structure.

9. The inhalator component of claim 6, wherein the open-pored sintered structure comprises a mesh.

10. The inhalator component of claim 9, wherein the mesh comprises stainless steel.

11. An inhalator component for an inhalator device, for the intermittent formation, synchronous with inhalation or drawing, of at least one of a vapor air mixture or a condensation aerosol, the inhalator component comprising:
    a housing;
    a chamber arranged in the housing;
    an air admission opening for a supply of air from surroundings to the chamber;
    an electric heating element for evaporating a portion of a liquid material, wherein the electric heating element is configured to form a vapor to be mixed in the chamber with air supplied through the air admission opening to form the at least one of the vapor air mixture or condensation aerosol;
    a wick with a capillary structure, wherein the wick forms a composite with the electric heating element and automatically resupplies the electric heating element with the liquid material following evaporation, wherein the electric heating element is integrated in the wick along the entire length of the composite, and the wick at least partially consists of an electric resistance material; and a plurality of electrical contacts each connected with the composite at a laser weld.

12. An inhalator component for an inhalator device, for the intermittent formation, synchronous with inhalation or drawing, of at least one of a vapor air mixture or a condensation aerosol, the inhalator component comprising:

a housing;

a chamber arranged in the housing;

an air admission opening for a supply of air from surroundings to the chamber;

a liquid container, arranged in the housing or connected to the housing, that contains a liquid material;

an electric heating element for evaporating a portion of the liquid material, wherein the electric heating element is configured to form a vapor to be mixed in the chamber with air supplied through the air admission opening to form the at least one of the vapor air mixture or condensation aerosol;

a wick with a capillary structure, wherein the wick forms a composite with the heating element and automatically resupplies the heating element with the liquid material following evaporation, wherein the heating element is integrated in the wick along the entire length of the composite, and wherein the wick is in connection with the liquid container; and a buffer store that is in connection with the liquid container and is configured to receive liquid material from the liquid container and to dispense the received liquid material to the wick for automatic resupplying of the electric heating element with the liquid material following evaporation.

13. The inhalator component of claim 12, wherein the buffer store is configured to receive the liquid material from a capillary gap and dispense the liquid material via the capillary gap.

14. The inhalator component of claim 13, wherein the capillary gap is arranged at an end of the composite.

15. An inhalator component for an inhalator device, for the intermittent formation, synchronous with inhalation or drawing, of at least one of a vapor air mixture or a condensation aerosol, the inhalator component comprising:

a housing;

a chamber arranged in the housing;

an air admission opening for a supply of air from surroundings to the chamber;

an electric heating element for evaporating a portion of a liquid material, wherein the electric heating element comprises an induction heating element, and wherein the electric heating element is configured to form a vapor to be mixed in the chamber with the air supplied through the air admission opening to form the at least one of the vapor air mixture or condensation aerosol; and a wick with a capillary structure, wherein the wick forms a composite with the electric heating element and automatically resupplies the electric heating element with the liquid material following evaporation, and wherein the electric heating element is at least partially integrated in the wick and the wick at least partially consists of an electric resistance material and wherein the capillary structure of the composite is exposed to the chamber over a majority of the wick.

* * * * *